(12) United States Patent
Polonsky et al.

(10) Patent No.: US 12,343,221 B2
(45) Date of Patent: Jul. 1, 2025

(54) SYSTEMS AND METHODS FOR SENSING PRESENCE OF MEDICAL TOOLS

(71) Applicant: Intuitive Surgical Operations, Inc., Sunnyvale, CA (US)

(72) Inventors: Andrey Polonsky, Rochester, NY (US); Eric J. Earnst, Saratoga, CA (US); Jean-Marc Gery, Los Angeles, CA (US); Andrew J. Hazelton, San Carlos, CA (US); Sarah A. Nichols, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 902 days.

(21) Appl. No.: 17/258,713

(22) PCT Filed: Jul. 9, 2019

(86) PCT No.: PCT/US2019/040974
§ 371 (c)(1),
(2) Date: Jan. 7, 2021

(87) PCT Pub. No.: WO2020/014207
PCT Pub. Date: Jan. 16, 2020

(65) Prior Publication Data
US 2021/0153975 A1    May 27, 2021

Related U.S. Application Data

(60) Provisional application No. 62/696,082, filed on Jul. 10, 2018.

(51) Int. Cl.
*A61B 90/98*    (2016.01)
*A61B 34/20*    (2016.01)
(Continued)

(52) U.S. Cl.
CPC .............. *A61B 90/98* (2016.02); *A61B 34/20* (2016.02); *A61B 34/35* (2016.02); *A61B 34/37* (2016.02);
(Continued)

(58) Field of Classification Search
CPC ......... A61B 90/98; A61B 34/20; A61B 34/35; A61B 34/37; A61B 90/37;
(Continued)

(56) References Cited

U.S. PATENT DOCUMENTS

| 5,437,290 A | 8/1995 | Bolger et al. |
| 6,380,732 B1 | 4/2002 | Gilboa |

(Continued)

FOREIGN PATENT DOCUMENTS

| CN | 105142514 A | 12/2015 |
| CN | 106470622 A | 3/2017 |

(Continued)

OTHER PUBLICATIONS

International Search Report and Written Opinion for Application No. PCT/US2019/040974, mailed on Jan. 2, 2020, 18 pages.

(Continued)

*Primary Examiner* — Joseph M Dietrich
*Assistant Examiner* — Michael T. Holtzclaw
(74) *Attorney, Agent, or Firm* — Haynes & Boone, LLP.

(57) ABSTRACT

A system including a tool recognition assembly comprising a first target reader with a first detection zone. The system also includes a tool configured to be installed in the tool recognition assembly, wherein the first reader detects a first reading indicating a presence or absence of the first target in the first detection zone during an installation of the tool in the tool recognition assembly, the detected first reading being at least a part of a detected insertion signature, and provides the detected insertion signature to initiate a com- (Continued)

parison of the detected insertion signature to one or more model signatures.

20 Claims, 30 Drawing Sheets

(51) Int. Cl.
    *A61B 34/30* (2016.01)
    *A61B 34/35* (2016.01)
    *A61B 34/37* (2016.01)
    *A61B 90/00* (2016.01)
    *A61M 25/01* (2006.01)

(52) U.S. Cl.
    CPC ......... *A61B 90/37* (2016.02); *A61M 25/0105* (2013.01); *A61B 2034/2051* (2016.02); *A61B 2034/301* (2016.02); *A61M 2025/0166* (2013.01)

(58) Field of Classification Search
    CPC ..... A61B 2034/2051; A61B 2034/301; A61M 25/0105; A61M 2025/0166
    USPC ............................................................ 606/1
    See application file for complete search history.

(56) References Cited

U.S. PATENT DOCUMENTS

| | | | |
|---|---|---|---|
| 6,389,187 | B1 | 5/2002 | Greenaway et al. |
| 7,316,681 | B2 | 1/2008 | Madhani et al. |
| 7,772,541 | B2 | 8/2010 | Froggatt et al. |
| 8,900,131 | B2 | 12/2014 | Chopra et al. |
| 9,259,274 | B2 | 2/2016 | Prisco |
| 9,452,276 | B2 | 9/2016 | Duindam et al. |
| 2003/0199856 | A1* | 10/2003 | Hill .................. A61B 17/16 606/1 |
| 2005/0203544 | A1* | 9/2005 | Revie .................. A61B 90/96 606/180 |
| 2006/0013523 | A1 | 1/2006 | Childlers et al. |
| 2007/0100405 | A1 | 5/2007 | Thompson et al. |
| 2008/0185430 | A1* | 8/2008 | Goldbach .............. A61B 34/20 235/385 |
| 2008/0319570 | A1* | 12/2008 | Van Schoiack ......... B25B 21/00 700/110 |
| 2009/0272806 | A1* | 11/2009 | Kemp .................. B23K 26/355 235/492 |
| 2012/0190987 | A1 | 7/2012 | Hyoun et al. |
| 2015/0164606 | A1* | 6/2015 | Jacobs .................. A61B 34/20 606/1 |
| 2015/0359597 | A1* | 12/2015 | Gombert ................ B25J 9/0087 901/8 |
| 2017/0086906 | A1 | 3/2017 | Tsuruta |
| 2017/0224438 | A1* | 8/2017 | Johnson ................ A61B 90/90 |
| 2017/0325899 | A1 | 11/2017 | Potter et al. |
| 2018/0092710 | A1* | 4/2018 | Bosisio ................ A61B 5/6844 |
| 2018/0256287 | A1* | 9/2018 | Bosisio .................... A61C 5/42 |
| 2019/0343597 | A1* | 11/2019 | Corpa De La Fuente ................ A61B 17/1617 |
| 2021/0153724 | A1* | 5/2021 | Ries ................... A61B 1/00097 |

FOREIGN PATENT DOCUMENTS

| | | |
|---|---|---|
| CN | 108136158 A | 6/2018 |
| EP | 2941188 A1 | 11/2015 |
| JP | 2003070803 A | 3/2003 |
| JP | 2008516722 A | 5/2008 |
| JP | 2016007275 A | 1/2016 |
| JP | 2016517299 A | 6/2016 |
| WO | WO-2006043276 A2 | 4/2006 |
| WO | WO-2007041094 A1 | 4/2007 |
| WO | WO-2014149472 A1 | 9/2014 |
| WO | WO-2017004307 A1 | 1/2017 |
| WO | WO-2018013417 A1 | 1/2018 |
| WO | WO-2018057633 A1 | 3/2018 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/2019/040974, mailed on Jan. 21, 2021, 11 pages.

\* cited by examiner

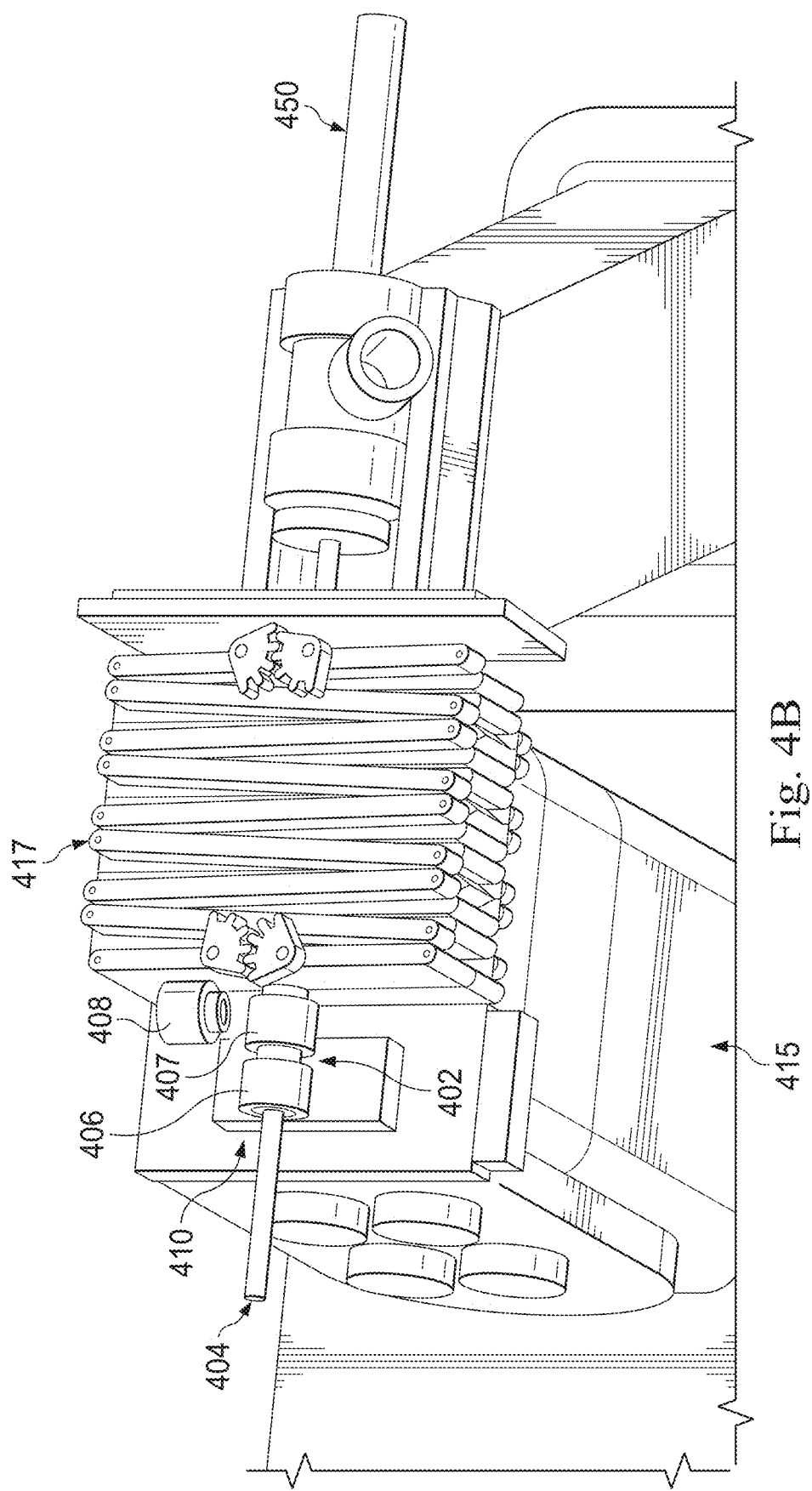

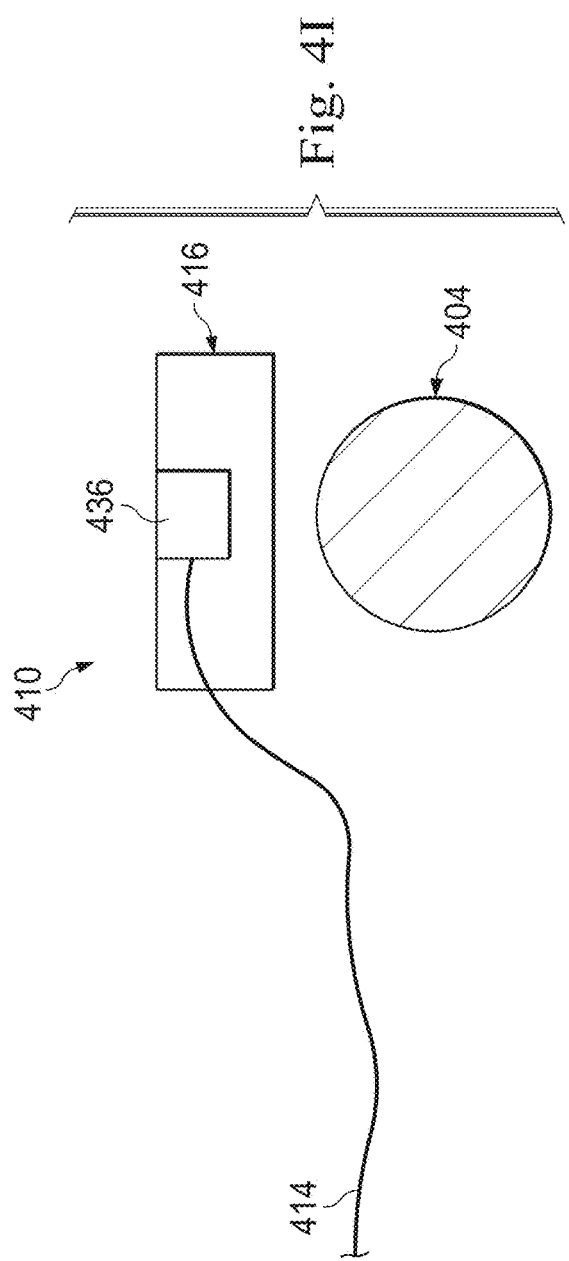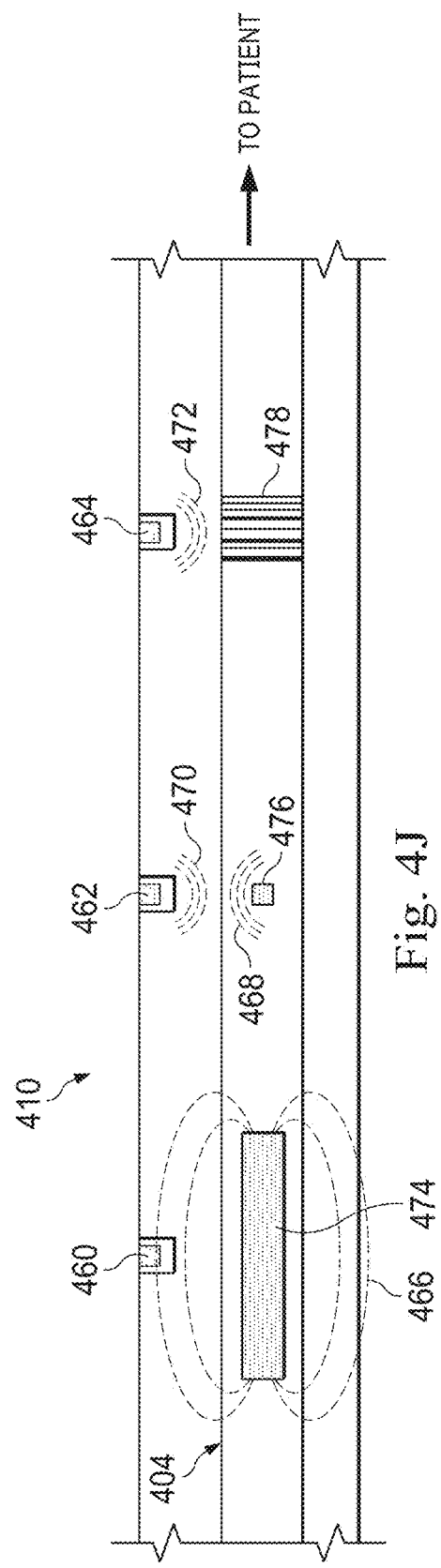

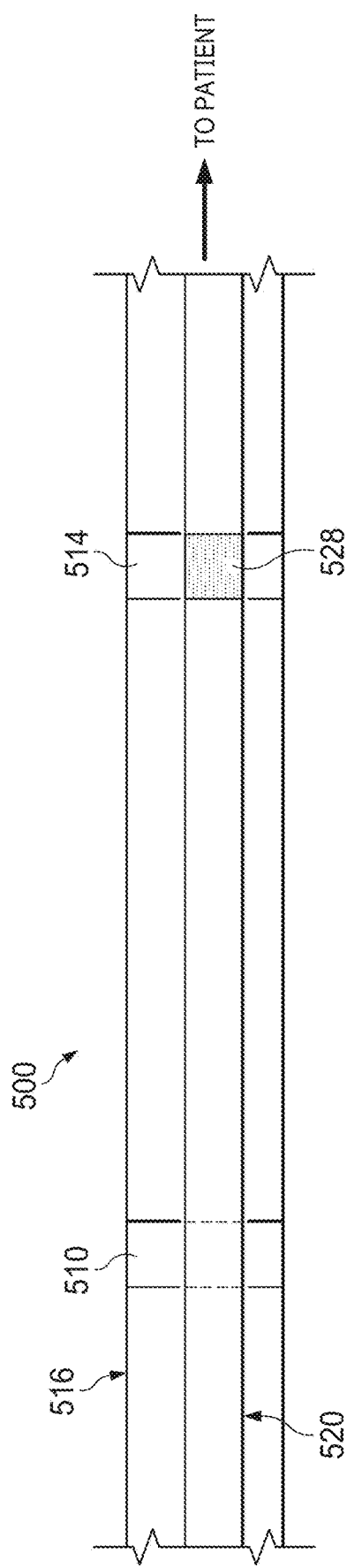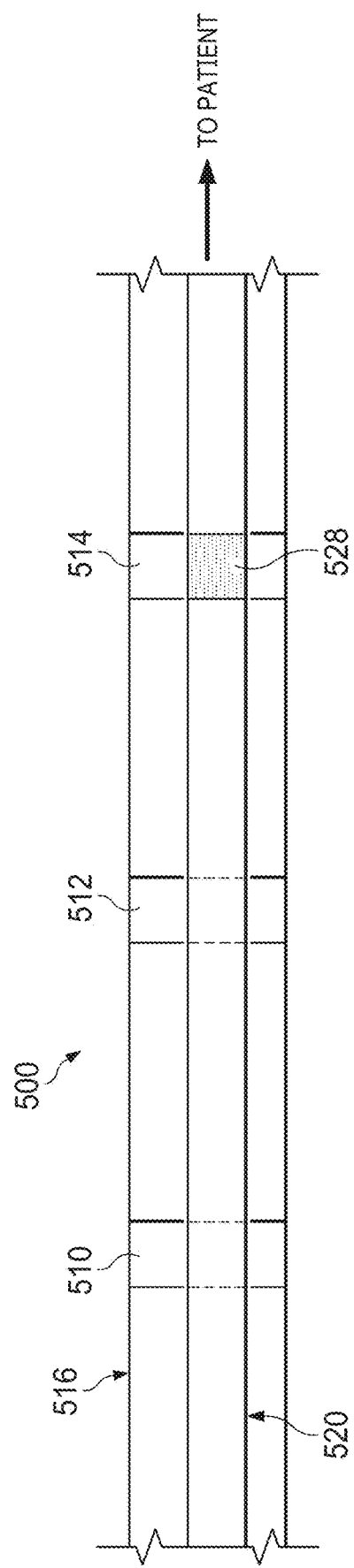

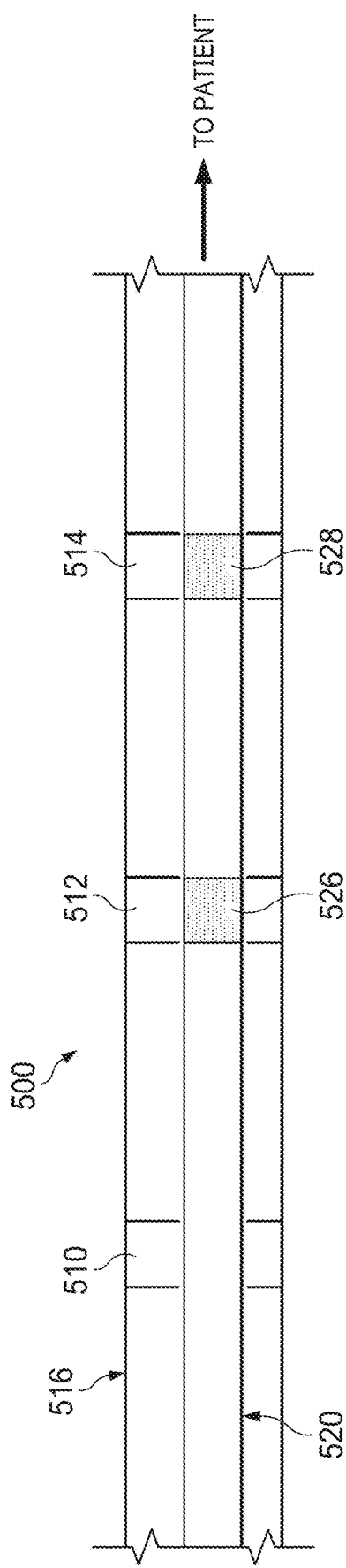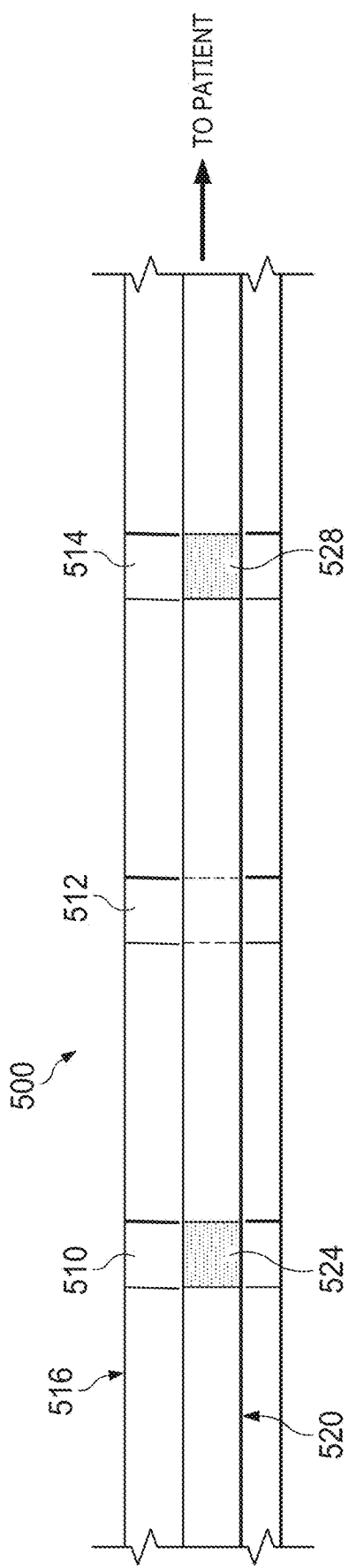

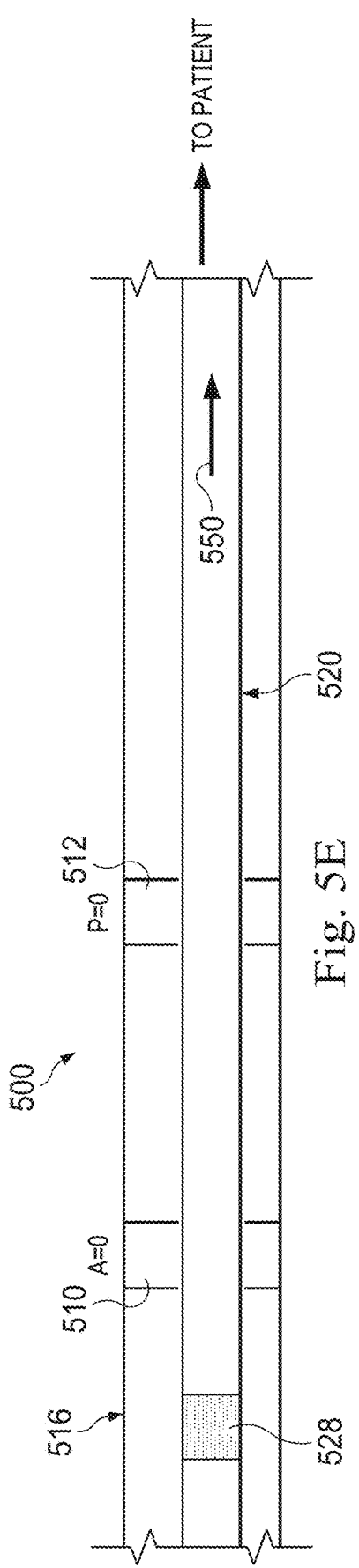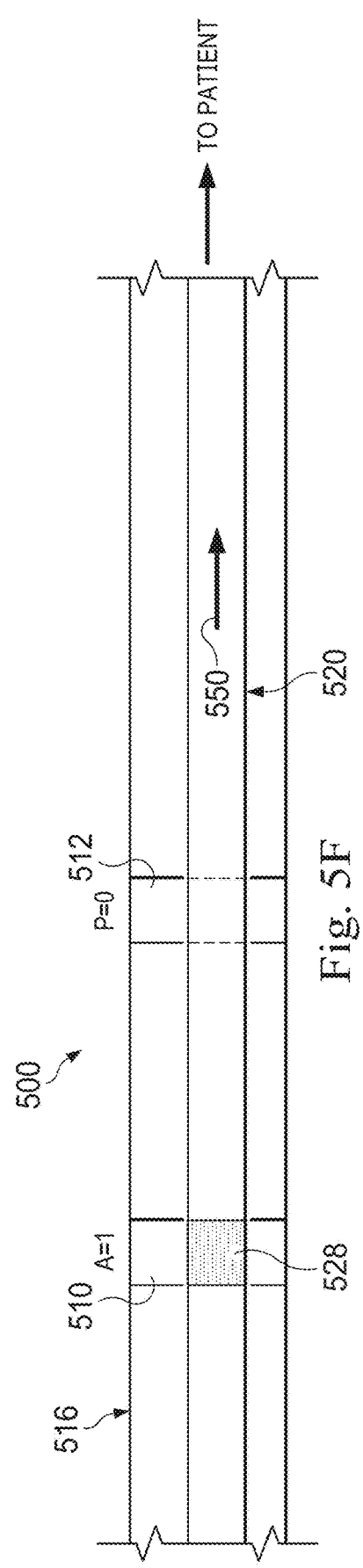

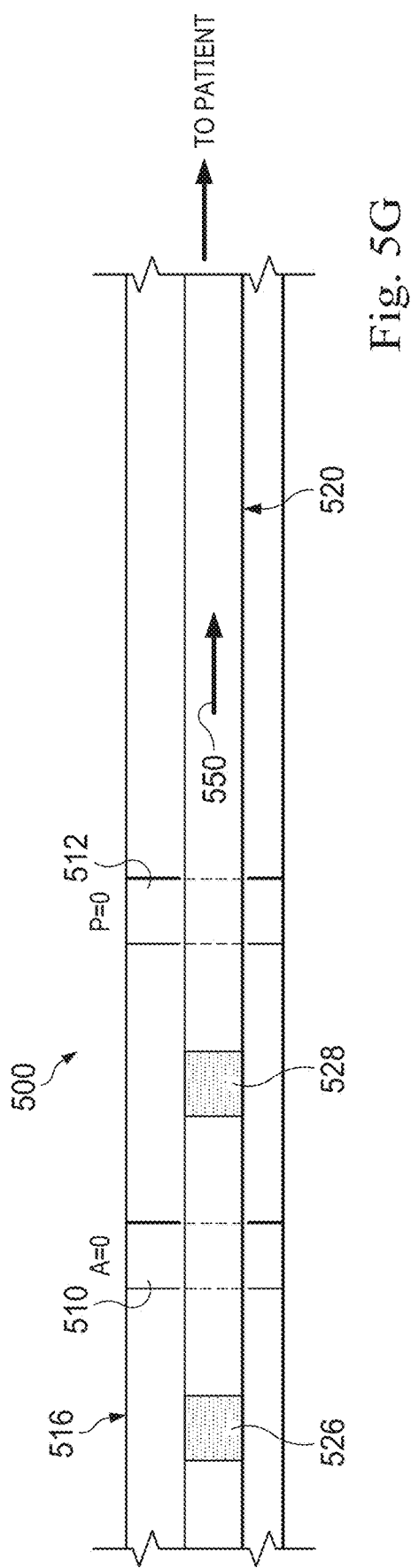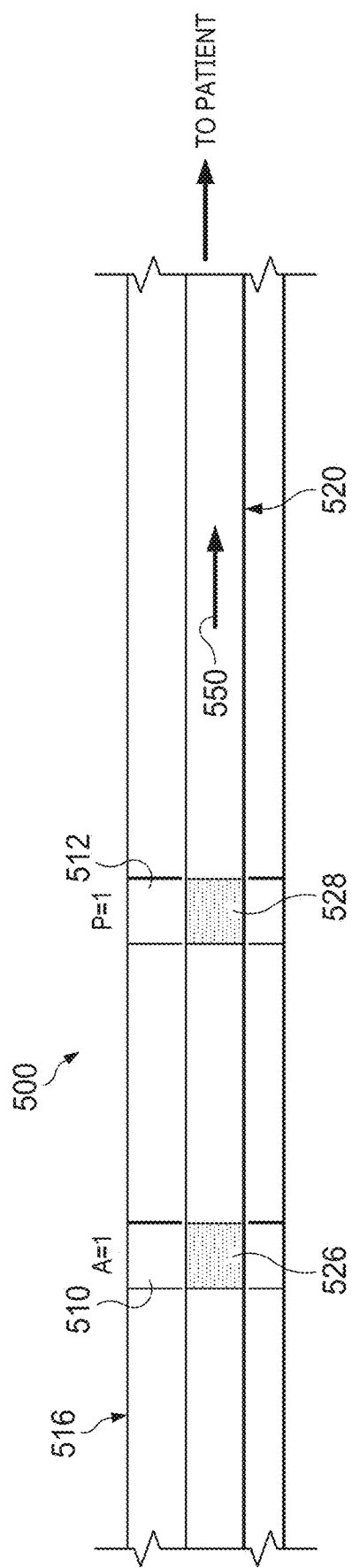

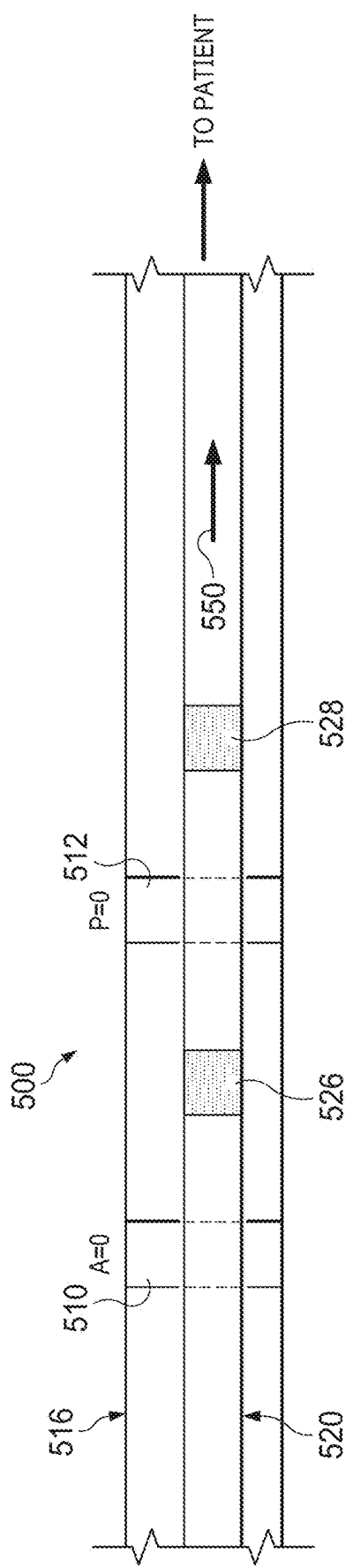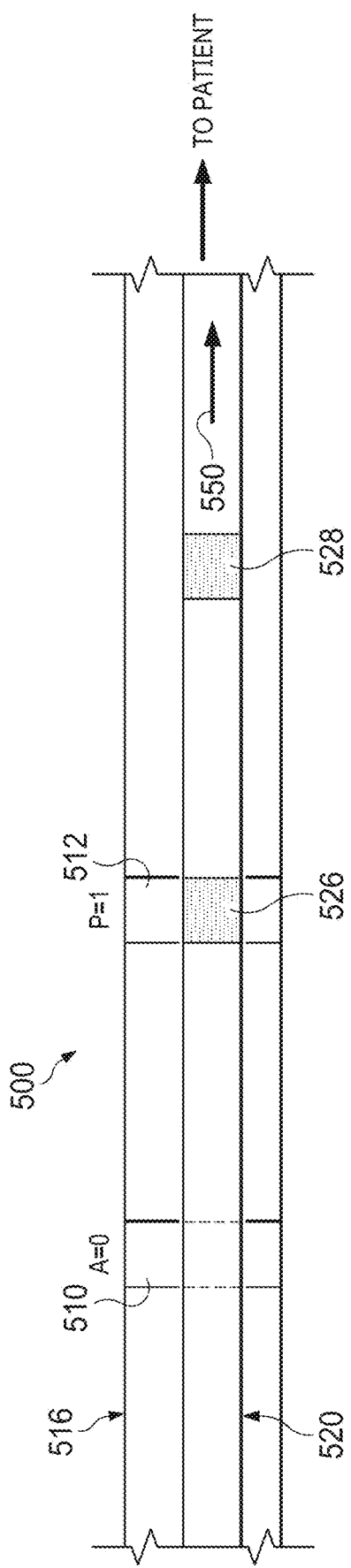

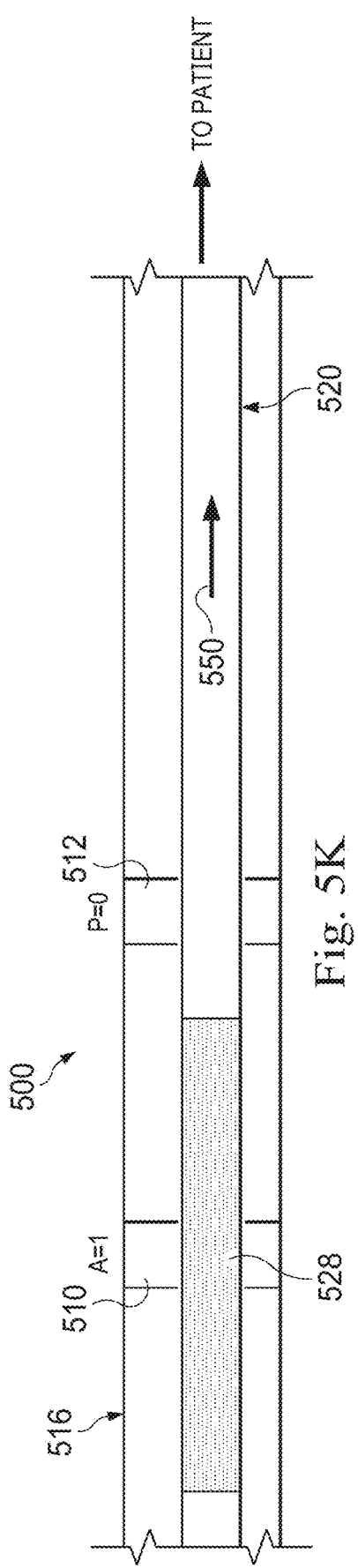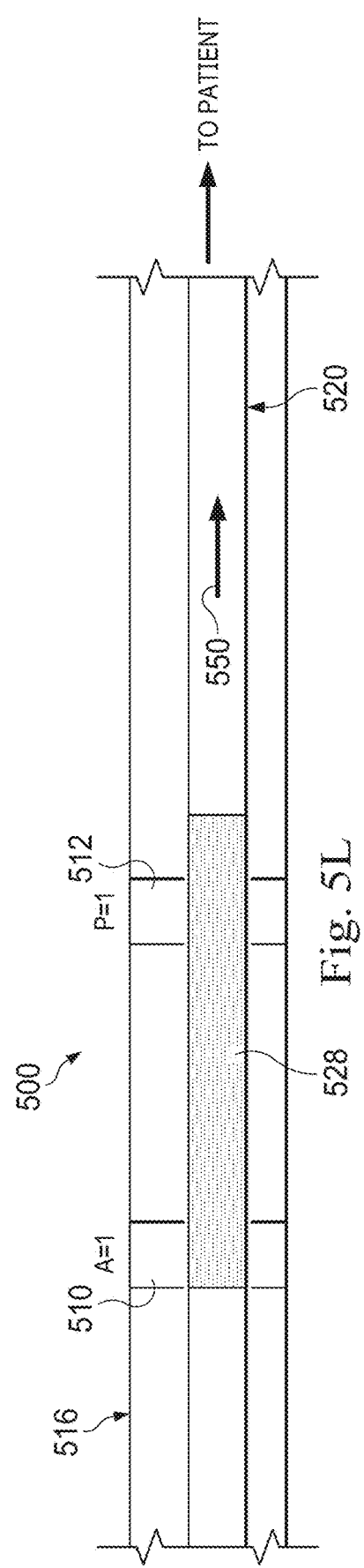

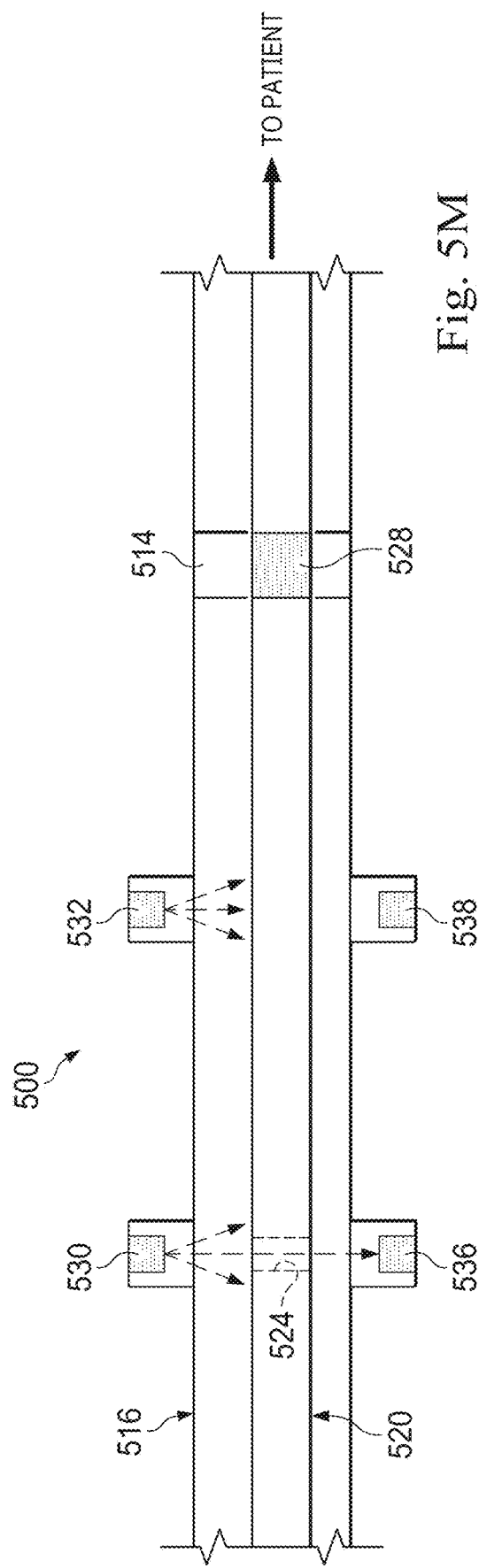
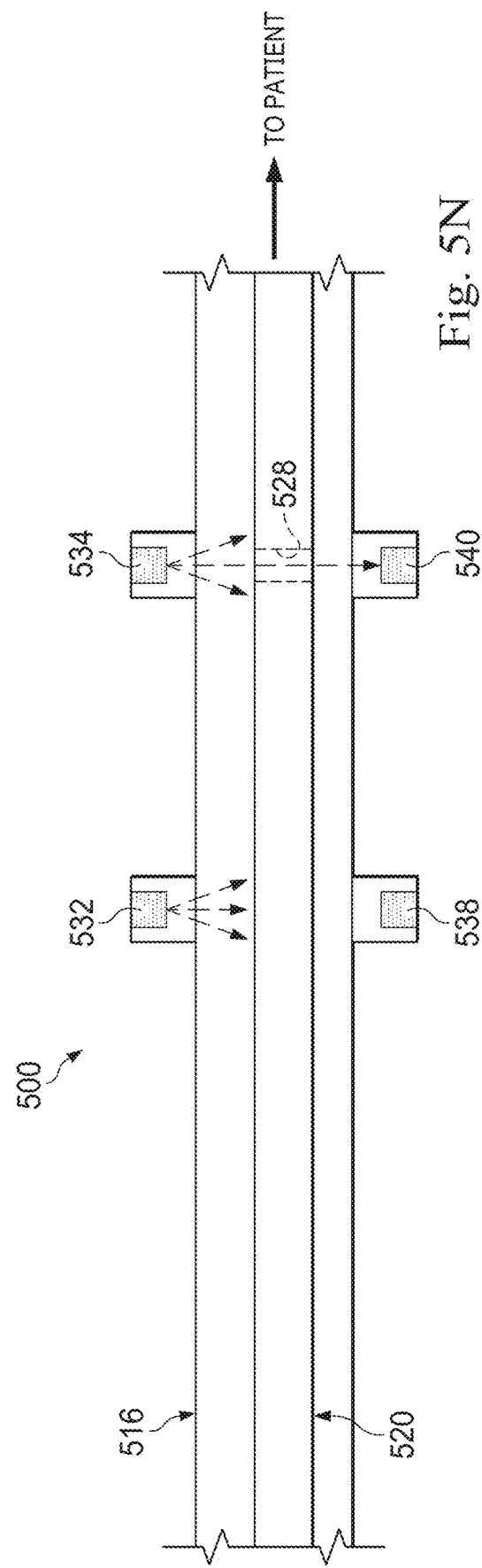

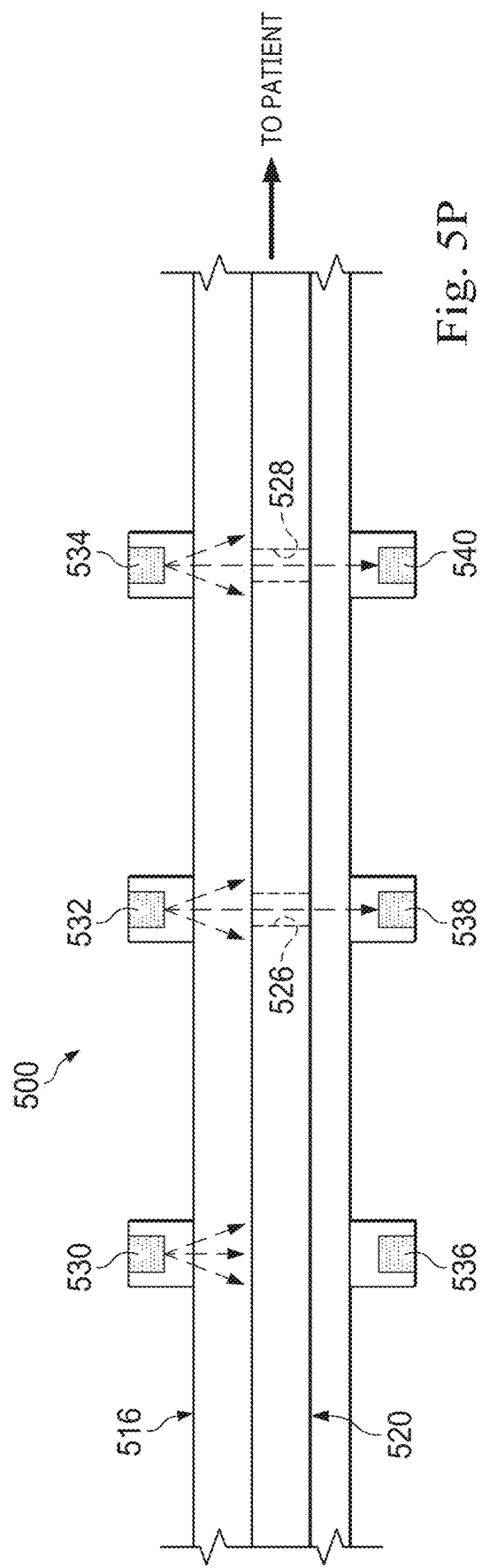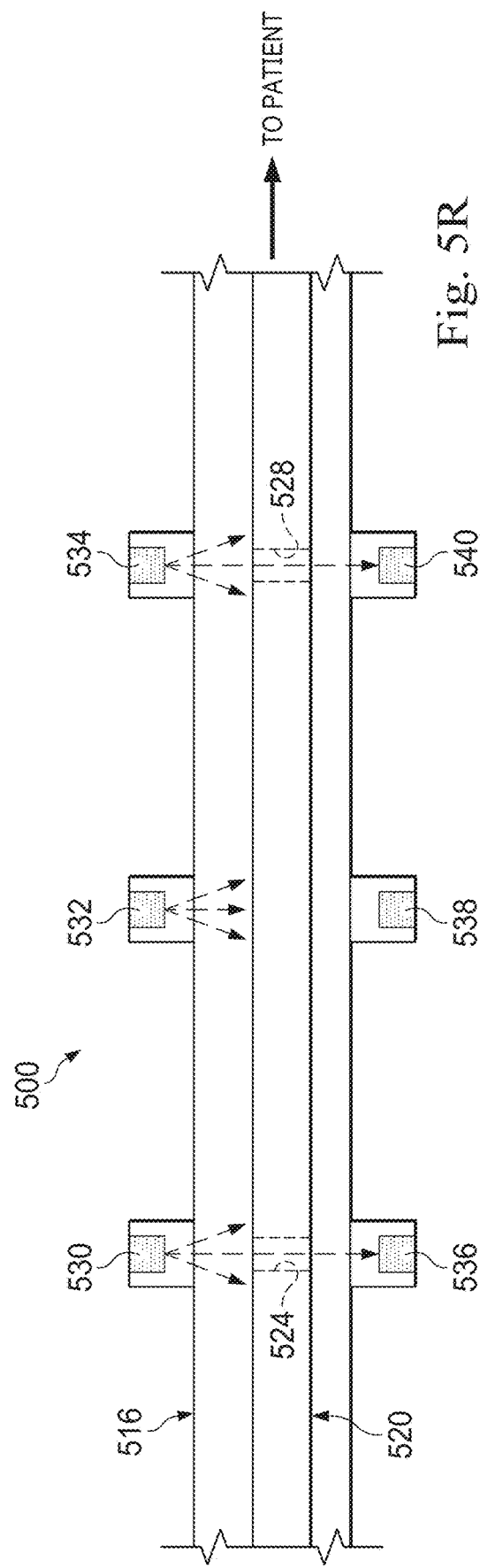

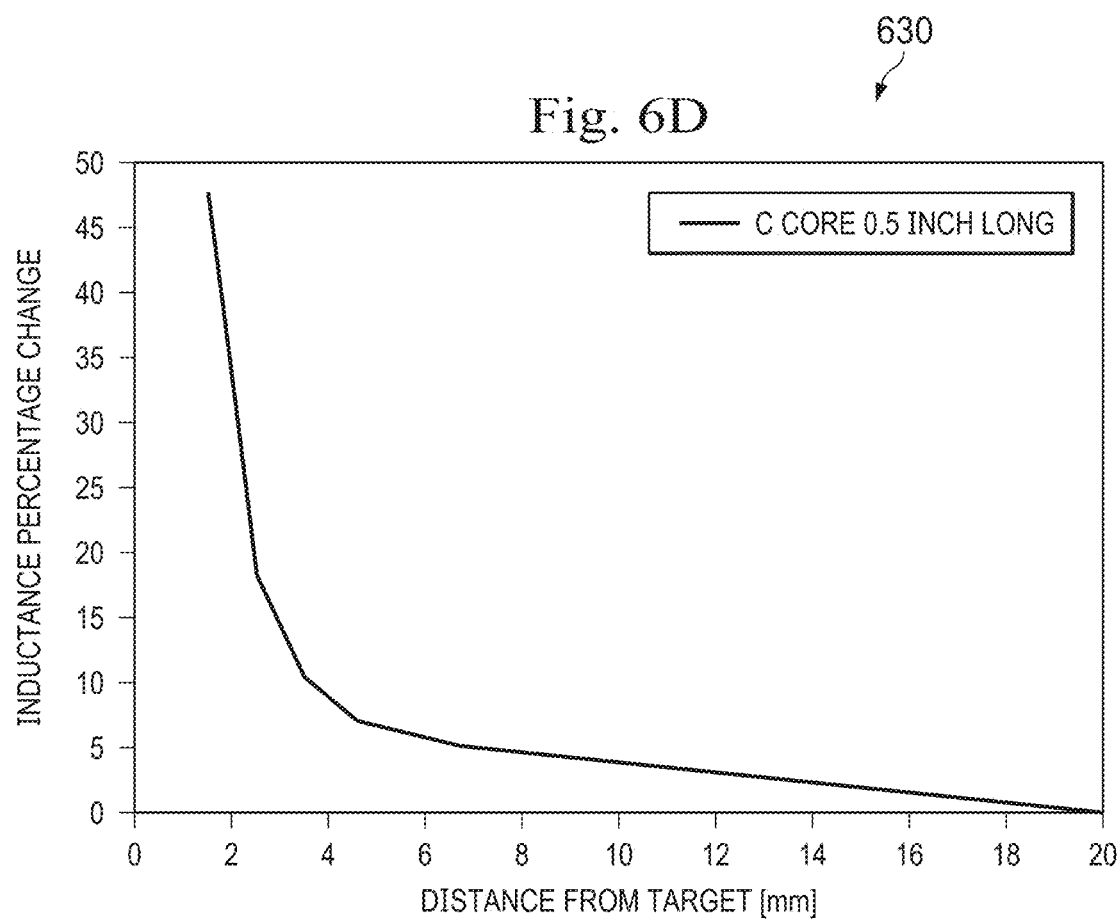
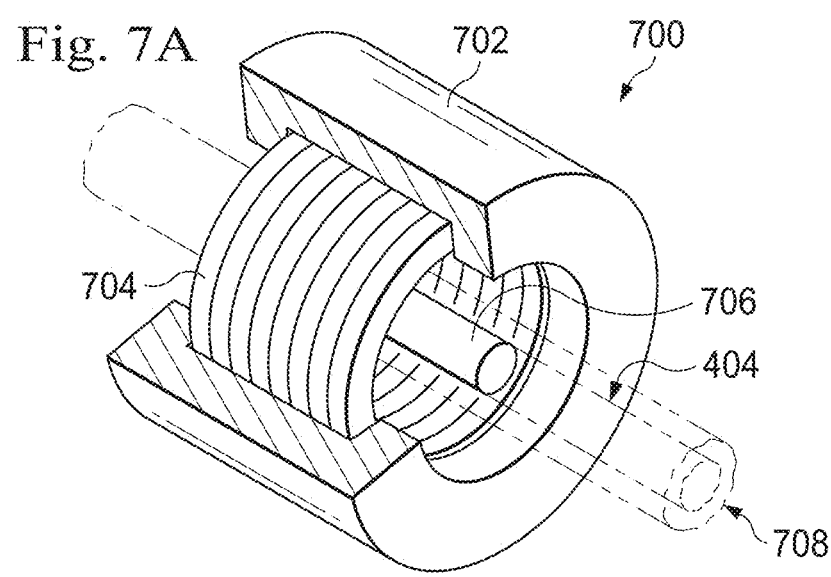

| CORE LENGTH | CURRENT | INDUCTANCE | | | INDUCTANCE CHANGE | DESCRIPTION | DIST TO CL |
|---|---|---|---|---|---|---|---|
| [mm] | [AT] | [H/squareT] | | | [%] | | [mm] |
| 13 | 32 | 9.13E-09 | 4.79E-09 | 4.58E-09 | 91% | OD 16mm | 4.5 |
| 13 | 16 | 9.41E-09 | 1.78E-09 | N/A | 430% | OD 11mm | 2.5 |
| 6 | 6 | 8.91E-09 | 3.69E-09 | 3.16E-09 | 141% | OD 8mm | 2.5 |

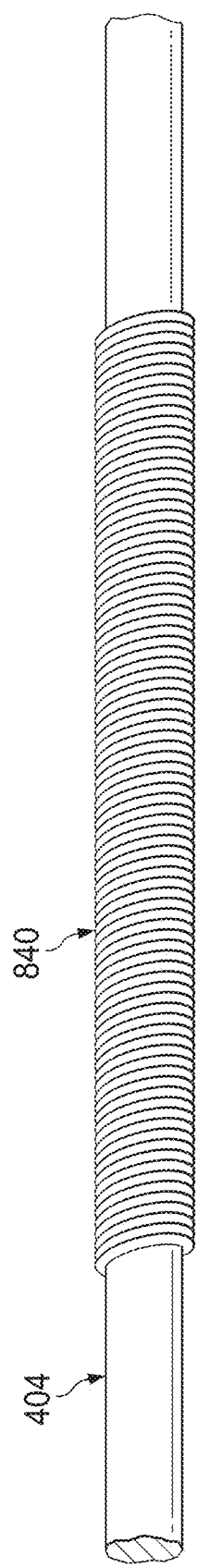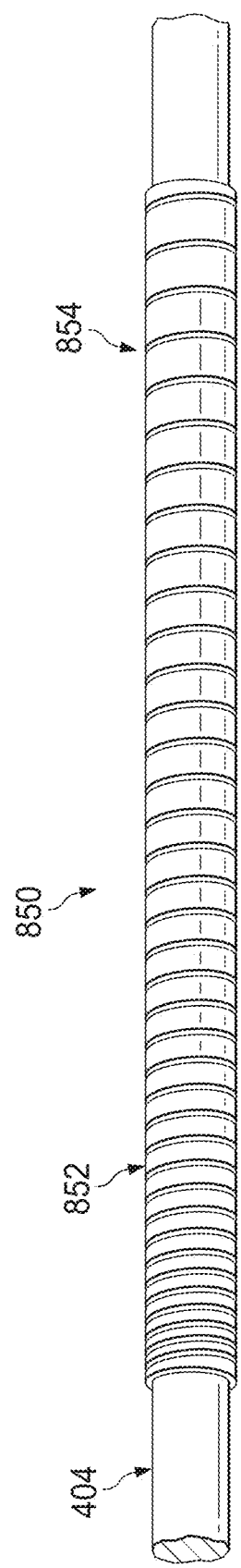

| ALGORITHM | ALGORITHM SEQUENCE | STRIPE DETECT | TARGET LOCATION | | | |
|---|---|---|---|---|---|---|
| | | | NEAR PROXIMAL END | | PROXIMAL END | |
| | | | ABSENCE READER | PRESENCE READER | ABSENCE READER | PRESENCE READER |
| 1 (1002) | 1.1 | NO | N/A | N/A | 0 | 0 |
| | 1.2 | | N/A | N/A | 1 | 0 |
| | 1.3 | | N/A | N/A | 0 | 1 |
| 2 (1004) | 2.1 | YES | N/A | N/A | 0 | 0 |
| | 2.2 | | N/A | N/A | 1 | 0 |
| | 2.3 | | N/A | N/A | 0 | 1 |
| 3 (1006) | 3.1 | NO | 0 | 0 | N/A | N/A |
| | 3.2 | | 1 | 0 | N/A | N/A |
| | 3.3 | | 0 | 1 | N/A | N/A |
| | 3.4 | | 0 | 0 | N/A | N/A |
| 4 (1008) | 4.1 | NO | 0 | 0 | 0 | 0 |
| | 4.2 | | 1 | 0 | 0 | 0 |
| | 4.3 | | 0 | 1 | 0 | 0 |
| | 4.4 | | 0 | 0 | 1 | 0 |
| | 4.5 | | 0 | 0 | 0 | 1 |
| 5 (1010) | 5.1 | YES | 0 | 0 | 0 | 0 |
| | 5.2 | | 1 | 0 | 0 | 0 |
| | 5.3 | | 0 | 1 | 0 | 0 |
| | 5.4 | | 0 | 0 | 1 | 0 |
| | 5.5 | | 0 | 0 | 0 | 1 |

Fig. 10B

| ALGORITHM | ALGORITHM SEQUENCE | STRIPE DETECT | TARGET LOCATION ||||
| | | | NEAR PROXIMAL END || PROXIMAL END ||
| | | | ABSENCE READER | PRESENCE READER | ABSENCE READER | PRESENCE READER |
|---|---|---|---|---|---|---|
| 6 | 6.1 | NO | N/A | N/A | 0 | 0 |
|   | 6.2 |    | N/A | N/A | 1 | 0 |
|   | 6.3 |    | N/A | N/A | 1 | 1 |
|   | 6.4 |    | N/A | N/A | 0 | 1 |
| 7 | 7.1 | NO | 0 | 0 | N/A | N/A |
|   | 7.2 |    | 1 | 0 | N/A | N/A |
|   | 7.3 |    | 1 | 1 | N/A | N/A |
|   | 7.4 |    | 0 | 1 | N/A | N/A |
|   | 7.5 |    | 0 | 0 | N/A | N/A |
| 8 | 8.1 | NO | 0 | 0 | 0 | 0 |
|   | 8.2 |    | 1 | 0 | 0 | 0 |
|   | 8.3 |    | 1 | 1 | 0 | 0 |
|   | 8.4 |    | 0 | 1 | 1 | 0 |
|   | 8.5 |    | 0 | 0 | 1 | 1 |
|   | 8.6 |    | 0 | 0 | 0 | 1 |
|   | 8.7 |    | 0 | 0 | 0 | 1 |
| 9 | 9.1 | YES | 0 | 0 | 0 | 0 |
|   | 9.2 |     | 1 | 1 | 0 | 0 |
|   | 9.3 |     | 1 | 0 | 0 | 0 |
|   | 9.4 |     | 0 | 1 | 1 | 1 |
|   | 9.5 |     | 0 | 0 | 1 | 1 |
|   | 9.6 |     | 0 | 0 | 0 | 0 |
|   | 9.7 |     | 0 | 0 | 0 | 1 |

SYSTEMS AND METHODS FOR SENSING PRESENCE OF MEDICAL TOOLS

CROSS-REFERENCE TO RELATED APPLICATIONS

This application is the U.S. national phase of International Application No. PCT/US2019/040974, filed Jul. 9, 2019, which designated the U.S. and claims priority to and the benefit of U.S. Provisional Application No. 62/696,082 filed Jul. 10, 2018, both of which are incorporated by reference herein in their entirety.

TECHNICAL FIELD

The present disclosure is directed to systems and methods for detecting and recognizing a tool and in various embodiments may include determining proper installation of the tool, tool type, tool controls, and/or other characteristics of the tool and its use.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physician may insert minimally invasive medical instruments (including surgical, diagnostic, therapeutic, or biopsy instruments) to reach a target tissue location. Some minimally invasive medical tools may be teleoperated or otherwise computer-assisted. Proper installation and recognition of medical instruments allows for safe and effective use of the instruments during medical procedures. Accordingly, systems and methods are needed to determine proper installation and allow recognition of medical instruments.

SUMMARY

Some embodiments of the invention are best summarized by the claims that follow the description.

Consistent with some embodiments, a system is provided. The system may include a tool recognition assembly comprising a first reader with a first detection zone. The system may further include a tool configured to be installed in the tool recognition assembly, and the tool may comprise a first target. The first reader may detect a first reading indicating a presence or absence of the first target in the first detection zone during an installation of the tool in the tool recognition assembly. The detected first reading may be at least a part of a detected insertion signature. The first reader may also provide the detected insertion signature to initiate a comparison of the detected insertion signature to one or more model signatures.

Consistent with other embodiments, a system is provided. The system may include a tool including a first target. The system may further include a receiving member configured to receive the tool. The system may further include a first reader positioned along the receiving member. The first reader may be configured to detect a presence indication of the first target of the tool when the first target is proximate the first reader during an installation of the tool and an absence indication of the first target of the tool when the first target is out of range of the first reader during the installation of the tool. The system may further include a control system communicatively linked to the first reader and configured to receive one or more of the presence and absence indications of the first target from the first reader to create a detected insertion signature of the received tool.

Consistent with other embodiments, a tool shaped for installation in a tool recognition assembly is provided. The tool may include an elongated body. The tool may further include one or more targets positioned along the elongated body so as to align with corresponding one or more target readers in the tool recognition assembly when fully inserted in the tool recognition assembly. A first one of the one or more targets may cause the one or more target reader on the tool recognition assembly to detect a presence indication of the first target when the first target is proximate the one or more target reader during an installation of the tool in the tool recognition assembly and an absence indication of the first target when the first target is out of range of the one or more target reader during the installation of the tool in the tool recognition assembly.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 4B is a simplified diagrammatic perspective view of a tool recognition assembly according to some embodiments.

FIGS. 4C-4I are simplified diagrammatic partial cross-sectional views of sources and detectors that can be used to detect the characteristic(s) of tools installed in a tool recognition assembly according to some embodiments.

FIG. 4J is a simplified diagrammatic partial cross-sectional view of various other reader/target sets that can be used to detect the characteristic(s) of tools installed in a tool recognition assembly according to some embodiments.

FIGS. 5M, 5N, 5P, and 5R are simplified diagrammatic side views of tools that are installed in tool recognition assemblies with detectors according to some embodiments.

Figure 5S:
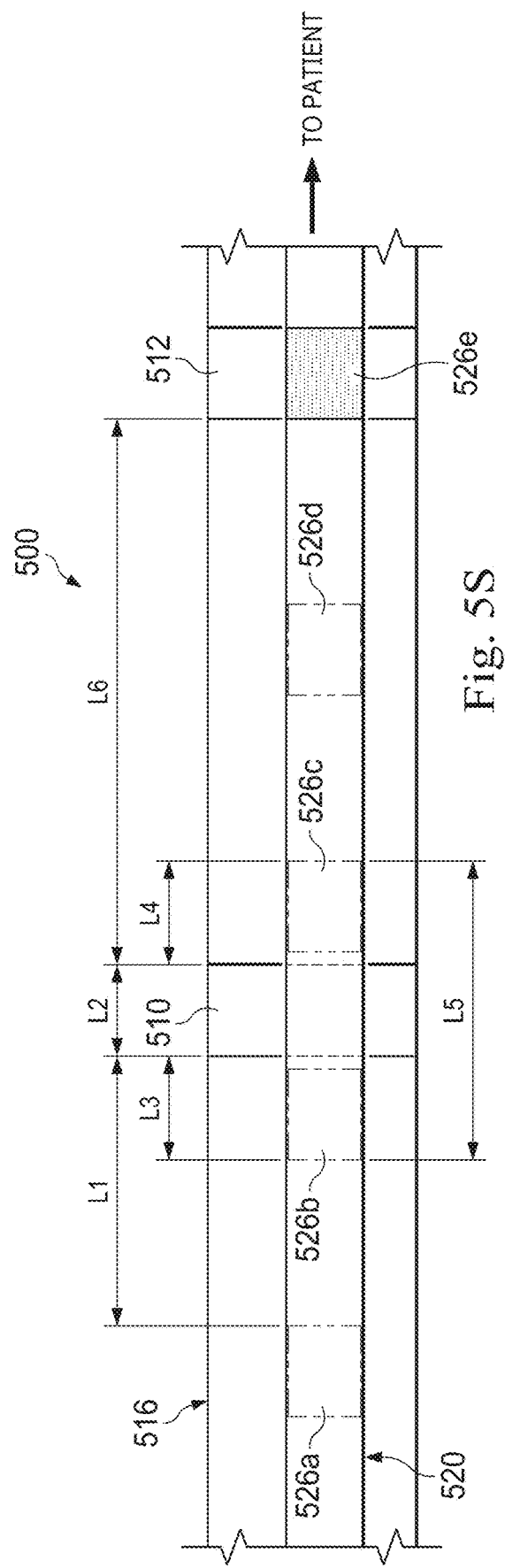
FIGS. 5A-5D are simplified diagrammatic side views of tools installed in tool recognition assemblies according to some embodiments.
FIGS. 5E-5J are simplified diagrammatic side views of a tool as it is installed in a tool recognition assembly according to some embodiments.
FIGS. 5K-5L are simplified diagrammatic side views of another tool as it is installed in a tool recognition assembly according to some embodiments.

FIG. 5S is a simplified diagrammatic side view of another medical instrument as it is installed in a tool recognition assembly according to some embodiments.

Figure 6A:
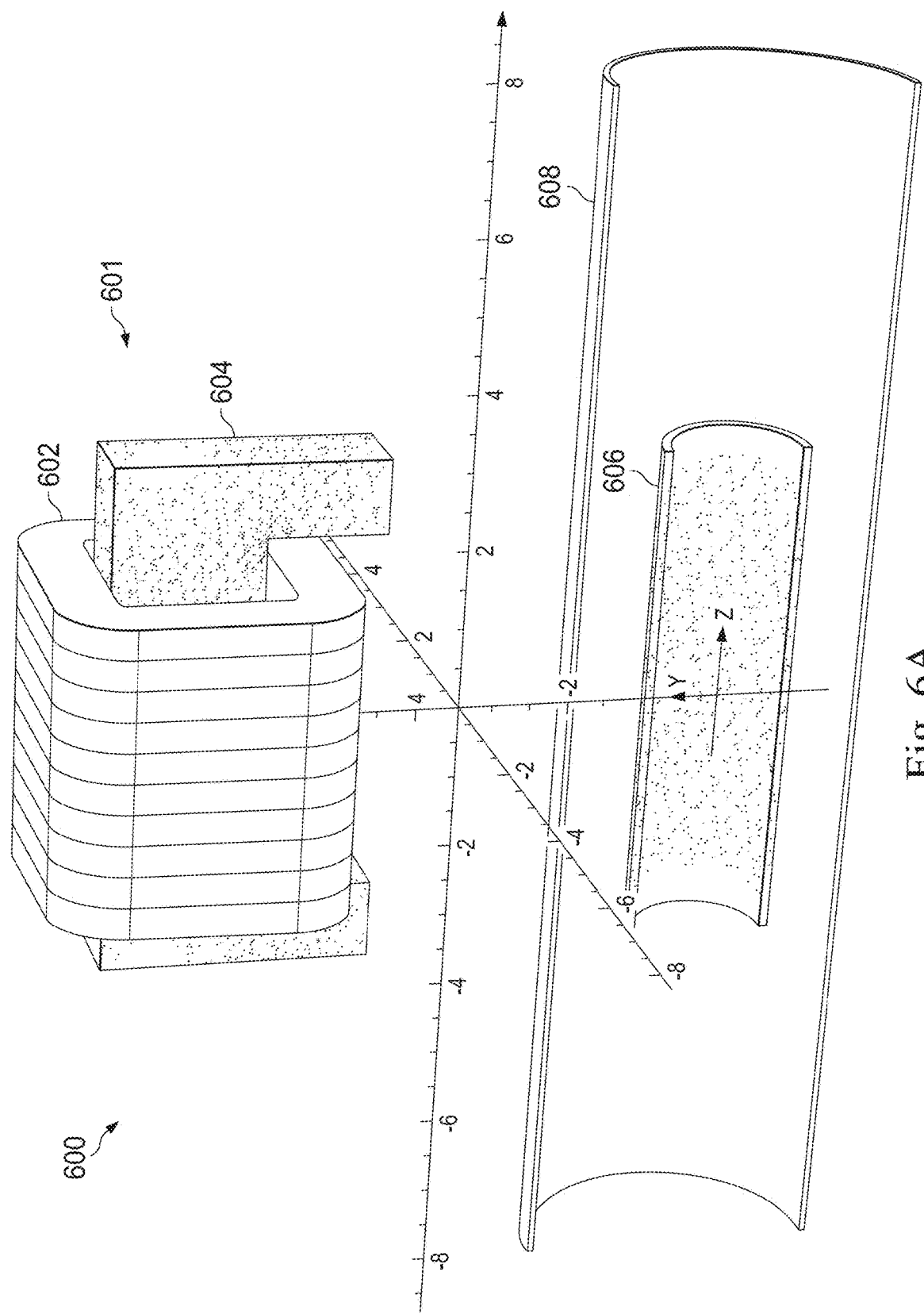
Figure 6B:
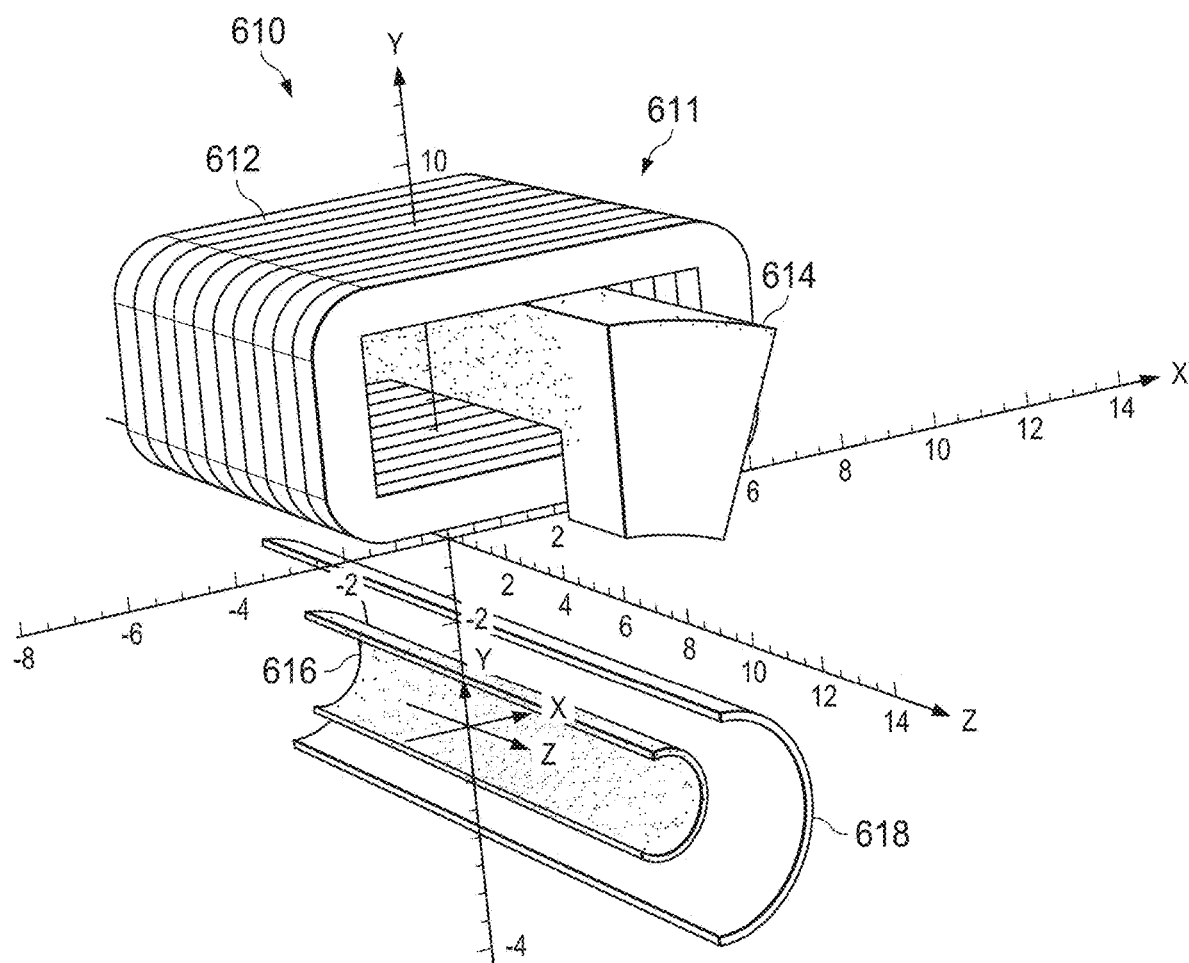
Figure 6C:
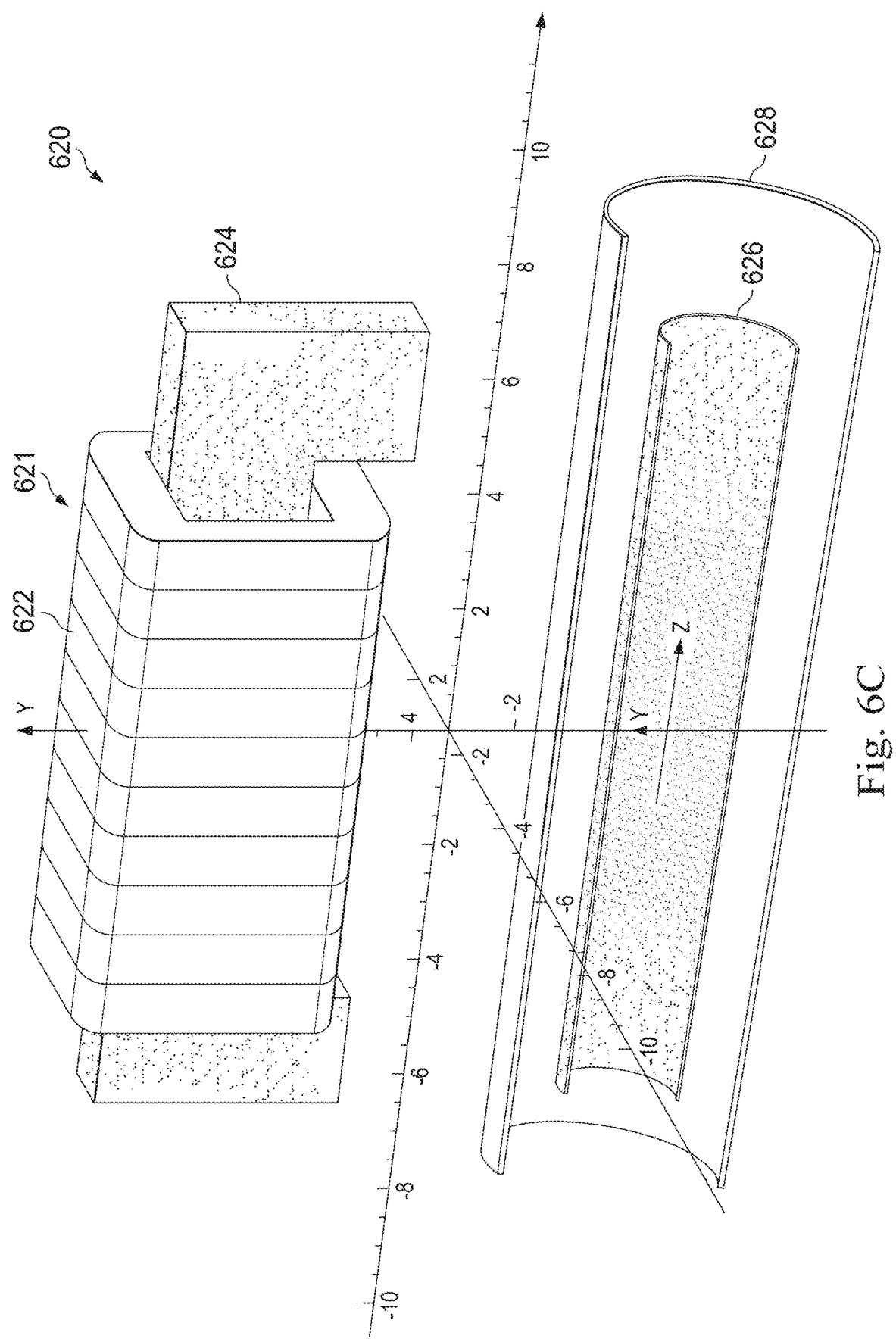

FIGS. 6A-6C are simplified diagrammatic perspective views of reader:target pairs according to some embodiments.

FIG. 6D is a performance graph for a reader:target pairs according to some embodiments.

FIG. 7A is a simplified diagrammatic perspective view of a reader/target pair according to some embodiments.

Figures 7B, 8A:
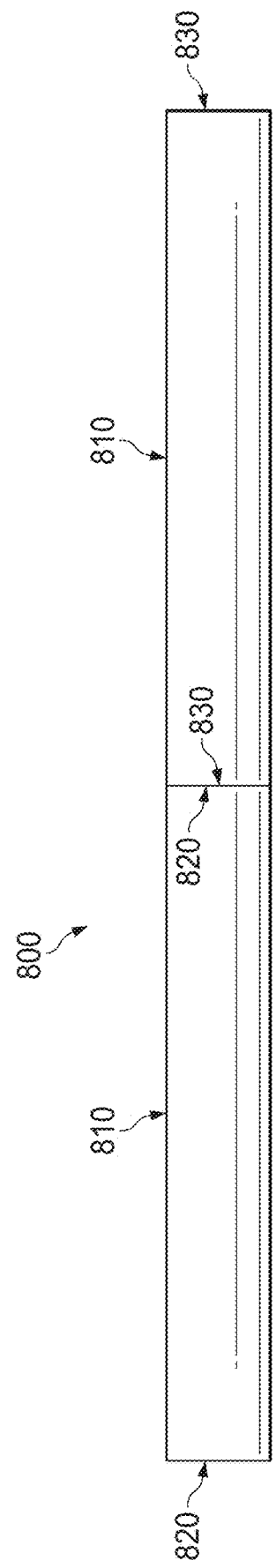

FIG. 7B is a performance table for a plurality of reader: target pairs according to some embodiments.

FIG. 8A is a simplified diagrammatic side view of an elongated target with two sections that can be used with a tool being installed in a tool recognition assembly according to some embodiments.

Figure 8B:
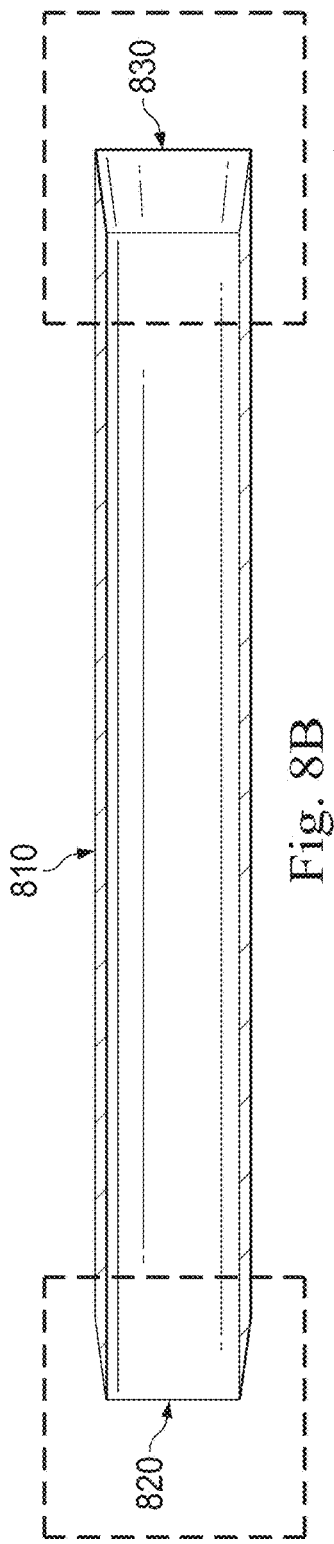
Figure 8D:
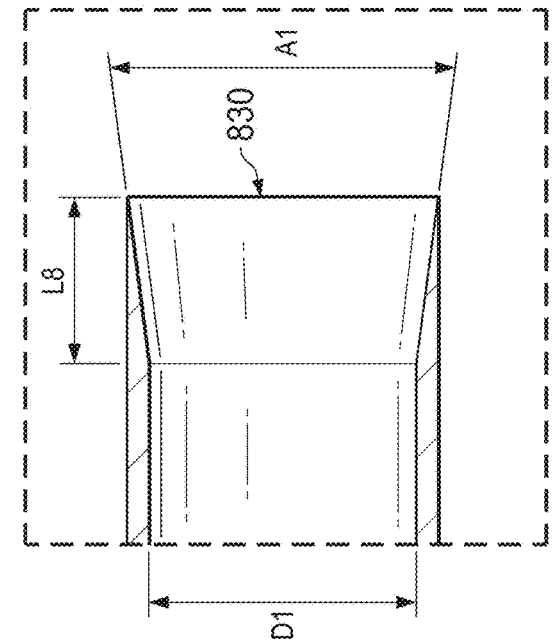
Figure 8C:
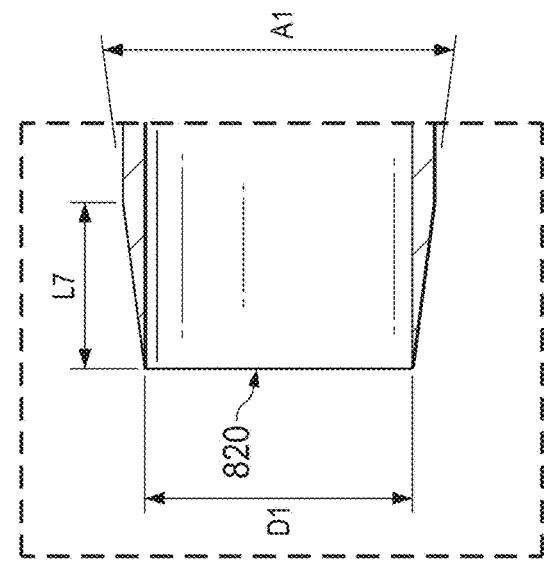

FIGS. 8B-8D are representative partial cross-sectional views of a section of the elongated target shown in FIG. 8A, according to some embodiments.

FIGS. 8E-8F are representative side views of other elongated targets, according to some embodiments.

Figure 9:
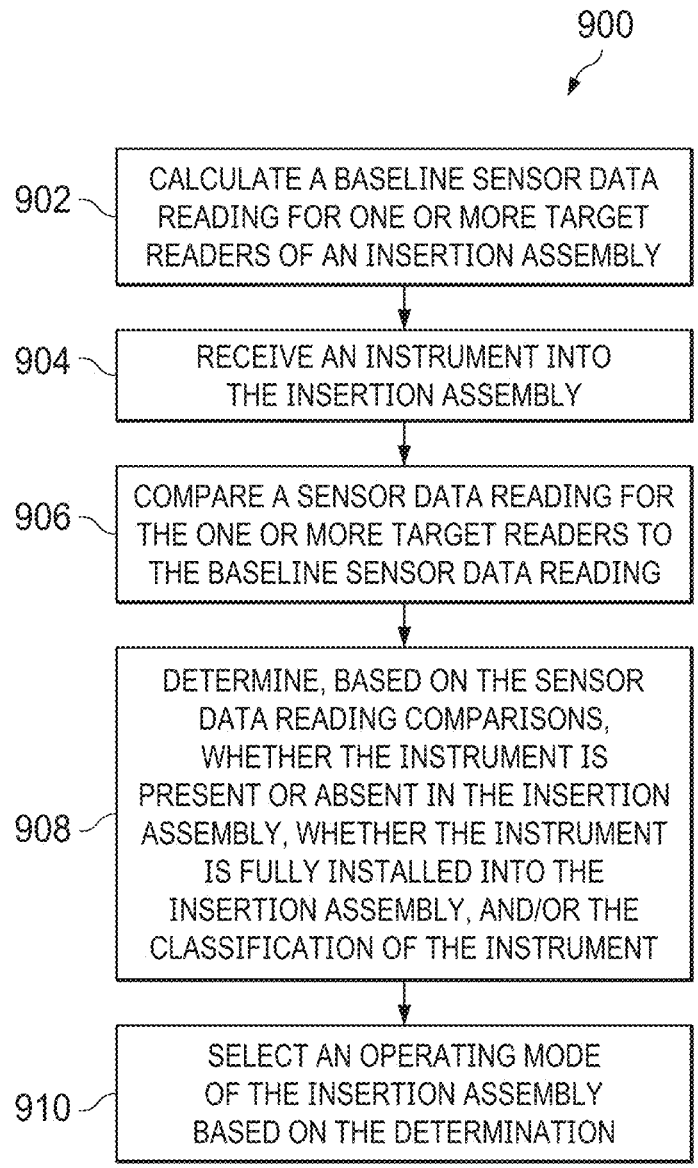

FIG. 9 is a flowchart providing a method for determining a characteristic of a tool according to some embodiments.

Figure 10C:
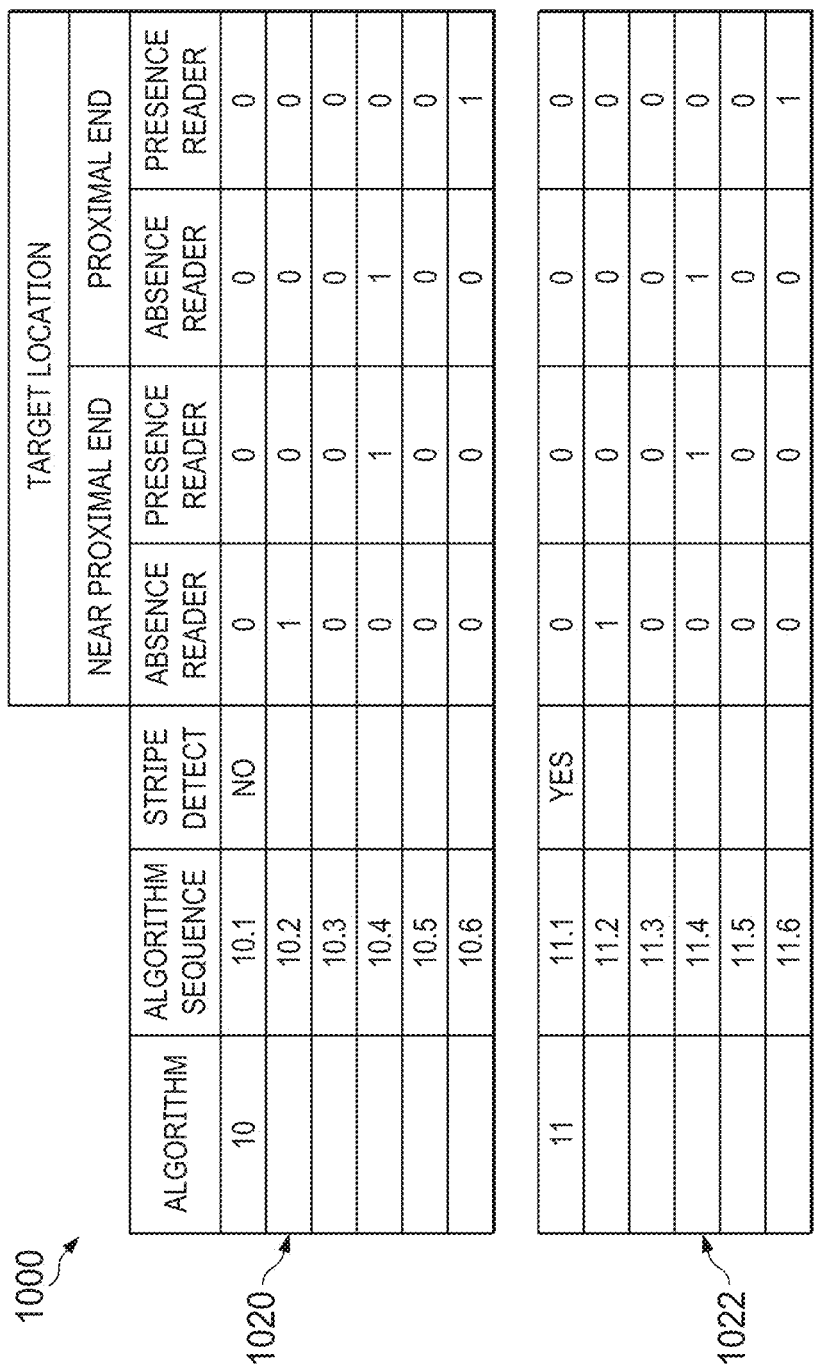

FIGS. 10A-10C are tables showing representative algorithms for detecting a characteristic of a medical instrument installed in a tool recognition assembly, according to some embodiments.

Figure 11:
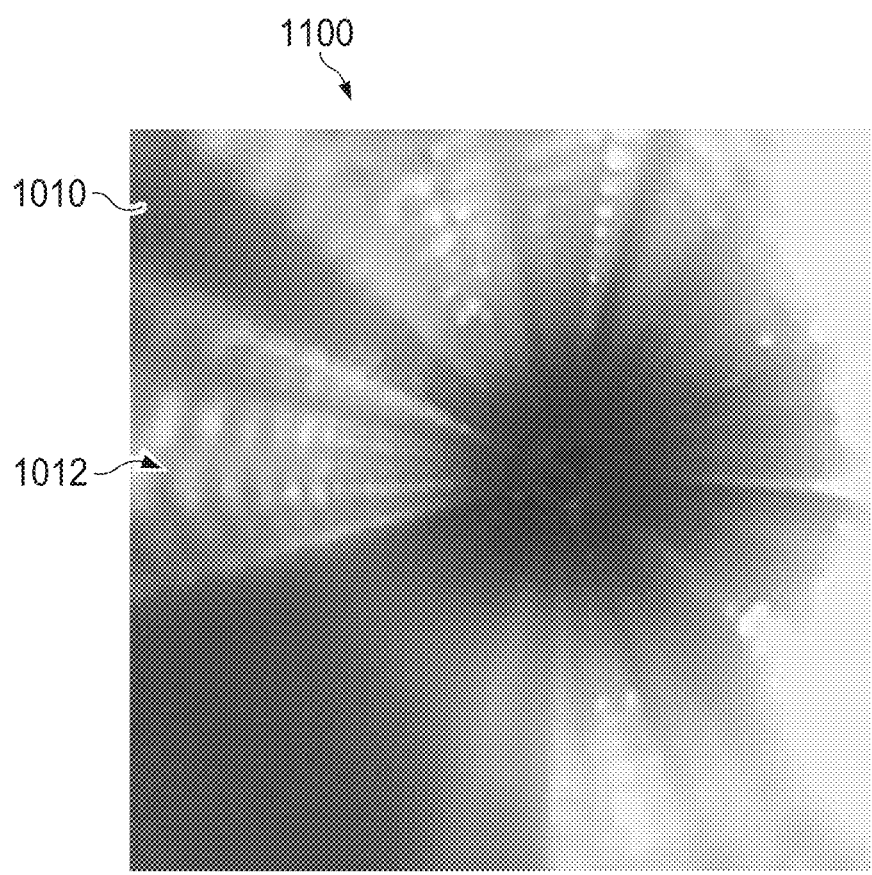

FIG. 11 is a representative image from inside a catheter which can be captured by a camera at a distal end of a medical instrument according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
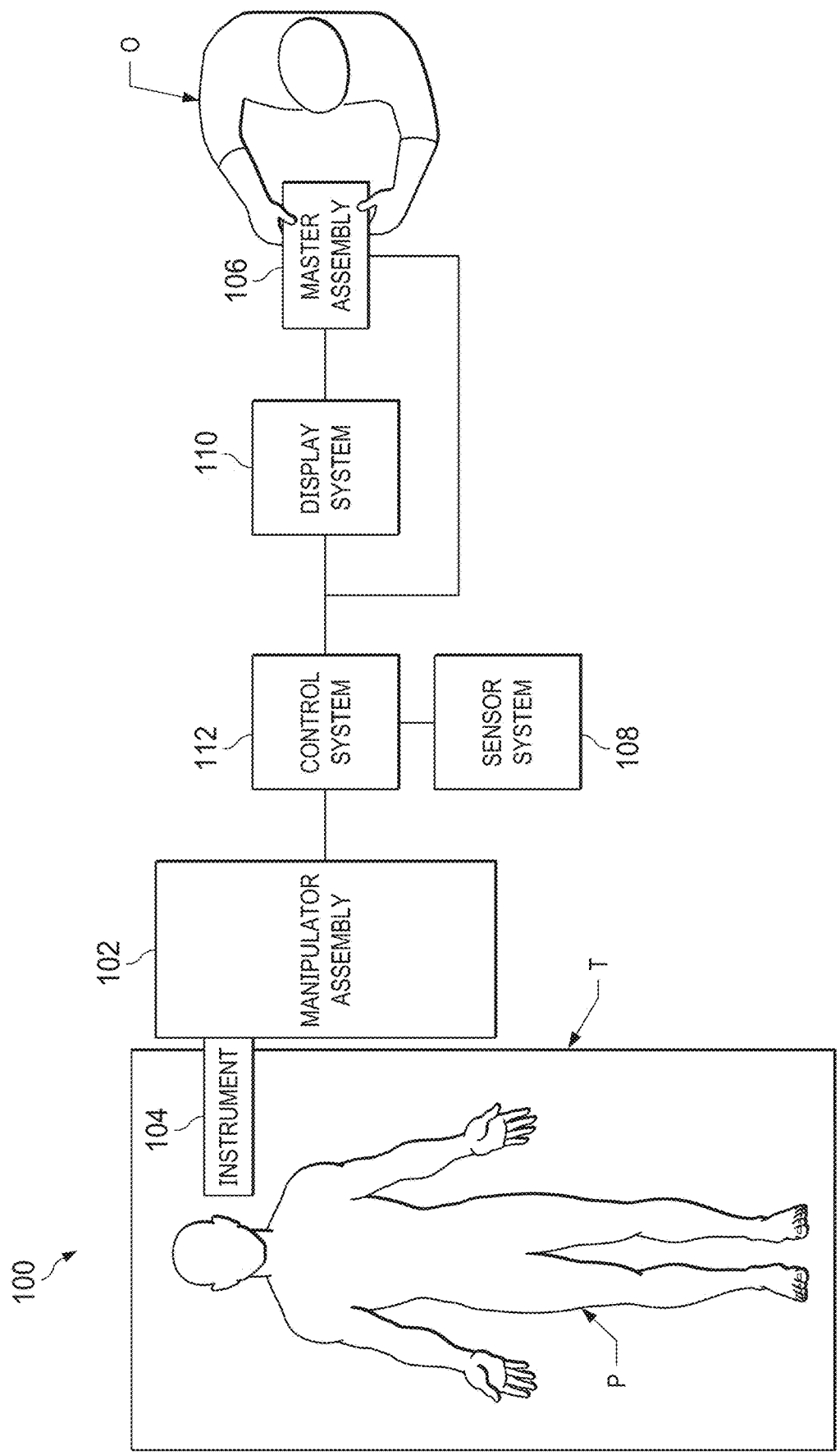
FIG. 1 is a simplified schematic diagram of a teleoperated medical system according to some embodiments.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperated medical systems.

As shown in FIG. 1, medical system 100 generally includes a manipulator assembly 102 for operating a medical instrument 104 in performing various procedures on a patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 is mounted to or near an operating table T. A master assembly 106 allows an operator O (e.g., a surgeon, a clinician, or a physician as illustrated in FIG. 1) to view the interventional site and to control manipulator assembly 102.

Master assembly 106 may be located at an operator console which is usually located in the same room as operating table T, such as at the side of a surgical table on which patient P is located. However, it should be understood that the operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide the operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure), and/or one or more servo controlled links (e.g. one more links that may be controlled in response to commands from the control system), and a manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable portion of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intraoperatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of image-guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory (not shown) and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the control system 112 may include two or more data processing circuits distributed throughout the teleoperated medical system 100 to perform distributed data processing. For example, one portion of the data processing performed by the distributed control system 112 can optionally be performed on or adjacent to manipulator assembly 102, another portion of the data processing can optionally be performed at master assembly 106, and other portions of the data processing can optionally be performed at other data processing circuits. The at least one computer processor or the two or more data processing circuits of control system 112 may execute instructions corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperated medical systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via one or more openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The sensor system 108 may implement one or more electromagnetic (EM) sensor, fiber optic sensors, and/or other sensors to register and display a medical instrument together with preoperatively recorded surgical images. For example, U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such sensor system. Teleoperated medical system 100 may further include optional operations and support systems (not shown) such as illumination systems, steering control systems, irrigation systems, and/or suction systems. In some embodiments, teleoperated medical system 100 may include more than one manipulator assembly and/or more than one master assembly. The total number of teleoperational manipulator assemblies included in the teleoperated medical system will depend on a number of factors including the surgical procedure and the space constraints within the operating room. When implemented as multiple units, master assembly 106 may be collocated or positioned in separate locations. Multiple master assemblies allow more than one operator to control one or more teleoperational manipulator assemblies in various combinations.

Figures 2A, 2B:
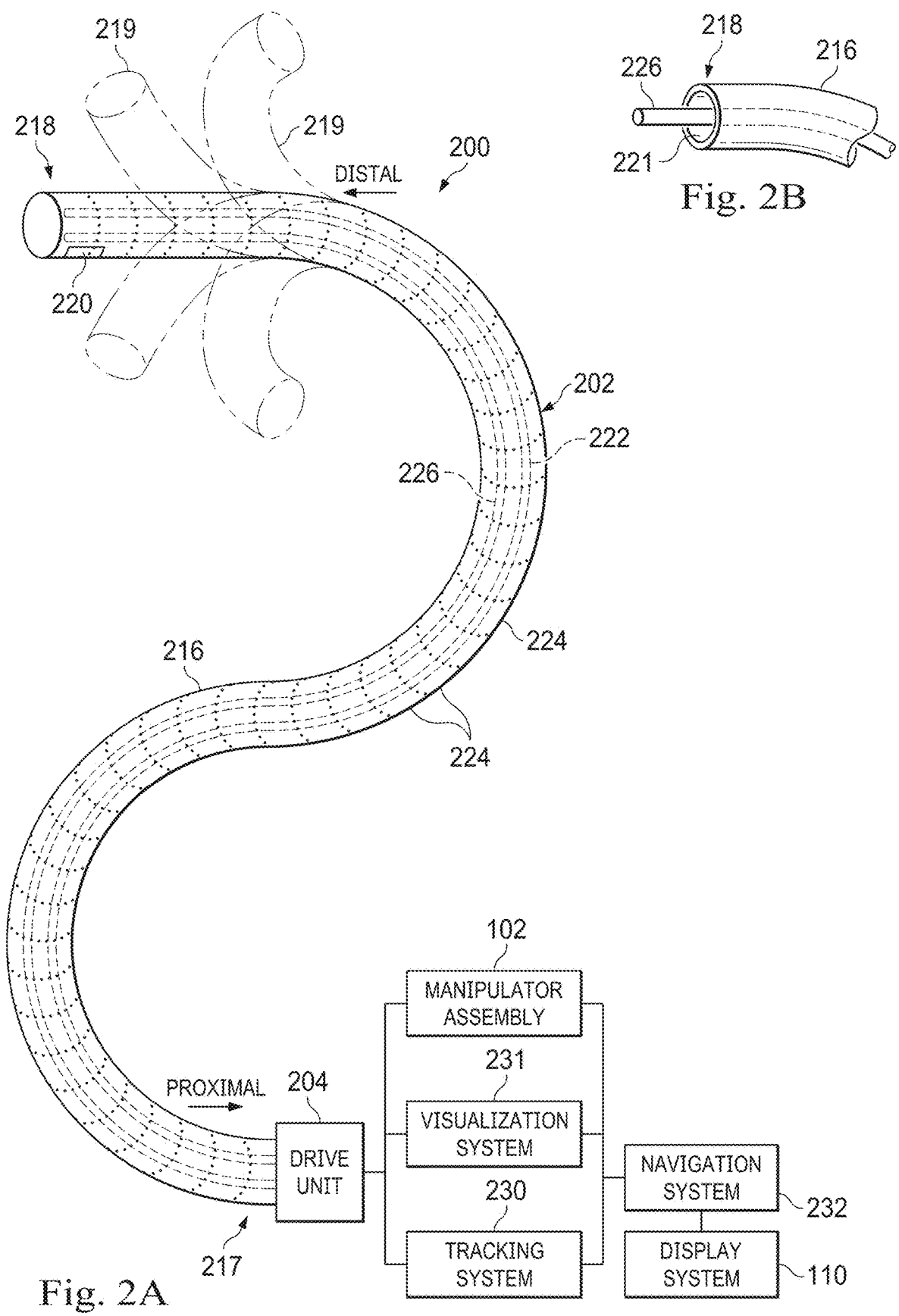
FIG. 2A is a simplified partial-schematic diagram of a medical instrument system according to some embodiments.
FIG. 2B is a simplified diagram of a medical instrument with an extended medical tool according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally, medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or one or more segments 224 along flexible body 216 using one or more sensors and/or imaging devices as described in further detail below. The entire length of flexible body 216, between distal end 218 and proximal end 217, may be effectively divided into segments 224. Tracking system 230 may optionally be implemented as hardware, firmware, software or a combination thereof which interact with or are otherwise executed by one or more computer processors, which may include the at least one processor or the two or more data processing circuits of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 µm. In other embodiments, the dimensions of the optical fiber may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fiber Bend Sensor"), which are all incorporated by reference herein in their entireties.

Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over a given interval of time. In some embodiments, tracking system 230 may optionally and/or additionally track distal end 218 using a position sensor system 220. Position sensor system 220 may be a component of an EM sensor system with position sensor system 220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor system 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical tool 226. FIG. 2B is a simplified diagram of flexible body 216 with medical tool 226 extended according to some embodiments. In some embodiments, medical tool 226 may be used for procedures such as surgery, biopsy, ablation, illumination, irrigation, or suction. Medical tool 226 can be deployed through channel 221 of flexible body 216 and used at a target location within the anatomy. Medical tool 226 may include, for example, image capture probes, biopsy instruments, laser ablation fibers, and/or other surgical, diagnostic, or therapeutic tools. Medical tools may include a single working member such as a scalpel, a blunt blade, an optical fiber, an electrode, and/or the like. Other medical tools may include, for example, forceps, graspers, scissors, clip appliers, and/or the like. Other medical tools may further include electrically activated tools such as electrosurgical electrodes, transducers, sensors, and/or the like. In various embodiments, medical tool 226 is a biopsy instrument, which may be used to remove sample tissue or a sampling of cells from a target anatomic location.

Medical tool 226 may be used with an image capture probe also within flexible body 216. In various embodiments, medical tool 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical tool 226 may itself be the image capture probe. Medical tool 226 may be advanced from the opening of channel 221 to perform the procedure and then retracted back into the channel when the procedure is complete. Medical tool 226 may be removed from proximal end 217 of flexible body 216 or from another optional instrument port (not shown) along flexible body 216.

Medical tool 226 may additionally house cables, linkages, or other actuation controls (not shown) that extend between its proximal and distal ends to controllably the bend distal end of medical tool 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 112 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3A:
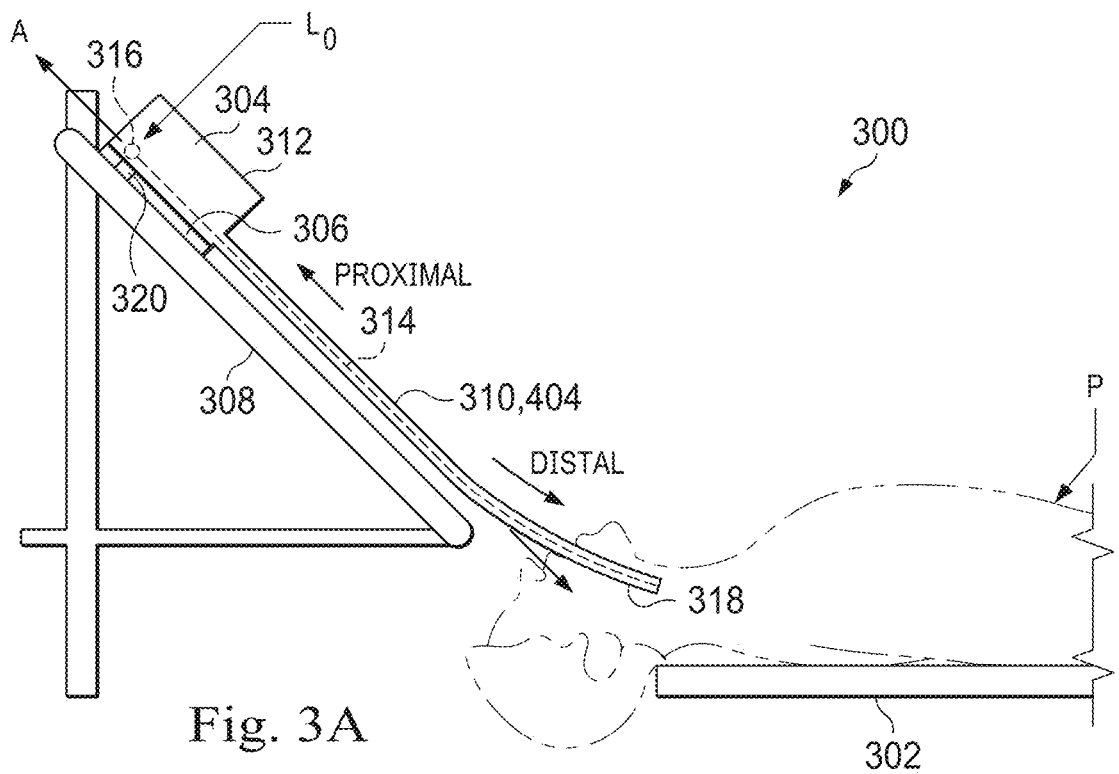
FIGS. 3A and 3B are simplified diagrammatic side views of a patient coordinate space including a medical instrument mounted on an insertion assembly according to some embodiments.
Figure 3B:
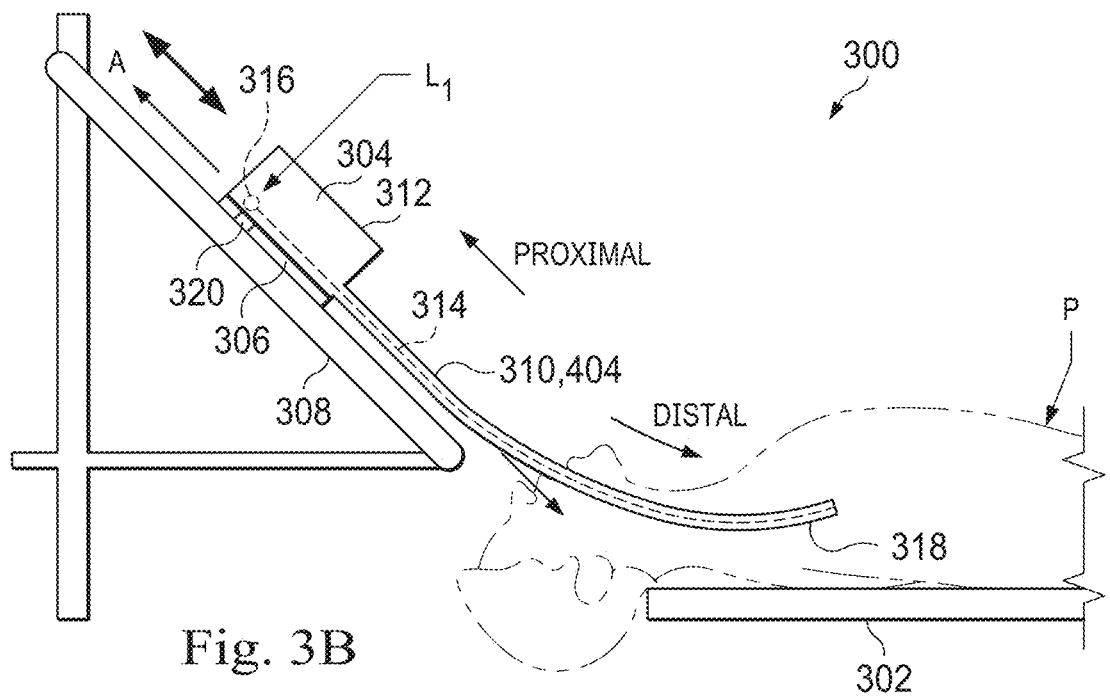

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 (e.g. a medical instrument) can be coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In this position along insertion stage 308, a component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position $L_0$. In some examples, position $L_x$ may further be used as an indicator of the distance or insertion depth to which distal end 318 of elongate device 310 is inserted into the passageways of the anatomy of patient P.

To safely and effectively operate a medical instrument system, medical tools may need to be properly installed, positioned, identified, authenticated and/or otherwise received and recognized when mounted to a system, such as manipulator assembly 102, or inserted into a receiving member, such as medical instrument system 200. As disclosed herein, a tool recognition assembly at the receiving member may be used to detect the presence, proximity, and/or absence of targets on the tool to detect and develop insertion signatures for each inserted tool. Based on the detected and developed insertion signatures, various options for operating the tool or medical instrument system may be enabled or disabled. Although many of the embodiments described herein describe the receiving member as a catheter, the tool recognition systems and methods described are suitable for use with any type of tool and receiving member. In one example described in detail below, the tool recognition assembly may be used to determine a mode of operation based on whether or not a medical tool is fully inserted into a catheter assembly. If, for example the tool is a camera probe, the tool recognition assembly may be used to determine whether the probe is properly seated in a delivery catheter before the catheter may be operated in a driving mode and advanced into the patient. Allowing the catheter to advance blindly without ensuring that the camera probe is properly positioned may cause injury to the patient which can be prevented by use of the tool recognition assembly. Once at a destination, the camera probe may be withdrawn from the catheter to make room for a different medical tool. Withdrawal of the camera probe may leave the physician unable to view the internal body structures to be treated or assessed. Consistent with the teachings of the present disclosure, the tool recognition assembly may detect that the camera has been removed and may enter a safe mode in response. While in the safe mode, one or more functionalities of a control system (e.g., control system 112 in FIG. 1) may be limited or disabled. For example, catheter flexibility and/or the speed at which adjustments to catheter position may be made can be limited. Such limitations are expected to reduce the likelihood of patient injury resulting from blind adjustments to instruments remaining inserted in the patient after withdrawal of the camera. Accordingly, implementation of the teachings of the present disclosure is expected to improve the safety of minimally invasive procedures. A tool recognition assembly may also be used to recognize counterfeit, competitor, or otherwise unauthorized devices or tools (such as a device or tool manufactured by a competitor or an unauthorized manufacturer). A tool recognition assembly may also be used to identify tool types (e.g. needles, ablation tools, cutter, graspers, etc.), and based on the recognition of tool type, control mode alternations or tool behavior modifications may be implemented.

Figure 4A:
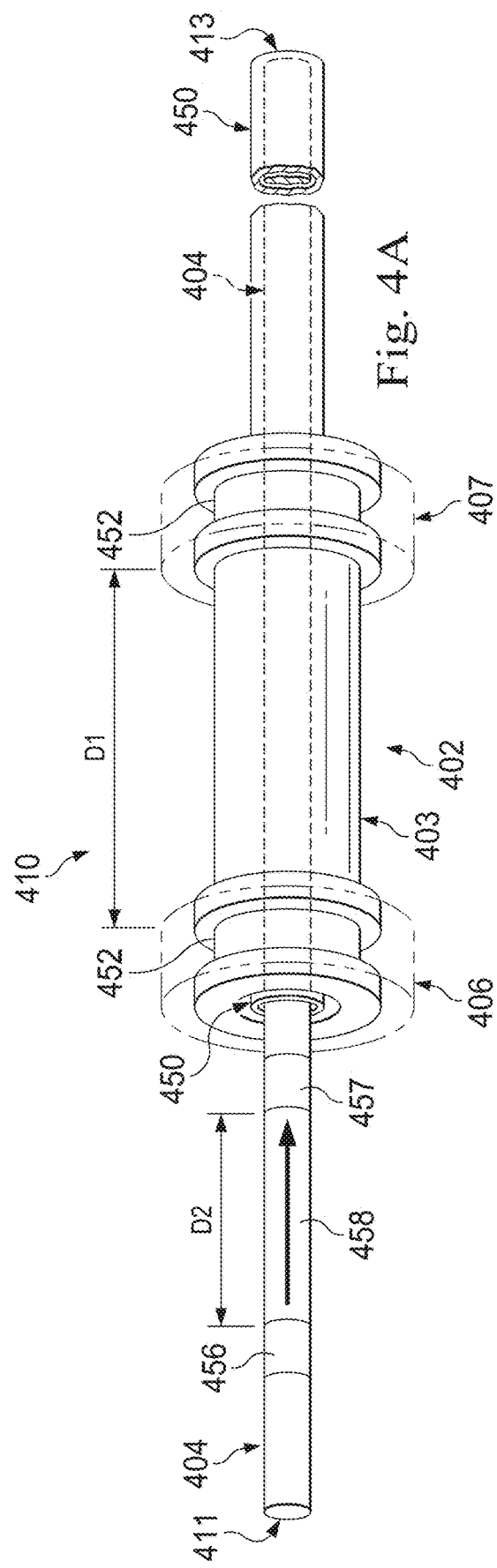
FIG. 4A is a simplified diagrammatic perspective view of a tool recognition assembly with a tool inserted in the tool recognition assembly according to some embodiments.

FIG. 4A illustrates an exemplary tool recognition system implemented as a tool recognition assembly 410 into which a receiving member 450 (e.g., a catheter, flexible body 216, or elongate device 310) may extend. It should be understood that the receiving member 450 (e.g. a catheter) can also be inserted through the tool recognition assembly 410 and insertion signatures can be generated as the receiving member 450 and/or tool 404 are inserted. In this embodiment the tool recognition assembly 410 includes a reader mount 402. In various embodiments, the reader mount 402 may be mounted to a manipulator assembly (e.g., manipulator assembly 102) as described in greater detail in FIG. 4B. The tool recognition assembly 410 can incorporate one or more target readers configured to detect one or more targets on a tool and/or catheter. In the example shown in FIG. 4A, a target reader 406 is coupled to a proximal end of the reader mount 402, and another target reader 407 is coupled to a distal end of the reader mount. In this embodiment, the reader mount 402 is shown as a cylinder or bobbin with channels 452 separated by an elongated body 403. The reader mount 402 may be formed of a plastic, a ceramic, or another type of material that minimizes interference with the target readers 406, 407. Each of the target readers 406, 407 extends into a corresponding one of the channels 452 to couple to the reader mount 402. The target readers 406, 407 are separated by a distance D1. The target readers 406 may comprise an inductive sensor (e.g., an inductor or inductive coil that detects a change in inductance caused by ferromagnetic and conductive properties of a material), a capacitive sensor, a Hall effect sensor, a photogate sensor, an optical sensor, a magnetic switch, a barcode scanner, a radio frequency identification (RFID) scanner, a relative position sensor, or combinations thereof that are capable of reading corresponding one or more targets on a tool to be inserted into the receiving member 450 of the tool recognition assembly 410. Any combination of different types of target readers may be implemented in the tool recognition assembly 410.

An exemplary tool 404 (e.g., a tool 226) and/or receiving member 450 can include one or more targets that can be read by the one or more target readers 406, 407 on the tool recognition assembly 410. For the example shown in FIG. 4A, the tool 404 includes a target 456 and a target 457 separated by a distance D2. The distance D2 between the targets 456, 457 on the tool can have a predetermined relationship to the distance D1 between the target readers 406, 407. The tool 404 is sized for insertion into the reader mount 402 and receiving member 450 along an insertion trajectory path 458. The tool 404 may extend through the reader mount 402 and the receiving member 450. The receiving member 450 may also be configured to extend through the reader mount 402 with one or more targets (which may be similar to targets 456, 457) thereby allowing the target readers 406, 407 to detect the presence of the targets on both of the receiving member 450 and the tool 404. The receiving member 450 may be configured and/or constructed to minimize any interference between the target readers 406, 407 and the targets 456, 457. However, the receiving member 450 may be configured to increase inductance readings at the target readers by a predetermined amount to indicate the presence of the receiving member 450 (e.g. a catheter). Various techniques can be implemented to minimize the interference between the target readers 406, 407. For example, the target readers 406, 407 can perform corresponding tasks at different times as a form of time-division multiplexing. As described in greater detail below, the presence, proximity, and/or absence of the targets 456, 457 may be sensed, detected, or otherwise recognized by the target readers 406, 407. For example, the targets may comprise a ferromagnetic material (e.g., a metal cylinder, a metallic coating), one or more apertures, a surface or material with varied optical absorption characteristics, a barcode, an RFID chip, or combinations thereof that may be sensed, detected, or otherwise recognized by a target reader. In one example, a target reader may detect the presence of a target by detecting an inductance and/or a change in inductance when the target is placed in proximity to a target reader. It should be understood that the discussion regarding targets on a tool 404 may also be applicable to targets on a receiving member 450 (e.g. a catheter). When the receiving member 450 is inserted into the recognition assembly 410, an insertion signature can be created for the receiving member 450, and when the tool 404 is inserted into the recognition assembly 410, an insertion signature can be created for the tool 404. Inductance readings, when both the tool 404 and receiving member 450 are inserted into the recognition assembly 410, may be higher than individual readings of targets on either the receiving member 450 or the tool 404. This can be used to determine the presence and/or absence of the receiving member 450 and the tool 404 in some embodiments.

In the embodiment of FIG. 4A, the reader mount 402 includes two channels 452 and may therefore accommodate two target readers 406, 407—one in each channel 452. In alternative embodiments, a reader mount may comprise any number of channels and may accommodate any number of target readers. For example, the reader mount 402 may comprise a single channel 452, three channels 452, four channels 452, or some other number of channels 452 and may accommodate as many target readers as channels. In some embodiments, the reader mount 402 may lack channels but may nevertheless accommodate any number of target readers via other coupling mechanisms. In some embodiments, there may be fewer target readers than channels, where some channels can be empty. In some embodiments, the reader mount may have a non-cylindrical shape and may be any type of bracket or mounting mechanism for mounting one or more target readers in a location proximate to the receiving member. In some embodiments, the receiving member may have an open channel or any shape for receiving and allowing longitudinal movement of a tool. In some embodiments, the reader mount 402 (or regions of the reader mount) may be considered to be an element or elements of one or more of the target readers 406, 407 in that the reader mount 402 may play a role in the detection of one or more targets on the tool 404. For example, channels 452 may be of a different composition than the rest of the reader mount 402 and may facilitate detection of one or more targets on the tool 404.

In the embodiment of FIG. 4A, the tool 404 may include any number of targets positioned along the length of the tool. For example, the tool may include a single target, three targets, or some other number of targets. There may be a different number of targets than there are target readers. For example, there may be three target readers in the tool recognition assembly with two targets on the tool, one target reader in the tool recognition assembly with two targets on the tool, or two target readers in the tool recognition assembly with one target on the tool.

The targets 456, 457 may be positioned on the tool 404 such that they will be detected by the target readers 406, 407 when the tool is at least partially installed (or inserted) into the receiving member 450. In the embodiment of FIG. 4A, the targets 456, 457 may be mounted near a proximal end 411 of the tool 404, and the target readers 406, 407 may be mounted (e.g. to a manipulator assembly 102) near a proximal end of the receiving member 450. The proximal locations of the target readers 406, 407 relative to the receiving member 450 and the targets 456, 457 on the tool 404 provide a configuration that may allow the tool recognition assembly 410 to recognize that the tool 404 is fully extended into the receiving member 450. In alternative embodiments, the targets 456, 457 may be positioned at other locations along the tool 404, and the target readers 406, 407 may be positioned at other locations along the receiving member 450. For example, distal locations may be suitable in some embodiments. In other alternative embodiments, the reader mount may be omitted and the target readers may be coupled to or integrated into the receiving member itself.

The target readers 406, 407 may be in communication with a computing system configured to process data from the target readers (e.g., changes in inductance, changes in a magnetic field, changes in intensity of light, changes in colors of light, etc.). The computing system may be, for example, a component (e.g. control system 112) of a teleoperated medical system. The computing system may receive the data from the target readers 406, 407 periodically at regular or irregular intervals or continuously. For example, the target readers 406, 407 may communicate the data to the computing system responsive to a change in the data sensed by the target readers (e.g., changes in inductance, changes in resistance, changes in capacitance, changes in a magnetic field, changes in intensity of light, changes in colors of light, etc.) In another example, the data from the target readers are regularly communicated to the computing device, either periodically or continuously, and the computing device is tasked with determining when the data has changed. The computing system may comprise one or more processors configured to process the data received from the target readers 406, 407 including detecting changes in the sensed data received from the target readers 406, 407.

As described, the tool recognition assembly 410 may be configured to detect whether or not the tool 404 is fully inserted into the receiving member 450. The tool recognition assembly 410 may also be configured to detect whether or not the receiving member 450 (such as a catheter) is fully inserted into the patient. The tool 404 may be considered fully inserted when the tool 404 is inserted to such a degree as to permit the tool 404 being used within the body of a patient, inserted to such a degree that a distal end 413 of the tool 404 is within a certain distance of a distal end of the receiving member 450, inserted to such a degree that the tool 404 extends through the reader mount 402, inserted to such a degree that a distal portion of the tool 404 extends a relative distance past a distal end of the receiving member, or combinations thereof. In some embodiments, the tool 404 may be considered fully inserted when it is inserted coaxially through the receiving member 450 such that the distal end 413 of the tool is flush with a distal end of the receiving member.

Detecting whether or not the tool 404 is fully inserted (or otherwise acceptably positioned for operation) relative to the receiving member 450 may comprise comparing readings from the target readers 406, 407 to a pre-established model insertion signature. As used herein, "pre-established model insertion signatures" or "model insertion signatures" refer to insertion signatures that have been generated by a modeling software application, inputs from a user interface, measurements logged during an installation of another tool, etc. that have been established to represent positions of a tool while being inserted in a receiving member 450. The tool 404 may be determined to be acceptably positioned for operation and thus fully inserted when readings from the target readers 406, 407 match the model insertion signature indicating a fully inserted tool and may be determined not to be acceptably positioned for operation and thus not fully inserted when readings from the target readers 406, 407 do not match the model insertion signature indicating a fully inserted tool. The readings from target readers 406, 407 that correspond to the model insertion signature indicating a fully inserted tool can include various characteristics, such as a sequence of target readings by the target readers 406 and 407, a threshold duration of target readings by the target readers 406 and 407, various threshold values, ratios of values, or a combination of sequence, threshold duration, threshold values, and/or ratios of values.

Various properties of the readings detected by the target readers 406 and 407 can affect the determination of whether a particular reading from the target readers 406 and 407 can contribute to a detected insertion signature. For example, the strength (i.e. threshold), duration, multiple thresholds, or a combination of strength, duration, and multiple thresholds of the readings can be used to determine when a target is detected by the target readers 406 and 407. Additionally or alternatively, derivative properties of the signals read by the target readers 406, 407 such as the rate of change of the signal (e.g., slope), may be used in the determination of a detected insertion signature. When an inductive element is used as the target, the target reader 406, 407 can produce an inductance measurement signal that varies as the target 456, 457 approaches the target reader, as the target 456, 457 is proximate the target reader 406, 407, and as the target 456, 457 moves away from the target reader 406, 407. An amplitude (or strength) of the inductance measurement can indicate a presence of a target 456, 457 in a detection zone of the target reader 406, 407. The strength (i.e. amplitude threshold) of the inductance measurement, duration of the inductance measurement, multiple thresholds, and a combination of strength, duration of the inductance measurement, and multiple thresholds read by the target readers 406 and 407 can be used to determine whether the target has been detected in the detection zone of the target reader 406, 407. Additionally, a slope, inductance ratios, and/or other derivatives of the inductance measurement signal can be used to indicate a presence or an absence of the target in the detection zone of a target reader 406, 407. One way to represent the target detection and non-detection respectively is to use a binary (e.g., '1' or '0') signal to indicate the presence or absence of a target in the detection zone of the respective target reader 406, 407 as determined by the strength, duration, slope, ratios, and combinations thereof of the inductance measurement signal as well as other derivatives of the inductance measurement signal from the target readers 406 and 407.

For example, the presence (which can be indicated by a '1') and/or absence (which can be indicated by a '0') of a target in the detection zone of the respective target reader 406, 407 can be determined by ratios of inductance measurements. When ratios are used to indicate presence or absence of a target, a baseline inductance is measured and then used to compare to other inductance measurements before, during and/or after insertion of a catheter and/or tool in the tool recognition assembly 410. The baseline inductance measurement can be collected from a baseline target reader that has no catheter or probe inserted through it and/or the baseline inductance reading can be collected from a target reader 406, 407 when there is no catheter or probe inserted through it. A ratio for inductance measurements from the target readers 406, 407 can be calculated by the equation (1) below:

$$K = \frac{L_{measurement}}{L_{baseline}}$$

where $L_{baseline}$ is the inductance baseline, $L_{measurement}$ is an inductance measurement from a target reader, and K is the ratio between the inductance measurement and the inductance baseline.

When the ratio K is determined, the value may indicate the presence and/or absence of the receiving member 450 and/or tool(s) 404. Table 1 below indicates possible inductance ratio values that may be determined from one or more of the target readers 406, 407 and possible configurations that may be indicated by the values.

TABLE 1

| Inductance Ratio (K) | Target on Catheter | Target on Tool #1 | Target on Tool #2 | Target on Tool #3 |
|---|---|---|---|---|
| 0.99-1.01 | Absent (0) | Absent (0) | Absent (0) | Absent (0) |
| 1.02-1.04 | Absent (0) | Present (1) | Absent (0) | Absent (0) |
| 1.04-1.06 | Present (1) | Absent (0) | Absent (0) | Absent (0) |
| 1.06-1.08 | Present (1) | Present (1) | Absent (0) | Absent (0) |
| 1.08-1.10 | Present (1) | Present (1) | Present (1) | Absent (0) |
| 1.10-1.12 | Present (1) | Present (1) | Present (1) | Present (1) |
| >1.12 | ?? | ?? | ?? | ?? |

In this example, if the inductance ratio is within a range from 0.99 to 1.01, this may indicate that neither the receiving member 450 nor any tool 404 has a target 456, 457 in the detection zone of a target reader 406, 407 (i.e. absent "0"). If the inductance ratio is within a range from 1.02 to 1.04, this may indicate that a tool #1 has a target in the detection zone of a target reader (i.e. present "1") while the catheter, tool #2, and tool #3 do not have a target in the detection zone of a target reader (i.e. absent "0"). If the inductance ratio is within a range from 1.04 to 1.06, this may indicate that a catheter has a target in the detection zone of a target reader (i.e. present "1") while tool #1, tool #2, and tool #3 do not have a target in the detection zone of a target reader (i.e. absent "0"). If the inductance ratio is within a range from 1.06 to 1.08, this may indicate that a catheter and a tool #1 (e.g., a vision probe) each have a target in the detection zone of a target reader (i.e. present "1") while tool #2 and tool #3 do not have a target in the detection zone of a target reader (i.e. absent "0"). If the inductance ratio is within a range from 1.08 to 1.10, this may indicate that a catheter, a tool #1, and a tool #2 each have a target in the detection zone of a target reader (i.e. present "1") while tool #3 does not have a target in the detection zone of a target reader (i.e. absent "0"). If the inductance ratio is within a range from 1.10 to 1.12, this may indicate that a catheter, tool #1, tool #2, and tool #3 each have a target in the detection zone of a target reader (i.e. present "1"). If the inductance ratio is above 1.12, this may indicate that the configuration of catheter and/or tools in the tool recognition assembly 410 is unknown. This may indicate that an unidentified tool or catheter is present in the tool recognition assembly 410. Determining inductance ratios K can minimize impacts of inductance variations between various target readers due to use, manufacturing, material variations, environmental conditions, etc. Based upon the detected configuration of catheter and tools, the system may determine a mode of operation or enable/disable behaviors.

When two target readers 406, 407 are used in combination, as shown in FIG. 4A, the model insertion signature indicating a fully inserted tool may include a specific sequence of measurements read from the proximal target reader 406 and the distal target reader 407 as the tool 404 (and/or catheter) is inserted. In addition, the measurements read from the target readers 406 and 407 can depend on the number of targets present on the tool 404. For a single target implementation, such as the target 457, the distal target reader 407 has a positive reading or presence reading for target detection while the proximal target reader 406 has a negative reading or absence reading for target detection. For the single target implementation, the target 457 may be read first by the proximal target reader 406 and then by the distal target reader 407 when the tool 404 is fully inserted into receiving member 450. Accordingly, an exemplary sequence of target detections associated with a fully inserted tool 404 having a single target 457 can include: (1) both the proximal target reader 406 and the distal target reader 407 not detecting the target 457 (combined '0', '0' readings from the two target readers 406, 407 respectively); (2) the proximal target reader 406 detecting the target 457 while the distal target reader 407 not detecting the target 457 (combined '1', '0' readings from the two target readers 406, 407 respectively); and then (3) the proximal target reader 406 no longer detecting the target 457 while the distal target reader 407 detecting the target 457 (combined '0', '1' readings from the two target readers).

When a second target (e.g., target 456) is included on the tool 404, the sequence of target detection changes to accommodate the second target. For example, when the target 456, is included on the tool in addition to the target 457, the target 456 may be read or detected only by the proximal target reader 406. In some embodiments, a fully inserted tool 440 may be indicated when the target 456 is read or detected by the distal target reader 407. For example, if the target 456 is located distally further from the proximal end 411, a fully inserted tool may be associated with a proximal target reader 406 having a '0' reading and the distal target reader 407 having a '1' reading (corresponding to the detection of target 457 by the distal target reader).

In some embodiments, the tool 404 may not be considered fully inserted (or installed) into the receiving member 450 unless the target readers 406, 407 generate readings that match the model insertion signature for a predetermined minimum duration of time, e.g., a fraction of one second, one second, two seconds, three seconds, four seconds, five seconds, ten seconds, etc. Detections of the model insertion signature for lesser durations than specified to indicate a fully inserted tool may be disregarded. It should also be understood that the contents of the model insertion signature can be a timed sequence of events with various time delays between the sequences of events. The readings from the target readers 406, 407 can be determined to match a given model insertion signature when the timing of the events as well as the type of events match between the readings from the target readers 406, 407 and the model insertion signature.

Establishing a model insertion signature indicating a fully inserted tool may reduce the incidence of false positives caused by a partially inserted tool. For example, when the tool 404 is partially inserted into the reader mount 402, the distal target reader 407 can have a positive reading for target detection of the target 457 (e.g., a reading of '1') while the proximal target reader 406 has a negative reading for target detection of the target 457 (e.g., a reading of '0'). As used herein, a "positive" reading refers to a positive detection that a target is in a detection zone of a target reader. Therefore, the "positive" reading can be a received signal strength of the target reader being above a threshold, a ratio of the received signal being within a predetermined range, a slope of the received signal being in an acceptable range that indicates a presence of the target, an integration value of the receive signal being within an acceptable range, a strength threshold of the received signal is held for a pre-determined duration of time, or combinations of these, as well as other signal attributes that indicate the presence of the target in the target reader detection zone. As used herein, a "negative" reading refers to a detection that a target is not in a detection zone of a target reader. Therefore, the "negative" reading can be a received signal strength of the target reader being below a threshold, a ratio of the received signal being within a predetermined range, a slope of the received signal being outside an acceptable range that indicates a target is not present in the detection zone, an integration value of the receive signal being in a range that indicates absence of the target, a strength threshold of the received signal is not held for a pre-determined duration of time, or combinations of these, as well as other signal attributes that indicate that the target is not in the target reader detection zone.

The model insertion signature specified above is similarly expected to reduce the incidence of false positives arising from insertion of a foreign object, such as an elongate item of a composition similar to the target on a tool such that both the proximal target reader 406 and the distal target reader 407 exhibit positive readings for target detection. For example, when inductive sensors are implemented in the target readers 406, 407, an iron bar inserted into the tool recognition assembly 410 past the target readers 406, 407 would likely cause both target readers 406 to read positive for target detection. The model insertion signature specified above would prevent such a double positive from being interpreted as detection of the tool 404.

Despite the potential for false positives, the model insertion signature may in some cases correspond to all of the target readers indicating the presence of a target on a tool. Such a model insertion signature may permit more cost efficient target readers or a lower number of target readers (e.g., a single target reader) to be used.

In some cases, more than one model insertion signature may indicate that the tool is acceptably positioned in the receiving member. Accordingly, in some cases, readings from the target readers may be compared to more than one pre-established model insertion signature. Generally, increasing the number of target readers increases the number of model insertion signatures possible. By way of example, and without limitation, several exemplary model insertion signatures are described in greater detail herein below.

In addition to determining whether or not the tool is acceptably positioned for operation, the tool recognition assembly 410 may be used to classify the tool 404. For example, the detected insertion signature obtained from the readings from the target readers may be compared to a plurality of model insertion signatures that may be associated with different types of tools. Thus, different tool types may feature different numbers or types of targets to be read by target readers. Certain readings characterizing a corresponding tool type may also be included in a model insertion signature for indicating that the tool is acceptably positioned for operation (e.g., fully inserted) in the receiving member 450. In some cases, different materials may be used for targets in different medical tools. Accordingly, the tool may be classified not only by a detected insertion signature obtained based on the readings from the target readers but also by a variation of the sensed data. For example, targets in different tools may provide additional and different sensed data as detected by the target readers.

The tool recognition assembly 410 may be further used to determine a mode of operation based on one or both of insertion/position status and instrument type. For example, if the tool is determined to be fully inserted, the control system 112 may enter a general operation mode in which no limitations are placed on use of the various functionalities of the manipulator assembly 102. If, however, the tool is determined to be not fully inserted, then the control system 112 may enter a safe mode including one or more restrictions on the operation of the manipulator assembly 102. Examples of restrictions include limiting an operating speed (e.g., a speed of insertion of a catheter), limiting catheter flexibility, increasing catheter flexibility, limiting the speed at which adjustments to the catheter may be made, and disabling certain functionalities such as a lens cleaning functionality which can use puffs of air or other fluids to effect the cleaning. In some cases, functionalities may be activated or disabled on an instrument by instrument basis. For example, certain functionalities, e.g., a lens cleaning functionality, may be activated when it is determined that the tool is fully inserted into the receiving member (e.g., a catheter) and comprises an endoscope or vision probe. Those same functionalities may be disabled when the tool is fully inserted but instead comprises an ablation tool. In other embodiments, the detected absence of a vision probe may cause illumination sources to be dimmed or deactivated.

Additionally, the control system 112 may control image collection of an imaging tool depending upon whether the tool is fully inserted, partially inserted, or not inserted at all into the receiving member. For example, when the tool is not inserted, the control system 112 may control the imaging tool to collect images at a slow rate (e.g. one image per second or slower) to confirm that the tool has not yet been inserted, while minimizing image processing prior to insertion of the tool. When the tool is at least partially inserted in the receiving member, the control system 112 can increase the image collection rate for determining an orientation of the tool in the receiving member. The collected images within the receiving member can include a longitudinal marking (or "stripe") that may be used to determine a relative rotational orientation of the tool within the receiving member. Since the longitudinal marking is only viewable from within the receiving member, image collection outside of the receiving member or viewed from a distal end of the receiving member may not include the longitudinal marking. As a distal end of the tool reaches a distal end of the receiving member (e.g. a catheter) one or more of the targets on the tool may be detected by one or more of the target detectors of the receiving member. These detections can indicate that the tool is nearing full insertion into the receiving member or that the tool is fully inserted. Images collected just prior to full insertion may be increasingly be dominated by anatomy. Therefore, it may be desirable to reduce or stop image collection by the tool of images used for orientation determination, since the tool may no longer be able to view the longitudinal marking. It should be understood that these but a few examples of the control changes that can occur based on the insertion position of the tool.

FIG. 4B illustrates the tool recognition assembly 410 coupled to an instrument carriage 415 (e.g., the instrument carriage 306) of a teleoperational manipulator assembly (e.g. teleoperational manipulator assembly 102). In alternative embodiments, the tool recognition assembly 410 may be coupled to non-teleoperational manipulators or other structures used for receiving a tool. In FIG. 4B, the tool recognition assembly 410 is coupled to the instrument carriage 415 proximal of an expandable support structure 417 that may be used to support an extended length of the receiving member 450 outside of the patient anatomy. For example, the tool recognition assembly 410 may be press fit onto a proximal mount (not shown) on the expandable support structure 417. As shown in FIG. 4B, the tool recognition assembly 410 may also include a baseline reader 408. The baseline reader 408 may comprise an inductive sensor (e.g., an inductor or inductive coil that detects a change in inductance caused by ferromagnetic and conductive properties of a material), a capacitive sensor, a Hall effect sensor, a photogate sensor, an optical sensor, a magnetic switch, a barcode scanner, an RFID scanner, a relative position sensor, or combinations thereof. As shown in the embodiment of FIG. 4B, the baseline reader 408 may be not be axially aligned with the target readers 406, 407. For example, the baseline reader may have an orientation orthogonal to the target readers 406, 407. In some embodiments, a baseline reader may be omitted or a baseline reader may be used with a single target reader. The baseline reader 408 may be in communication with a computing system configured to process readings from the target readers (e.g., changes in inductance, changes in resistance, changes in capacitance, changes in a magnetic field, changes in intensity of light, changes in colors of light, etc.). The computing system may be, for example, a component (e.g. control system 112) of a teleoperated medical system.

In some embodiments, the tool 404 may comprise an endoscope or vision probe configured to enable a physician to view internal body structures as a catheter or other receiving member 450 is delivered to the treatment or assessment site. Once at the destination, the vision probe may be withdrawn to make room for a different medical tool or for some other reason. The withdrawal of the probe may leave the physician unable to see the internal body structures to be treated or assessed. Accordingly, entering the safe mode upon detecting that the probe is not fully inserted into catheter may reduce the likelihood of patient injury resulting from adjustments to tools inserted in the patient after withdrawal of the probe. With the probe removed, the operator may be unable to see the internal body structures during the adjustments and therefore the control system may enter a mode that limits catheter flexibility and/or the speed at which the adjustments to the catheter may be made. Similarly, disabling certain functionalities when the probe is not fully inserted into the catheter may lower the risk of injuring the patient due to accidental use of such functionalities, e.g., accidental discharge of a puff of air into the lungs of a patient.

In some embodiments, a tool recognition assembly or other tool detection sensors may be located in other locations. For example, tool detection sensors may be located on a quick connect coupling between a vision probe and a catheter or on a motor pack of the teleoperational manipulator assembly. In some embodiments, a tool recognition assembly may recognize that a tool is absent from a tool holder, thus indicating that the tool may be in another location such as the catheter.

In some embodiments, based on the identified tool, time constants may be varied to allow for an amount of time a catheter may need to relax. In some embodiments, based on the identified tool, torque limits for pull wire motors can be changed, which can affect the amount a catheter is relaxed (e.g. the amount of torque applied by pull wire motors, can vary based on the type of tool installed). If the detected insertion signature identifies a needle, then the catheter could be temporarily "relaxed" (i.e. the pull wires controlling the catheter could provide a small amount of slack allowing the catheter to become more flexible). The relaxation of the catheter could facilitate the insertion of the needle without scraping the inner lumen of the catheter. Also, depending upon which type of tool is detected, user-interface input buttons on a control device can be reconfigured. For example, if a camera probe is detected a button can be provided for camera cleaning. If an ablation probe is detected, that same button can be reconfigured to provide for ablation energy to be delivered. If a needle with vacuum is detected, the same button can be reconfigured to provide vacuum. It should be understood that many different adjustments can be made based on which tool is identified by a detected insertion signature and based on whether the tool is fully inserted into the receiving member.

Figure 4C:
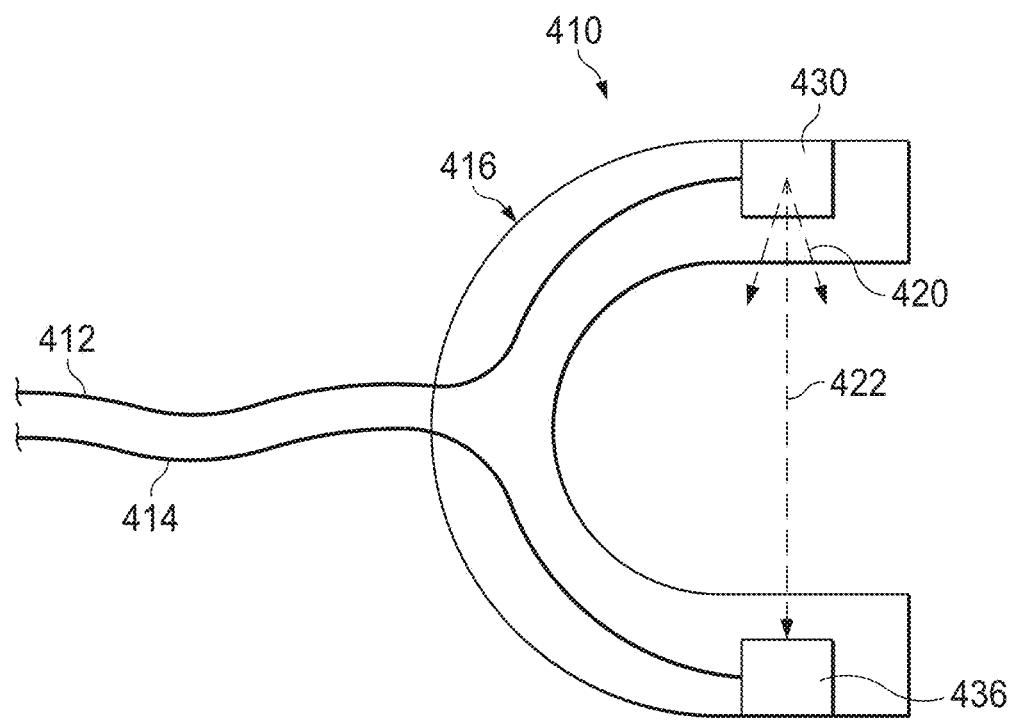

FIGS. 4C-4J illustrate various embodiments of target readers and targets that may be used to detect characteristic(s) of tools and/or catheters installed in a tool recognition assembly 410. FIG. 4C illustrates a tool recognition assembly 410 including a target reader having a source 430 and a detector 436 (which may be an optical detector). The source 430 and the detector 436 may be used to detect the presence, absence, position, classification (which may include a unique identifier, such as an identification of a tool manufacturer) or other information about a tool 404 (e.g. an imaging probe, a catheter, etc.) that is inserted between the source and the detector. A body 416 (e.g., a portion of the reader mount 402) may be used to position the source 430 and the detector 436 on opposite sides of a region through which the tool 404 can be installed. The source 430 and the detector 436 are positioned relative to each other in such as way so as to enable the detector 436 to sufficiently detect signals transmitted from the source 430. An example of the source 430 can be an optical source that may generate light signals 420 that are radiated toward the detector 436, which can be an optical detector. Some of the generated light signals 420 may be detected (e.g., detected light signal 422) by the detector 436 when no obstruction (such as a tool 404) is in the region between the source 430 and the detector 436. A conductor 412 connected to the source 430 can transfer signals (e.g. via electrical and/or optical means from a power source) to the source 430 for energizing the source and creating the light signals 420. A conductor 414 connected to the detector 436 can transfer signals (e.g. via electrical and/or optical means) from the detector 436 to a control system, such as the control system 112 based on detected property or properties (e.g., an intensity) of the detected light signals 422 received by the detector 436. As can be seen in FIG. 4C, no tool is positioned between the source 430 and the detector 436, thereby providing a threshold level of the intensity of the detected light signals 422 received at the detector 436 in absence of a tool. The threshold level of the intensity of the detected light signals 422 in absence of a tool is higher than when a tool is present between the source 430 and the detector 436.

Figure 4D:
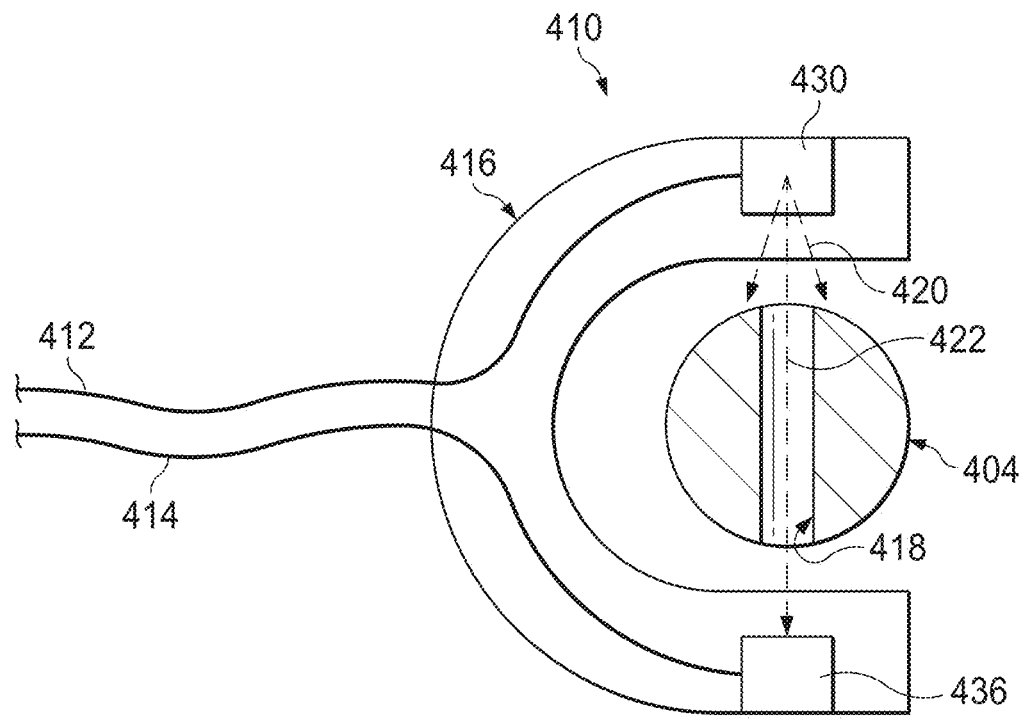
Figure 4E:
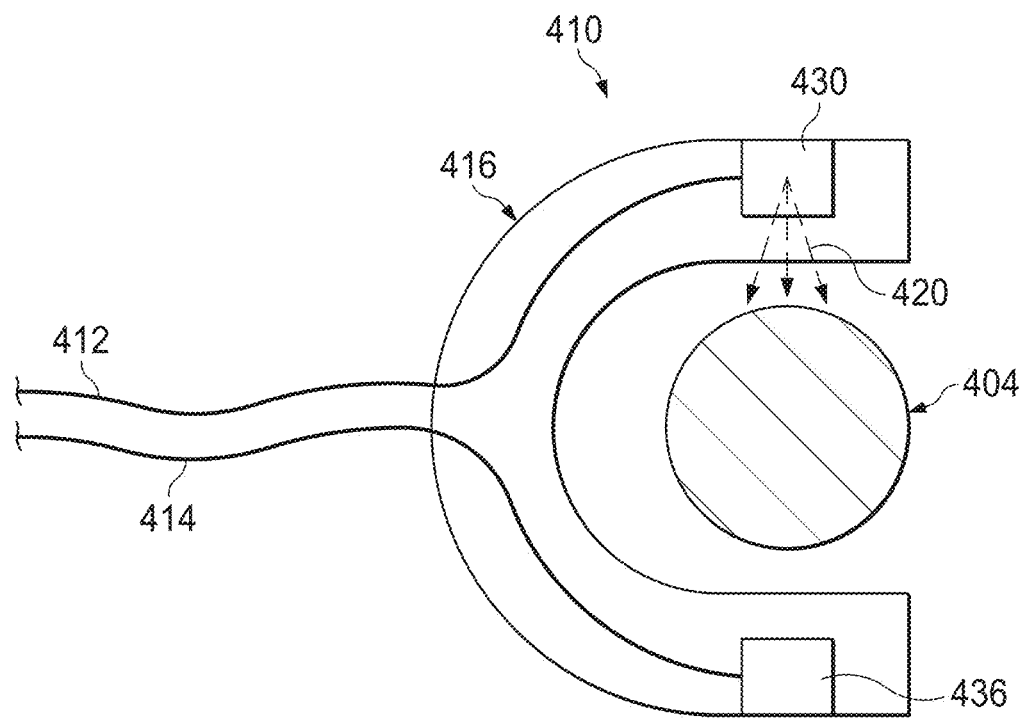

FIGS. 4D and 4E illustrate having the tool 404 positioned between the source 430 and the detector 436. FIG. 4D illustrates the tool 404 with a target 418 (which may be an aperture, an optical target, or any other suitable target) positioned to permit some of the generated light signals 420 to pass through the aperture and be received by the detector 436 as detected light signals 422. The intensity of the detected light signals 422 received at the detector 436 can be communicated to the control system via the conductor 414. The position of the tool 404 with the aperture in FIG. 4D can cause the detector 436 to detect a high intensity of the detected light signals 422. The position of the tool 404 in FIG. 4E without the target 418 (e.g., an aperture) positioned between the source 430 and the detector 436 can cause the detector 436 to detect a low intensity of the detected light signals due to the interference of the tool 404 with the generated light signals 420. One or more processors in the control system 112 can use the sensor data from the detector 436 to determine the presence, absence, position, and/or classification of the tool installed in the tool recognition assembly 410.

One or more targets 418 (e.g., apertures) can be included in the tool 404 to generate an appropriate detected insertion signature to identify a position and/or classification of the tool 404. With multiple targets 418 on the tool 404, the detector 436 can detect several variations in the intensity of the detected light 422 as the tool 404 is inserted into the tool recognition assembly 410. For example, the detected insertion signature can include (1) a low intensity of the detected light 422 as in FIG. 4E when a target is not detected because the target is not yet positioned in the region between the source 430 and the detector 436, (2) a high intensity of the detected light 422 as in FIG. 4D when a target is detected due to being moved into the region between the source 430 and the detector 436, (3) the low intensity of the detected light 422 again as in FIG. 4E when the target moves past the region between the source 430 and the detector 436, which can be used to create an insertion signature of the tool 404 being inserted. The above described detected insertion signature can include alternating intensities detected between low intensity and high intensity when additional targets are included with the tool 404. The detected insertion signature can be compared to pre-existing model insertion signatures to identify a type of tool 404 being inserted. It should be understood that a wide range of numbers of targets (e.g., apertures) and spacing of the targets along the tool 404 can be used to provide a unique pattern of measurements that make up a detected insertion signature.

Figure 4F:
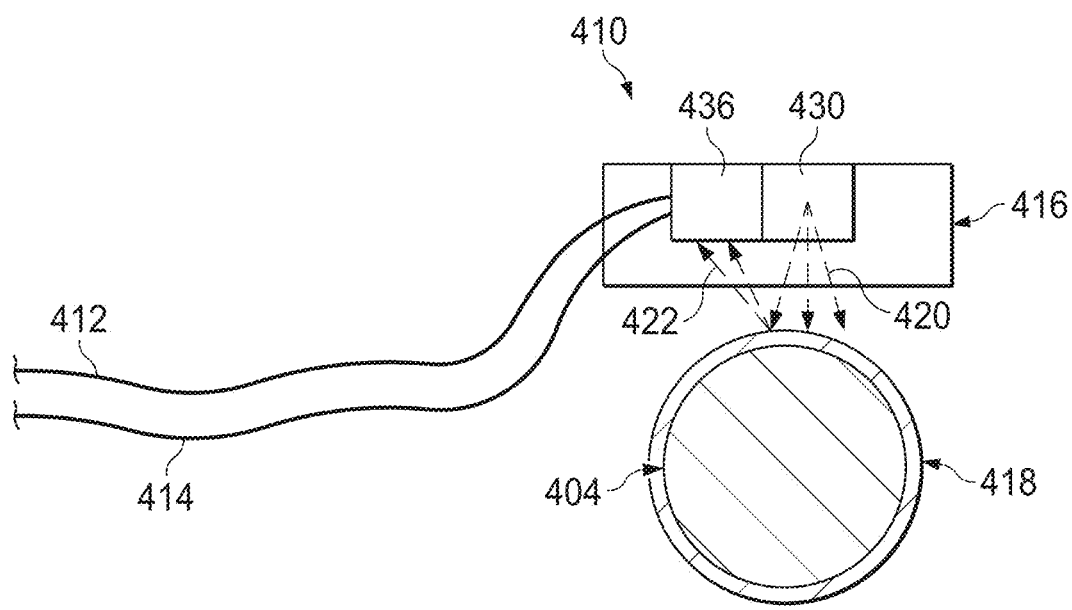
Figure 4G:
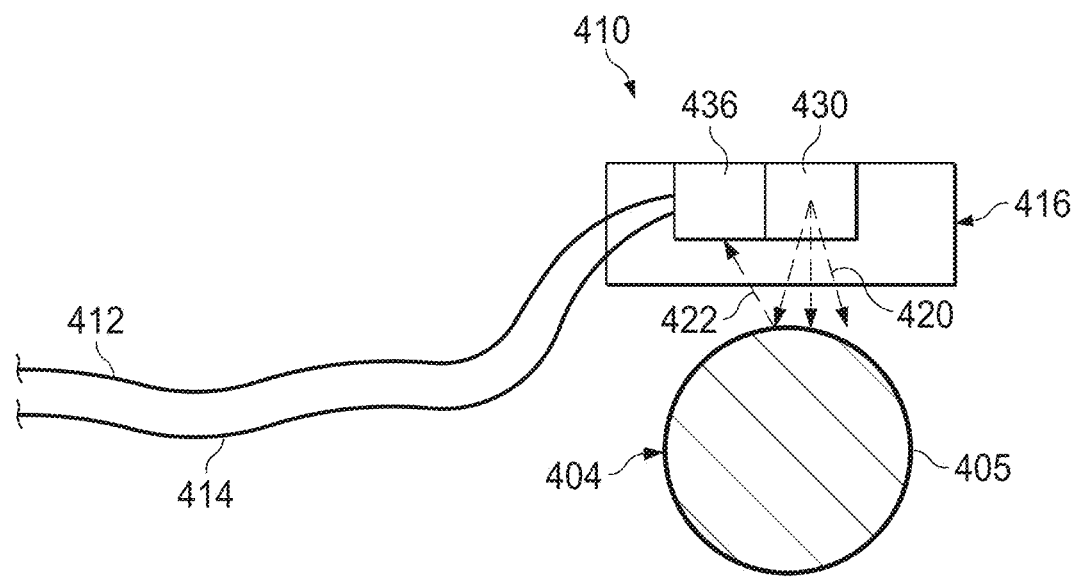

Referring now to FIGS. 4F and 4G, another configuration of the source 430 and detector 436 are representatively illustrated and can be used to detect the presence, absence, position, classification or other information about a tool. A tool 404 can be positioned adjacent to the source 430 and the detector 436 pair, with a target 418 (e.g. in this embodiment a reflective surface or surface treatment) positioned to redirect some of the generated light signals 420 toward the detector 436 to be received as the detected light signals 422. The intensity of the detected light signals 422 received at the detector 436 can be communicated, for example to a control system, via the conductor 414. The position of the tool 404 in FIG. 4F, with the target 418 proximate the source:detector (430:436) pair, can cause the detector 436 to detect a high intensity of the detected light signals 422. The position of the tool 404 in FIG. 4G, with a target 418 not proximate the source:detector (430:436) pair, can cause the detector 436 to detect a low intensity of the detected light signals 422. One or more processors in the control system 112 can use the signals communicated from the detector 436 to determine the presence, absence, position, and/or classification of the tool installed in the tool recognition assembly 410.

One or more targets 418 can be included with the tool 404 as is desired to generate readings that make up an appropriate detected insertion signature to identify a position and/or classification of the tool 404. With multiple targets 418 on the tool 404, the detector 436 can detect several variations in light intensity of the detected light signals 422 that coincide with the detection of the multiple targets 418 (e.g. a low intensity as in FIG. 4G representing no target detected, a high intensity as in FIG. 4F representing a target detected, then the low intensity again as in FIG. 4G as the target moves away, and then high intensity as in FIG. 4F again as the next target is detected) as the tool 404 is inserted into the tool recognition assembly 410 to create a target detection pattern that make up an insertion signature of the tool 404. The detected insertion signature of the tool 404 can be compared to pre-existing model insertion signatures to identify a type of tool 404 being installed. It should be understood that a wide range of numbers of targets 418 and spacing of targets along the tool 404 can be used to generate a unique detected insertion signature. The targets 418 can be any material or surface that can be used to affect one or more properties of the signals generated by the source 430, such as an intensity of light directed to the detector 436. For example, the targets 418 can be a reflective band of material (such as a band of metal) that is positioned around an exterior surface of the tool 404 which will reflect more light from the source 430 to the detector 436 when the target 418 is proximate to the source:detector pair. The targets 418 can also be a surface treatment or a material that changes an intensity of light being directed to the detector 436, such as when the target 418 is a different color (i.e. coloring a portion of the exterior surface 405 to be different than the rest of the exterior surface 405 and/or making the tool 404 out of various colored materials), when the exterior surface 405 is treated to absorb more light at target locations (i.e. lighter and darker shades of color including white and black, different hues of color, etc.), and/or when the exterior surface 405 has varying textures that diffuse and/or disperse light differently, thereby causing variations in an intensity of the detected light signal(s) 422 received by the detector 436. It should be understood that the target 418 can also cause a low intensity of light to be detected by the detector 436, while the absence of target can cause a high intensity of light to be detected by the detector 436.

Figure 4H:
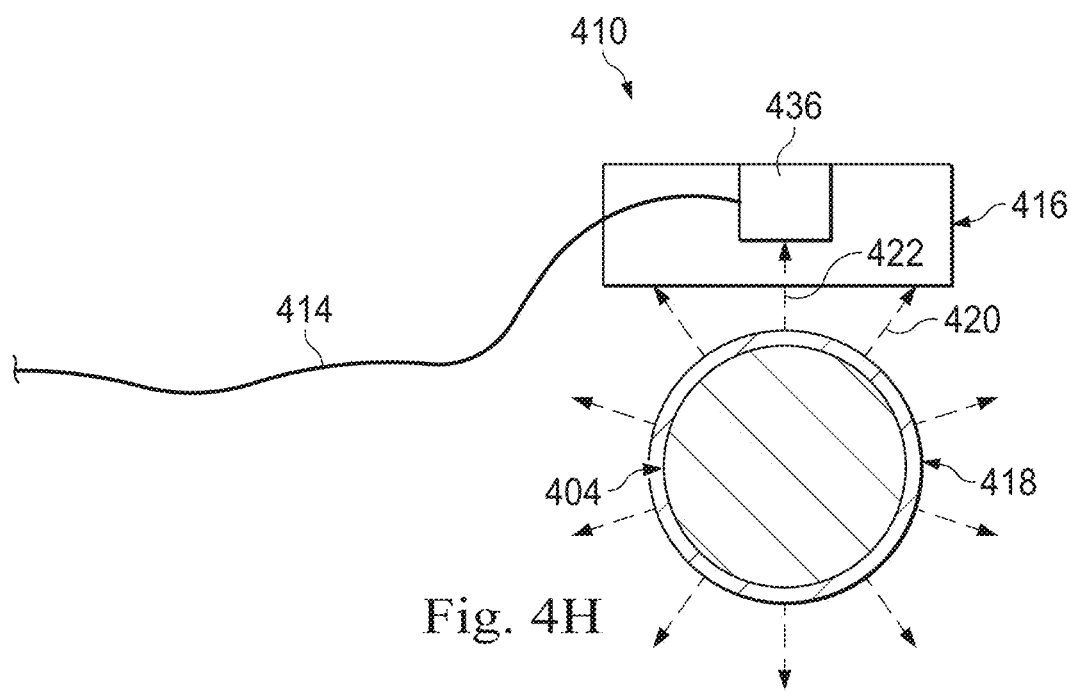

Referring now to FIGS. 4H and 4I, another configuration of the target reader in the tool recognition assembly 410 is illustrated. In the example shown in FIGS. 4H and 4I, the target reader is implemented to include a detector 436 (without a source) to detect the presence, absence, position, classification, or other information about a tool. This configuration differs from the previously described target reader at least in that the target reader does not include a source and does not supply source signals, such as the optical signals 420. In this configuration, the target 418 on the tool 404 can be the source, such as the optical source and can supply the source signals, such as the optical signals 420 that radiate from the target 418. The tool 404 can be positioned adjacent to the detector 436, with a target 418 (e.g. an optical source or an optical light source, such as phosphorescent, discrete LEDs, luminescent ring, a ring that diffuses light from a discrete light source, etc.) positioned to generate the source light signals 420 that are received by the detector 436 as the detected light signals 422. The intensity of the detected light signals received at the detector 436 can be communicated, for example to a control system, via the conductor 414. The position of the tool 404 in FIG. 4H, with the target 418 proximate the detector 436, can cause the detector 436 to detect a high intensity of light from the target 418 as the detected light signals 422. The position of the tool 404 in FIG. 4I, with a target 418 not proximate the detector 436, can cause the detector 436 to detect a low intensity of light from the target 418 as the detected light signals 422. One or more processors in the control system 112 can use the signals communicated from the detector 436 to determine the presence, absence, position, and/or classification of the tool installed in the tool recognition assembly 410.

One or more targets 418 can be included with the tool 404 as is desired to generate readings that make up an appropriate detected insertion signature to identify a position and/or classification of the tool 404. With multiple targets 418, the detector 436 can detect several variations in light intensity corresponding to detecting the absence and presence of the targets 418 (e.g. a low intensity as in FIG. 4I representing absence of a target, a high intensity as in FIG. 4G representing presence of a target, then the low intensity again as in FIG. 4I representing absence of a target) as the tool 404 is inserted into the tool recognition assembly 410 to create a unique detected insertion signature of the tool 404. Again, the detected insertion signature of the tool 404 can be compared to pre-existing model insertion signatures to identify a type of tool 404 being installed. It should be understood that a wide range of targets 418, numbers of targets 418, and spacing of targets 418 along the tool 404 can be used to create a detected insertion signature. In this configuration of the optical target reader and optical target, the targets can be any material or light source that can be used to generate the optical source signals 420 that can be directed to the detector 436. For example, the targets 418 can be a phosphorescent ring, discrete light sources (e.g. LEDs) arranged in a ring, a luminescent ring, and/or a ring that diffuses light from a discrete light source (e.g. an LED).

It should also be understood that the optical target readers and optical targets can be used along with and/or as an alternative to any other types of target readers and targets provided in this disclosure. For example, this and other versions of the optical target readers and optical targets can be used with electromagnetic embodiments of the target readers and targets.

Referring now to FIG. 4J, another diagrammatic view of a tool recognition assembly 410 is shown with various target reader and target pairs. A first target reader:target pair can include a target reader including a Hall effect sensor 460 which can detect the proximity of the magnetic field 466 produced by a target including a magnet 474 (e.g., an electromagnet). As the tool 404 is installed in the tool recognition assembly 410, the Hall effect sensor 460 can detect when the magnet 474 is within a certain distance to the Hall effect sensor 460. A second target reader: target pair can include a target reader including an RFID scanner 462 which can detect the proximity of a target including an RFID chip 476 within a certain distance to the RFID scanner 462. The RFID scanner can radiate radio frequency (RF) signals 470 that can read the ID from the RFID chip 476 and transfer that information to the control system 112. The RFID target reader:target pair may be more suitable for identifying which tool 404 is installed in the tool recognition assembly 410, but the pair can also be used to determine whether the tool 404 is fully installed in the tool recognition assembly 410. For example, the model insertion signature indicating a fully inserted tool can include detecting the RFID ID. A third target reader:target pair can include a target reader including a bar code scanner 464 which can read a bar code of the target 478 by illuminating the target 478 with light and reading the reflected light patterns. The bar code scanner target reader:target pair may be more suitable for identifying which tool 404 is installed in the tool recognition assembly 410, but the pair can also be used to determine whether the tool 404 is fully installed in the tool recognition assembly 410. For example, the model insertion signature indicating a fully inserted tool can include detecting the bar code.

Referring now to FIGS. 5A-5S, various configurations of a tool recognition assembly 500 which may include all or some of the structure and functionality of the tool recognition assembly 410. The tool recognition assembly 500 may incorporate one or more target reader:target pairs, such as those described in FIG. 4J. In each of the configurations illustrated in FIGS. 5A-5S, a tool 520, which may include all or some of the structure and functionality of the tool 404 (e.g. an imaging tool, an ablation tool, a catheter, etc.), is sensed by the tool recognition assembly 500. It should also be understood that FIGS. 5A-5S can include multiple tools 520 with each tool 520 producing an insertion signature when each tool 520 is inserted into the receiving member 516.

Referring now to FIG. 5A, the tool recognition assembly 500 includes two target readers 510, 514 for sensing a tool 520 having a target 528. The target readers 510, 514 may be substantially similar to target reader 406 or 407, and the target 528 may be substantially similar to a target 456 or 457. The tool recognition assembly 500 may be configured to detect whether or not the tool 520 is fully inserted into a receiving member 516.

In the embodiment of FIG. 5A, the model insertion signature for determining that the tool 520 is fully inserted into the receiving member 516 of the tool recognition assembly 500 includes a positive reading for target detection from the distal target reader 514 while the proximal target reader 510 indicates a negative reading for target detection. As described above, such a model insertion signature may advantageously limit the incidence of false positives of a fully inserted tool 520. In FIG. 5A, the tool 520 is fully inserted into the tool recognition assembly 500. In that regard, the target 528 is aligned (or at least in a proximity range) with the distal target reader 514. In this position, the distal target reader 514 can detect the target 528 while the proximal target reader 510 is unable to detect the target 528. The tool 520 may be formed of a material undetectable by the target readers 514.

Though the target 528 is illustrated as having approximately the same dimension (e.g., length) as the target readers 510, 514, in various alternative embodiments, it may be advantageous for the target 528 to have a different dimension, such as being substantially longer than the target readers 510, 514. Optionally, the tool recognition assembly 500 may be configured to provide an indication (e.g., an audible tone, a visual prompt, tactile feedback, etc.) when the target 528 is read by one of the target readers 510, 514. In that regard, a short target 528 may pass quickly through the target readers 510, 514 such that control system 112 may fail to recognize that the target 528 was aligned with the target readers 510, 514. By contrast, a longer target 528 may take longer to pass through the target readers 510, 514, thereby increasing the likelihood that the control system 112 receives an indication that a target reader 510, 514 detects the target 528.

The target 528 may be, for example, between 7 and 68 millimeters in length and the target readers 510, 514 may be spaced apart by a distance of between 3 and 60 millimeters. The target readers 510, 514 can be spaced a sufficient distance from each other so that a given target 528 cannot be detected by both target readers 510, 514 at once. For example, if the target readers 510, 514 are capable of detecting the target 528 from 4 millimeters away (see distances L3, L4 in FIG. 5S as an example) and the target 528 is 15 millimeters long, then the target readers 510, 514 may be spaced at least 23 millimeters apart. Similarly, if the target 528 is 30 millimeters long and the target readers 510, 514 are capable of detecting the target 528 from 4 millimeters away, the target readers 510, 514 may be spaced 38 millimeters apart.

FIGS. 5B-5D illustrate additional embodiments of the tool recognition assembly 500, with repeated reference numerals to represent the same previously disclosed elements as appropriate. For example, FIGS. 5B, 5C, and 5D illustrate three target readers 510, 512, 514 while FIG. 5A illustrates two target readers 510, 514. FIGS. 5A and 5B have one target 528, where FIG. 5C has two targets 526, 528 and FIG. 5D has two targets 524, 526. Accordingly, descriptions of those elements of FIG. 5A applicable to the corresponding elements of FIGS. 5B-5D are not repeated.

FIG. 5B depicts the tool recognition assembly 500 including target readers 510, 512, 514 for sensing a tool 520 having a single target 528. When the tool recognition assembly 500 comprises three target readers 510, 512, 514 and the tool 520 comprises a single target 528, multiple detected insertion signatures can be generated and used to indicate whether the tool 520 is properly inserted for operation (e.g. fully inserted into the receiving member 516). One detected insertion signature can indicate that the tool 520 is properly inserted when the target reader 514 indicates a positive detection reading for the target 528 while target readers 510, 512 indicate negative detection readings for the target 528, as shown in FIG. 5B. Alternatively (and not shown) a detected insertion signature indicating that the tool 520 is properly inserted can be generated when the target 528 is aligned with the target reader 512. The target reader 512 may indicate a positive detection reading for the target 528 while target readers 510, 514 indicate negative detection readings for the target 528. As described above, the target readers 510, 512, 514 may be spaced apart from each other a sufficient distance to prevent two of the target readers 510, 512, 514 from detecting the same target 528 concurrently.

FIG. 5C depicts the tool recognition assembly 500 including three target readers 510, 512, 514 for sensing the tool 520 having two targets 526, 528. A detected insertion signature can be generated to indicate that the tool 520 is fully inserted within the tool recognition assembly 500 when the target readers 512, 514 indicate a positive detection reading for the targets 526, 528, respectively, with the target reader 510 indicating a negative detection reading for the targets 526, 528. As described above, the target readers 510, 512, 514 may be spaced apart from each other a sufficient distance to prevent two of the target readers 510, 512, 514 from detecting the same target 526 or 528 concurrently.

FIG. 5D depicts the tool recognition assembly 500 including three target readers 510, 512, 514 for sensing the tool 520 having two targets 524, 528. A detected insertion signature can be generated to indicate that the tool 520 is fully inserted within the tool recognition assembly 500 when the target readers 510, 514 indicate positive detection readings for the targets 524, 528 while the target reader 512 indicates a negative detection reading for the targets 524, 528. As described above, the target readers 510, 512, 514 may be spaced apart from each other a sufficient distance to prevent two target readers 510, 512, 514 from detecting the same target 524 or 528 concurrently.

Referring now to FIGS. 5E-5J, these figures show an exemplary diagrammatic installation sequence of a tool 520 being installed into a tool recognition assembly 500. In this example, the tool recognition assembly 500 includes two target readers 510, 512 and the tool includes two targets 526, 528. The target reader 510 can be referred to as the absence reader A, and the target reader 512 can be referred to as the presence reader P. Each of the FIGS. 5E-5J indicate whether the absence A and presence P target readers 510, 512 have a positive or negative detection reading for a target 526 or 528. For example, FIG. 5E shows both the absence A and presence P target readers 510 and 512 having a negative detection reading (A=0 and P=0) corresponding to both readers 510 and 512 not having detected the targets 526 and 528. FIG. 5F shows A=1, and P=0, which indicates that the absence A target reader 510 has a positive detection reading of a target (e.g. target 528 in this case), and that the presence P target reader 512 has a negative detection reading of the targets 526, 528. The logic states of the absence A and presence P target readers 510, 512 can be used to develop a detected insertion signature of the tool 520 which can be retained (e.g. in storage, in written form, in a pictorial representation, etc.) for later reference and/or comparison to previously retained model insertion signatures to determine the absence, presence, position, and/or classification of the tool 520. In the embodiment of FIGS. 5E-5J the detected insertion signature may include various combinations of readings, such as a sequential set of readings from the target readers. The readings from the target readers may be compared to a model insertion signature. The model insertion signature may be a static signature that identifies a match based on a current logic state of the target reader or may be a series of model signatures that identifies a match based on a sequential set of readings that must match the detected set of readings before a signature match is registered.

FIG. 5E, shows the tool 520 being inserted into the tool recognition assembly 500 to a position where the target 528 has not yet reached the target reader 510 (i.e. A=0, P=0). As the tool 520 continues to be inserted into the tool recognition assembly in the direction 550 (e.g. toward the patient), the target 528 can become aligned with the target reader 510, as shown in FIG. 5F. At this position, the absence A reader is "1" indicating a positive detection reading, with the presence P reader being "0" indicating a negative detection reading (i.e. A=1, P=0). At this point, the detected insertion signature obtained from the thus far generated readings may not match with a model insertion signature, and therefore, indicates that the tool 520 is not fully installed in the tool recognition assembly 500. Therefore, the insertion of the tool 520 can continue. At the position of the tool 520 in FIG. 5G, neither of the targets 526, 528 are detected by either of the target readers 510, 512. Therefore, both the absence A reader and the presence P reader are "0" indicating a negative detection reading (i.e. A=0, P=0). At this point, the detected insertion signature obtained from the thus far generated readings still may not match to the model insertion signature, and therefore, continues to indicate that the tool 520 is not fully installed in the tool recognition assembly 500. Therefore, the insertion of the tool 520 can continue.

At the position of the tool 520 in FIG. 5H, both of the targets 526, 528 are detected by respective target readers 510, 512. Therefore, both the absence A reader 510 and the presence P reader 512 are reading a "1" indicating positive detection readings (i.e. A=1, P=1). At this point, the detected insertion signature obtained from the thus far generated readings still may match to the model insertion signature, and therefore, continues to indicate that the tool 520 is not fully installed in the tool recognition assembly 500. Therefore, the insertion of the tool 520 can continue. At the position of the tool 520 in FIG. 5J, neither of the targets 526, 528 are detected by either of the target readers 510, 512. Therefore, both the absence A reader and the presence P reader are reading a "0" indicating a negative detection reading (i.e. A=0, P=0). At this point, the detected insertion signature obtained from the thus far generated readings may still not match to the model insertion signature, and therefore, continues to indicate that the tool 520 is not fully installed in the tool recognition assembly 500. Therefore, the insertion of the tool 520 can continue. At the position of the tool 520 in FIG. 5J, the absence A reader is reading a "0" indicating a negative detection reading, with the presence P reader reading a "1" indicating a positive detection reading (i.e. A=0, P=1). At this point, the detected insertion signature from the thus far generated readings can be compared to the model insertion signature. When the detected insertion signature obtained from the sequence of the readings through 5J is determined to match the sequence of readings in the model insertion signature, then the tool 520 can be seen as being fully installed in the tool recognition assembly 500. Therefore, the insertion into the tool recognition assembly can stop.

It should be understood that this is merely an example of the principles of the present disclosure, and the detected insertion signatures obtained from readings generated at the readers 510, 512 can be used to determine the absence, presence, position, and/or classification of the tool 520. For the example of the system shown in FIGS. 5E-5J, the insertion signature can be represented as the states for the absence A and the presence P readers 510, 512 logged in sequence, such as 1) A=0, P=0; 2) A=1, P=0; 3) A=0, P=0; 4) A=1, P=1; 5) A=0, P=1. This detected insertion signature that includes a sequence of readings at the readers 510, 512 can be compared to other model insertion signatures to identify the position of the tool 520 in the tool recognition assembly 500 and/or identify the tool as a particular instrument type or a particular instrument. Portions of the detected insertion signature can be used to indicate the absence of the tool 520 (e.g. when A=0, P=0 as in FIG. 5E) or the presence of the tool 520 (e.g. when either A=1 or P=1 as in FIGS. 5F, 5H, 5J). When only one target is used (e.g., the target 528 were not used) in FIGS. 5E-5J, the detected insertion signature could be represented as 1) A=0, P=0 (FIG. 5G but target 528 not used); 2) A=1, P=0 (FIG. 5H but target 528 not used); 3) A=0, P=0 (FIG. 5I but target 528 not used); 4) A=0, P=1 (FIG. 5J but target 528 not used). Therefore, it should be understood that several variations of the number of readers and targets can be used, as well as a longitudinal spacing between adjacent readers and longitudinal spacing between adjacent targets. All of these factors can be modified/tuned/changed/adjusted to accommodate many variations of the detected insertion signatures.

FIGS. 5K and 5L show another exemplary diagrammatic installation sequence of a tool 520 being installed into a tool recognition assembly 500 with another configuration of target readers and targets. In this example, the tool recognition assembly 500 includes two target readers 510, 512 and the tool 520 includes one elongated target 528. The elongated target 528 can be long enough to span between the target readers 510, 512, as shown in FIG. 5L, such that the absence A reader and the presence P reader may detect the same target 528 concurrently, which can be used to create a unique detected insertion signature. The detected insertion signature shown in FIGS. 5K and 5L can be represented as 1) A=1, P=0; 2) A=1, P=1. If the detected insertion signature matches to a model insertion signature, the tool may be recognized as fully or adequately inserted.

Referring now to FIGS. 5M-5R, these figures show diagrammatic views of various embodiments of the tool recognition assembly 500. These figures show configurations of the system (e.g., tool recognition assembly 500) that can utilize optical target readers and optical targets, such as optical target readers 406 and optical targets 456 shown in FIGS. 4C-4E. It should be understood that these optical target readers and optical targets, as well as other configurations, such as the optical target readers and optical targets shown in FIGS. 4F-4G, can be substituted for any of the reader/target sets in any of the system (e.g., tool recognition assembly 500) embodiments in this disclosure.

FIG. 5M shows a diagrammatic view of the tool recognition assembly 500 which comprises two optical reader: target pairs and one non-optical reader:target pairs (such as an RFID reader:target pair, a magnetic reader:target pair, an electromagnetic reader:target pair; etc.). The optical sources 530, 532 for the two optical readers radiate optical signals toward the respective optical detectors 536, 538. When a target 524 (which may be an aperture) is formed through the tool 520 and positioned to be detected by the optical readers, at least a portion of the source light signals from the optical sources 530, 532 can be received by the optical detectors 536, 538 through the target. The light signals received at the optical detectors 536, 538 can have a higher intensity relative to when the target is positioned so as to not be detected by the optical readers. In absence of the target (e.g., aperture), limited light signals may be detected by the optical detectors, which can lead to a low intensity of the light signals received at the detector relative to when the target is positioned to be detected by the target readers. The higher intensity light detection can indicate the absence of the tool 520 or the presence of an aperture (such as target 524), and can be represented by a negative reading of "0." The low intensity light detection can indicate the presence of the tool 520, at least at the location of the reader:target pair, and can be represented by a positive reading of "1." Therefore, the system (e.g., tool recognition assembly 500) in FIG. 5M can be seen as having three target readers (i.e. two optical source:detector pairs 530:536, 532:538, one non-optical reader 514), and two targets (i.e. one aperture target 524, one non-aperture target 528). The current position of the tool 520 in the tool recognition assembly 500 shown in FIG. 5M can yield a state of the three readers as being reader 530:536="0"; reader 532:538="1"; and reader 514="1".

Similarly, the system (e.g., tool recognition assembly 500) in FIG. 5N can be seen as having two target readers (i.e. optical source:detector pairs 530:536, 532:538), and one target (aperture 528). The current position of the tool 520 in the tool recognition assembly 500 shown in FIG. 5N can yield a state of the two readers as being reader 532:538="1"; reader 534:540="0".

Similarly, the system (e.g., tool recognition assembly 500) in FIG. 5P can be seen as having three target readers (i.e. optical source:detector pairs 530:536, 532:538, 534:540), and two targets 526, 528 (which may be apertures). The current position of the tool 520 in the tool recognition assembly 500 shown in FIG. 5P can yield a state of the three readers as being reader 530:536="1"; reader 532:538="0"; and reader 534:540="0".

Similarly, the system (e.g., tool recognition assembly 500) in FIG. 5R can be seen as having three target readers (i.e. optical source:detector pairs 530:536, 532:538, 534:540), and two targets 524, 528 (which may be apertures). The current position of the tool 520 in the tool recognition assembly 500 shown in FIG. 5R can yield a state of the three readers as being reader 530:536="0"; reader 532:538="1"; and reader 534:540="0".

FIG. 5S shows a diagrammatic view of the tool recognition assembly 500 which comprises two target readers 510, 512 and one target 526 (items 526*a-e* are different positions of the one target 526). As the tool 520 is being inserted through the tool recognition assembly 500, the target 526 can travel through various positions 526*a-e*. As the target 526 approaches the first reader 510, the target 526 is not detectable by the first reader 510 until the target 526 comes within a distance of L1 from the reader 510 (e.g. position 526*a*). Within the distance L1 to the first reader 510, the target may be detectable, but the detected signal may not be strong enough to ensure that the detection is valid. However, within the distance L3 to the first reader 510, the detection of the target 526 can be relied upon as a valid detection (e.g. position 526*b*). As the target 526 passes the reader 510, the detection of the target 526 can be relied upon as a valid detection until the target 526 travels past the distance L4 from the reader 510. Therefore, detections of the target 526 as the target 526 remains within the distance L5 can be seen as valid detections.

The distance L2 represents the longitudinal length of the reader 510. Therefore, the distance L5 includes the distances L2, L3, L4 and can be seen as the detection zone of the reader 510. When the target 526 travels past the first reader 510 by a distance L1 (basically position 526*d*), the target 526 will no longer be detectable by the first reader 510. The distance L6 is the distance between the first and second readers 510, 512 which can ensure minimal interference between the two readers 510, 512 when detecting the target 526. It should be understood that these distances are examples and can be different for other examples, such as the example system (e.g., tool recognition assembly 500) shown in FIGS. 5K and 5L, where the target can be detected by both readers. The detection zone for an optical target reader (such as those in FIGS. 4C-4E) can be the diameter of the target 418 (e.g., the aperture), plus a short distance L3, L4 on either side of the target 418 (e.g., the aperture), which can represent a part of the detection zone that the target readers detect indirect light that travels through the target 418 (e.g., the aperture), but does not directly strike the target reader. When the target reader is directly underneath the aperture, then light signals can directly strike the optical reader providing an increased intensity of detected light.

The distance L1 may be, for example, 4 mm, 5 mm, or a value between approximately 4-5 mm. In some implementations, the distance L1 may be larger including 6 mm, 7 mm, 8 mm, 9 mm, 10 mm, or a value between approximately 4 and 10 mm. The distances L3 and L4 may be, for example, 2 mm, 3 mm, 4 mm, or a value between approximately 2 and 4 mm. The distance L2 can be any distance suitable for the target reader being utilized. In some embodiments, the distance L2 is within the range from approximately 3 mm to 60 mm. The distance L2 can be, for example, 3 mm, 4 mm, 6 mm, 8 mm, 10 mm, 12 mm, 20 mm, 30 mm, 40 mm, 50 mm, and 60 mm. Since distance L5 is the sum of the distances L2, L3, L4, then L5 can range from approximately 7 mm to 68 mm. The distance L5 can also be seen as a desirable separation distance between adjacent targets. However, the targets can be separated by a smaller or larger distance that the distance L5. The distance L6 may be, for example, 9 mm, 10 mm, 11 mm, 12 mm, 13 mm, 14 mm, 15 mm, 16 mm, 17 mm, 18 mm, 19 mm, 20 mm, or a value between approximately 9 and 20 mm. Selecting the desired dimensions from the specified ranges for the distances L1, L2, L3, L4, L5, and L6 can depend upon the target readers utilized in the system (e.g., tool recognition assembly 500), the strength and sensitivity of the readers, current supplied to the readers (e.g. an inductor or inductive coil that detects ferromagnetic materials), and the ambient conditions. Therefore, routine experimentation can be used to determine the best dimensions for these distances for a particular system (e.g., tool recognition assembly 500).

Referring now to FIG. 6A, a reader:target pair 600 is shown to utilize an electromagnetic target reader 601 (which can be an example of a target reader 406 shown in FIG. 4A) and a ferromagnetic target (which can be an example of a target 456 shown in FIG. 4A). The target reader 601 can include a coil 602 disposed around a core 604 and can be mounted to a tool recognition assembly 608 (e.g. tool recognition assembly 500). The ferromagnetic target 606 can be installed along a tool, such as tool 404. As the tool 404 is inserted in a tool recognition assembly 608, the magnetic field (not shown) surrounding the ferromagnetic target 606 can be detected by the target reader 601. The coil 602 can be, for example, approximately 3 to 5 millimeters long. The core 604 can comprise an inductive material, such as a ferromagnetic material, and can be, for example, approximately 5 to 6 millimeters wide, 4 to 5 millimeters tall, and 6 to 7 millimeters long. As used herein, width corresponds to dimensions along the X axis shown in the various figures, height corresponds to dimensions along the Y axis shown in the various figures, and length corresponds to dimensions along the Z axis shown in the various figures.

The coil 602 may detect the proximity of the target 606 within a certain distance of the coil by reading a change in inductance that can occur when the target 606 is placed within the certain distance from the coil 602. To detect a change in the inductance, a baseline inductance may need to be established. For example, when the reader/target pair 600 is implemented in the tool recognition assembly 410, the baseline inductance may be established by the baseline reader 408, which may comprise a target reader 406 configured to read an empty annulus. The baseline reader may measure environmental inductance that is influenced by environmental factors including temperature changes, vibration changes, iron in patient blood, polychlorinated biphenyl (PCB) compounds, nearby mechanical assemblies, or the like. The baseline inductance may be established once or can be established and reestablished multiple times during a medical operation. Therefore, the baseline can be established once; or each time the tool recognition assembly 410 is powered on; or at regular intervals (e.g., every minute, every hour, every day, every week); or after the occurrence of certain events (e.g., after each procedure, after removal of a tool 404); or in response to combinations thereof. The change in inductance can be measured relative to the baseline inductance and can be measured as current is passed through the coil 602. A threshold can be established for what change in inductance relative to the baseline inductance will be considered a positive or negative reading for the presence of the target 606.

The reader:target pair 600 may be in communication with one or more processors of the control system 112 configured to process readings from the reader/target pair 600. For example, the one or more processors may be configured to calculate a change in inductance or in a magnetic field based on data received from the reader/target pair 600. In some embodiments, a baseline reading of the sensors (e.g., baseline inductance) can be measured and stored during manufacturing, and then referenced by the system during use. Using a pre-stored baseline reading of the sensor eliminates the need for a baseline coil.

FIGS. 6B and 6C illustrate additional embodiments of the reader/target pair 600. FIG. 6B depicts a reader:target pair 610. A target reader 611 includes a coil 612 disposed around a core 614. A target 616 can be installed along a tool, such as tool 404. As the tool 404 is inserted in a tool recognition assembly 618, the magnetic field (not shown) surrounding the target 606 can be detected by the target reader 611. In this example, when compared to the reader:target pair 600 in FIG. 6A, the coil 612 is wider, and the core 614 is longer than the core 604. In particular, the core 614 may be approximately 8 to 9 millimeters wide, 4 to 5 millimeters tall, and 13 to 14 millimeters long.

Similarly, FIG. 6C depicts a reader/target pair 620. A target reader 621 includes a coil 622 disposed around a core 624. A target 626 can be installed along a tool, such as tool 404. As the tool 404 is inserted in a tool recognition assembly 628, the magnetic field (not shown) surrounding the target 606 can be detected by the target reader 621. In this example, when compared to the reader:target pair 600 in FIG. 6A, the coil 622 and the core 624 may be longer than the coil 602 and the core 604. In particular, the core 624 may be approximately 5 to 6 millimeters wide, 4 to 5 millimeters tall, and 13 to 14 millimeters long. In addition, the embodiments illustrated in FIGS. 6A, 6B, and 6C show a core (e.g., core 604, 614, 624) that is parallel to the length of the tool recognition assembly (e.g., tool recognition assembly 608, 618, 628). However, the core (e.g., core 604, 614, 624) and the tool recognition assembly (e.g., tool recognition assembly 608, 618, 628) can be configured to be orthogonal to each other such that the core endpoints are on either side of the tool recognition assembly similar in shape as illustrated in FIG. 4E.

FIG. 6D illustrates the performance of an example reader:target pair. Graph 630 depicts a percentage change in inductance over distance from the target in millimeters for a reader:target including a copper coil, a half inch long ferromagnetic core, and a ferromagnetic target. As can be seen from the graph 630, change in inductance spikes dramatically once the target moves within a certain distance (e.g., 4 millimeters) of the coil-core arrangement. A threshold for a positive reading for the presence of the target can be established as a change in inductance consistent with the target being within a distance of 4 millimeters from the coil-core arrangement, e.g., target reader 406.

Referring now to FIG. 7A, a reader:target pair 700 is described. The reader:target pair 700 includes a reader that is a shell-type where a core surrounds a coil. For example, the reader for the reader:target pair 700 comprises a core 702 or a ferromagnetic shield disposed around a coil 704. The coil 704 can also be referred to as the target reader 406. The reader:target pair 700 further comprises a target 706 which is shown inserted in a tool receiving assembly 708. The target 706 may be located on a tool 404. The coil 704 may be approximately 3 to 5 millimeters long and the core 702 may comprise a ferromagnetic material that is approximately 13 millimeters long. The coil 704 may detect the presence of the target 706 by sensing a change in inductance. FIG. 7B shows a table 710 that contains performance information for a plurality of reader/target pairs featuring a copper solenoid coil 704, a ferromagnetic core 702, and a ferromagnetic target 706. The table 710 includes columns for core length, current, inductance, inductance change, core outer diameter, and distance to target (CL). This table illustrates the ability of the coil 704 to detect the target 706 within a reasonable distance to the target (e.g. 2.5 mm and 4.5 mm). The table 710 also shows how some variations in the length of the core, the current applied to the core, the outer diameter of the target 706, and the distance of the target 706 to the coil 704 (i.e. the reader) can affect the detected change in inductance.

Referring now to FIGS. 8A-8F, it may be desirable to have an elongated target of a certain length (e.g., 40 mm, 50 mm, or even 60 mm, long). As described above, elongated targets (e.g. target 528 in FIGS. 5K and 5L) can be used for algorithms that are designed to detect a single target with two separated readers simultaneously. However, some challenges arise with these elongated targets, such as manufacturing a hollow cylinder target with the desired length and diameter while providing a certain degree of flexibility to minimize damage to the elongated target during use.

Referring to FIG. 8A, manufacturing a hollow cylinder target 800 with the desired length of possibly 60 mm can be done by manufacturing shorter length target sections (e.g., tube sections, half-cylinder sections, or sections of any other suitable shape) and bonding the shorter sections together to form the elongated target 800. For example, two 30 mm long target sections 810 can be manufactured separately and then bonded together at their ends. FIG. 8A shows an end 830 of a first target section 810 bonded to an end 820 of a second target section 810 to form the elongated target 800. In addition to being bonded together, one end (e.g. end 830) can be configured to receive another end (e.g. 820) with a mating feature that provides an even stronger joint than bonding squared off ends 820, 830. Other lengths of the target 800 can be manufactured by making target sections of various lengths and bonding them end to end to produce the elongated target 800. Therefore, the elongated target 800 can comprise two or more target sections of various lengths to achieve the desired overall length of the elongated target 800.

Referring to FIG. 8B, a target section 810 is shown with ends 820 and 830. The end 820 of one target section 810 is configured to mate with an end 830 of another target section 810. The inner diameter D1 of the target section 810 is generally constant throughout the length of the target section 810 except for near the end 830. At length L7 from the end 820, the outer diameter can gradually decrease toward the end 820 forming a tapered outer diameter with angle A1 (see FIG. 8C). Additionally, at length L8 from the end 830, the inner diameter can gradually increase toward the end 830 forming a tapered inner diameter with an angle A1 (see FIG. 8D). The tapered outer diameter of the end 820 can mate with the tapered inner diameter of the end 830. By inserting an end 820 of a first target section 810 into an end 830 of a second target section 810 and bonding the mated ends together, an elongated target 800 can be formed, which can provide increased resistance to damage caused by bending forces acting on the elongated target 800 during a procedure. The tapered ends increase strength of the bonded joint of the mated sections 810.

Referring to FIG. 8E, an elongated target 840 can be formed by coiling a metal wire around the tool 404. The coiled wire may be a biasing member, such as a spring, or a non-biasing member. The coiled wire can provide flexibility to the target 840 which can help prevent damage to the target 840 or the tool 404 as the tool 404 is installed in the tool recognition assembly 410. The flexibility can allow the target 840 to be up to 60 mm long or longer, without significantly impacting the use of the tool 404 with the tool recognition assembly 410. As compared to a cylindrical tube, the coiled target 840 may be less rigid and may be less likely to cause the tool 404 to kink at a transition between the tool shaft and the target.

Referring to FIG. 8F, another flexible elongated target can be made by taking a tube 852 at the desired length (i.e. 30 mm, 50 mm, 60 mm, etc.) and cutting a helically extending groove 854 around the exterior surface of the tube 852 to increase the flexibility of the elongated target 850. The tube 852 may be metal, plastic, or any other suitable material. Again, the flexibility can allow the target 850 to be up to 60 mm long or longer, without significantly impacting the use of the tool 404 with the tool recognition assembly 410. Please note that the spacing between adjacent loops of the helical groove can be varied. The elongate target 850 can provide sufficient flexibility to support installation into the tool recognition assembly and insertion into the anatomy of a patient P, as well as providing more material that can enhance detection of the target 850 by the target readers 406.

Referring now to FIG. 9, a method 900 may be performed by a control system (e.g., control system 112) using one or more elements of the tool recognition assembly 410, and may be implemented in the surgical environment 300 and/or the teleoperated medical system 100. The method 900 is illustrated as a set of processes 902 through 910. It is not a requirement that all of the illustrated processes 902 through 910 be performed in all implementations of the method 900. Furthermore, additional processes not expressly illustrated in FIG. 9 may be included before, after, in between, or as a part of the processes 902 through 910. In some cases, one or more of the illustrated processes may be implemented, at least in part, in the form of executable code stored on non-transitory, tangible, machine-readable media that when executed by one or more processors may cause the one or more processors to perform one or more of the processes.

At process 902, a tool recognition assembly, such as tool recognition assembly 410, can detect or calculate a baseline sensor data reading for one or more target readers. The baseline sensor data reading can be calculated based on readings from a dedicated baseline target reader which can obtain sensor data readings for a detection zone of the baseline reader that is empty. Since the baseline reader can be dedicated to providing a baseline reading, the detection zone of the baseline reader may remain empty throughout an operation of the tool recognition assembly 410. The baseline sensor data reading can also be calculated based on readings from one of the target readers which can obtain sensor data readings for a detection zone of the reader that is empty (e.g. at a time when the tool 404 is not installed in the tool recognition assembly 410). This process may be optional.

At process 904, an instrument is received into the insertion assembly. For example, a tool 404 can be received into the tool recognition assembly 410. At process 906, the control system 112 can compare a sensor data reading for the one or more target readers to the baseline sensor data readings. The comparison can be used to calculate a change in the sensor data values from the baseline sensor data values. At process 908, the control system 112 can determine, based on the change in the sensor data from the baseline sensor data, whether, for example, the tool 404 is present or absent in the tool recognition assembly 410, whether the tool 404 is fully installed into the tool recognition assembly 410, and/or the classification of the instrument (e.g. medical probe, endoscopic camera, catheter, etc.). When the tool 404 is being installed in the tool recognition assembly 410, changes in the sensor data of the one or more readers can be logged as a detected insertion signature of the tool 404. When the tool 404 is installed in the tool recognition assembly 410, the logged detected insertion signature can be compared to one or more pre-established model insertion signatures to determine if the tool 404 is fully installed in the tool recognition assembly 410. Also, as previously described, the logged detected insertion signature can also be compared to one or more pre-established model insertion signatures to determine the classification of the tool 404 (e.g. the type of tool 404, the particular tool 404, etc.).

At process 910, the control system 112 can determine or select an operating mode based on the comparison of the logged detected insertion signature to the one or more pre-established model insertion signatures. For example, if the tool 404 is fully installed in the tool recognition assembly 410, then one mode of operation can be initiated (e.g. such as proceeding with an operation that advances the tool 404 and catheter). If the tool 404 is not fully installed in the tool recognition assembly 410, then another mode of operation can be initiated (e.g. fully install the tool 404). Additionally, depending upon the type of the tool 404 determined by the comparison of the detected insertion signature to the model insertion signatures, another mode of operation can be initiated (e.g. limiting insertion speed of the tool 404 into a patient's anatomy, dimming optical sources, limiting catheter flexibility, increasing catheter flexibility, limiting the speed at which adjustments to the catheter may be made, disabling/enabling certain functionalities such as image collection, etc.). Different functionalities may be enabled or disabled depending on the tool 404 that is fully inserted into the tool recognition assembly 410.

Referring now to FIGS. 10A-10C, tables representing multiple detected insertion signatures 1000 are provided, with each table representing a detected insertion signature 1000. Each detected insertion signature 1000 can be described as an algorithm with a sequence of events (or conditions) that occur as the tool 404 is installed into the tool recognition assembly 410. These events occur when the target readers detect a presence or absence of a target within a reader's detection zone. Detection of the presence ("1") or absence ("0") of the target can be determined by various means, such as those described above regarding FIGS. 4A-4J and FIGS. 5A-5S. These events can include signal strength (or intensity), signal duration, rate of change of the signal, multiple thresholds of signal strength, a slope of a detected signal, inductance measurement ratios, and/or other derivatives of an inductance measurement signal. Therefore, the presence ("1") and absence ("0") indicators in tables 1002-1018 can be determined by any of the means described in this disclosure. By logging these events in sequence (e.g. chronologically), a detected insertion signature (that include a certain sequence of readings) can be established and then compared to one or more pre-established model insertion signatures. The tables 1002-1018 are directed to a tool recognition assembly 500, where a tool recognition assembly 410 can include two detectors (e.g. one absence A target reader 510, and one presence P target reader 512) and can receive a tool 404 which includes one or two targets (e.g. targets 526, 528), similar to the systems (e.g., tool recognition assembly 500) shown in FIGS. 5E-5L.

As used herein, when a target is "detected" by a target reader or the target reader "detects" the target, this indicates that the target is positioned within a detection zone of the target. As used here, the "detection zone" of a target reader is defined as a longitudinal distance along the tool recognition assembly 410 within which a detection of the target is determined by sensing a parameter that varies based on proximity of the target to the target reader and determining if a value of the parameter is above or below a pre-determined threshold value. For example, for electromagnetic reader/target sets, the parameter can be inductance change, and the pre-determined threshold value can be the inductance change that above which the target is seen to have been "detected" within the detection zone. It should be understood that detection zones of multiple readers can overlap each other as well as be separated from each other. As way of another example, for optical reader:target pairs, the parameter can be light intensity, and a pre-determined threshold value can be a light intensity that above which the target is seen as being detected, or the pre-determined threshold value can be a light intensity that below which the target is seen as being detected (such as when the instrument is a lighter color, like a shade of white, and the target is a darker color, e.g. black). Other threshold values can be used for the other reader/target set types, such as the returned RF signals from an RFID being scanned where the threshold can be merely if the RFID is readable.

Each table includes an algorithm number (e.g. 1-11) which designates the algorithm being described by the table, an algorithm sequence number (e.g. 1.1, 1.2, 1.3, etc.) which indicates the detection of a presence or absence of a target within a detection zone of each target reader. A "0" indicates an absence of a target within the detection zone of that particular target reader, and a "1" indicates a presence of a target within the detection zone. An absence (i.e. "0") of the target in the detection zone can be determined when the target reader detects values of the particular signals (e.g. optical signals, electromagnetic signals, RF scan signals, magnetic flux signals, etc.) that are below a pre-determined threshold. A presence (i.e. "1") of the target in the detection zone can be determined when the target reader detects values of the particular signals (e.g. optical signals, electromagnetic signals, RF scan signals, magnetic flux signals, etc.) that are above or below the pre-determined threshold and/or within a ratio of a measurement compared to a baseline measurement. However, in the example of a bar code reader/target pair, the absence or presence of the target (i.e. a bar code) can be determined when a pattern detected by the barcode reader is a valid barcode or not. If "N/A" is used in the table, this indicates that a particular target (or reader) is not used in the algorithm and will not supply detection information for that sequence event.

Each table also indicates whether or not a "stripe" is detected. As used herein, a "stripe" refers to a longitudinal marking included on an inside surface of a medical instrument, such as a catheter (e.g. 450 in FIG. 4B) that can serve as a reference point or frame. As a tool 404 is installed in the catheter, a camera at a distal end 413 of the tool 404 can collect images from within the catheter prior to the tool 404 being fully installed in the catheter. The longitudinal marking can be any feature that is visible on the inside surface of the catheter and is distinguishable from the rest of the inner surface of the catheter. Also, the longitudinal marking can occupy a small circumferential distance of the inner surface when compared to the full circumferential distance around the inner surface. Therefore, the longitudinal marking can form a longitudinal stripe that extends along a significant portion of the catheter's inner surface.

Referring to FIG. 11, a representative image from inside a catheter is shown. By collecting images 1100 from within the catheter 1012 during installation of the tool 404, it can be verified that the tool 404 is at least partially installed in the catheter 1012 by viewing the longitudinal marking 1010 in the images 1100. After determining that the tool 404 is at least partially installed in the catheter, the reader:target pairs can be used to verify when the tool 404 is fully installed in the catheter (or the tool recognition assembly 410). It should be understood that the stripe detection is not required, but merely an option when establishing a detected insertion signature. The reader:target pairs can verify full installation of the tool 404, as well as indicate other characteristics of the tool 404, such as the classification of the tool 404.

Table 1002 describes the algorithm 1, which includes sequences 1.1-1.3. Algorithm 1 involves an absence reader 510, a presence reader 512, and a target 526 at a proximal portion of the tool 404. As the tool 404 is installed in the tool recognition assembly 410, the readers 510, 512 can detect the event sequence that make up a detected insertion signature as shown in the table 1002. The sequence event 1.1 indicates that neither reader detects the target 526. The sequence event 1.2 indicates that the absence reader 510 detects the target 526, while the presence reader 512 does not detect the target 526. The sequence event 1.3 indicates that the absence reader 510 does not detect the target 526, while the presence reader 512 detects the target 526.

Table 1004 describes the algorithm 2, which includes sequences 2.1-2.3. Algorithm 2 involves stripe detection, an absence reader 510, a presence reader 512, and a target 526 at a proximal portion of the tool 404. As the tool 404 is installed into the tool recognition assembly 410, a camera at the end of the tool 404 can capture an image inside of a catheter. Viewing the captured image(s) can provide verification that the tool 404 is at least partially installed in the tool recognition assembly 410. After the stripe is detected, the readers can detect the sequence shown in the table 1004 as the tool 404 is installed in the assembly 410. The table 1004 (i.e. algorithm 2) is similar to table 1002 (i.e. algorithm 1), except that a stripe detection event has been added. The sequence event 2.1 indicates that the stripe has been detected and that neither reader detects the target 526. The sequence event 2.2 indicates that the absence reader 510 detects the target 526, while the presence reader 512 does not detect the target 526. The sequence event 2.3 indicates that the absence reader 510 does not detect the target 526, while the presence reader 512 detects the target 526.

Table 1006 describes the algorithm 3, which includes sequences 3.1-3.4. Algorithm 3 involves an absence reader 510, a presence reader 512, and a target 528 near a proximal portion of the tool 404. If the readers are located at the same positions in the tool recognition assembly 410 as the readers in algorithm 1, then, since the target is near the proximal portion, but not at the proximal portion, the target may travel past both readers when the tool 404 is fully installed. As the tool 404 is installed into the assembly 410, the readers 510, 512 can detect the sequence shown in the table 1006. The sequence event 3.1 indicates that neither reader 510, 512 detects the target 528. The sequence event 3.2 indicates that the absence reader 510 detects the target 528, while the presence reader 512 does not detect the target 528. The sequence event 3.3 indicates that the absence reader 510 does not detect the target 528, while the presence reader 512 detects the target 528. The sequence event 3.4 indicates that neither reader 510, 512 detects the target 528.

Table 1008 describes the algorithm 4, which includes sequences 4.1-4.5. Algorithm 4 involves an absence reader 510, a presence reader 512, a target 526 at the proximal portion of the tool 404, and a target 528 near the proximal portion of the tool 404, but spaced away from the proximal portion. In this example, the spacing between targets 526, 528 is less than the spacing between the readers 510, 512. Therefore, the targets 528, 526 can pass through the detection zone of the absence reader 510 before either target 526, 528 enters the detection zone of the presence reader 512. The sequence event 4.1 indicates that neither reader 510, 512 detects either one of the targets 526, 528. The sequence event 4.2 indicates that the absence reader 510 detects the target 528 but does not detect the target 526, while the presence reader 512 does not detect either targets 526, 528. This can be expected for this example, since the near proximal end target 528 can reach the absence reader 510 first as the tool 404 in installed in the assembly 410. As the tool 404 is further installed in the assembly 410, the target 528 can pass the absence reader 510 and the target 526 can enter the detection zone of the absence reader 510 next. Therefore, the sequence event 4.3 indicates that the absence reader 510 detects the target 526 but does not detect the target 528, while the presence reader 512 continues to not detect either targets 526, 528. The sequence event 4.4 indicates that the presence reader 512 detects the target 528 but does not detect the target 526, while the absence reader 510 does not detect either target 526, 528. The sequence event 4.5 indicates that the absence reader 510 does not detect either target 526, 528, while the presence reader 512 detects the target 526, but does not detect the target 528.

Table 1010 describes the algorithm 5, which includes sequences 5.1-5.5. Algorithm 4 involves stripe detection, an absence reader 510, a presence reader 512, a target 526 at the proximal portion the tool 404, and a target 528 near the proximal portion of the tool 404, but spaced away from the proximal portion. As the tool 404 is installed into the tool recognition assembly 410, a camera at the end of the tool 404 can capture an image inside of a catheter. Viewing the captured image(s) can provide verification that the tool 404 is at least partially installed in the tool recognition assembly 410. After the stripe is detected, the readers can detect the sequence shown in the table 1010 as the tool 404 is installed in the assembly 410. The table 1010 (i.e. algorithm 5) is similar to table 1008 (i.e. algorithm 4), except that a stripe detection event has been added. The sequence event 5.1 indicates that the stripe has been detected and that neither reader 510, 512 detects either one of the targets 526, 528. The remaining sequences 5.2-5.5 are the same as sequences 4.2-4.5 of algorithm 4, whose description is given above.

Referring now to FIG. 10B, table 1012 describes the algorithm 6, which includes sequences 6.1-6.4. Algorithm 6 involves an absence reader 510, a presence reader 512, and an elongated target 526 at a proximal portion of the tool 404. As the tool 404 is installed in the tool recognition assembly 410, the readers 510, 512 can detect the sequence of readings as shown in the table 1002. The elongated target 526 is long enough to extend into both detection zones of the readers 510, 512. The sequence event 6.1 indicates that neither reader detects the elongated target 526. The sequence event 6.2 indicates that the absence reader 510 detects the elongated target 526, while the presence reader 512 does not detect the elongated target 526. The sequence event 6.3 indicates that both readers 510, 512 detect the elongated target 526. The sequence event 6.3 indicates that the absence reader 510 does not detect the elongated target 526, while the presence reader 512 detects the elongated target 526.

Table 1014 describes the algorithm 7, which includes sequences 7.1-7.5. Algorithm 7 involves an absence reader 510, a presence reader 512, and a target elongated 528 near a proximal portion of the tool 404. If the readers are located at the same positions in the tool recognition assembly 410 as the readers in algorithm 6, then, since the target is near the proximal portion, but not at the proximal portion, the target may travel past both readers when the tool 404 is fully installed. As the tool 404 is installed into the assembly 410, the readers 510, 512 can detect the sequence shown in the table 1014. The sequence event 7.1 indicates that neither reader 510, 512 detects the elongated target 528. The sequence event 7.2 indicates that the absence reader 510 detects the elongated target 528, while the presence reader 512 does not detect the target elongated 528. The sequence event 7.3 indicates that both readers 510, 512 detect the elongated target 528. The sequence event 7.4 indicates that the absence reader 510 does not detect the elongated target 528, while the presence reader 512 detects the target elongated 528. The sequence event 7.5 indicates that neither reader 510, 512 detects the target elongated 528.

Table 1016 describes the algorithm 8, which includes sequences 8.1-8.7. Algorithm 8 involves an absence reader 510, a presence reader 512, an elongated target 526 at a proximal portion of the tool 404, and an elongated target 528 near the proximal portion of the tool 404, but spaced away from the proximal portion. The sequence event 8.1 indicates that readers 510, 512 do not detect either of the elongated targets 526, 528. The sequence event 8.2 indicates that the absence reader 510 detects the elongated target 528 but does not detect the elongated target 526, while the presence reader 512 does not detect either of the elongated targets 526, 528. This can be expected for this example, since the near proximal portion elongated target 528 can reach the absence reader 510 first as the tool 404 in installed in the assembly 410. As the tool 404 is further installed in the assembly 410, the elongated target 528 can extend into the detection zone of the presence reader 512 while a portion of the elongated target 528 remains in the detection zone of the absence reader 510. Therefore, the sequence event 8.3 indicates that both readers 510, 512 detect the elongated target 528, while neither reader 510, 512 detects the elongated target 526.

The sequence event 8.4 indicates that the absence reader 510 no longer detects the elongated target 528 but the presence reader detects the elongated target 528, while neither reader 510, 512 detects the elongated target 526. In this example, the spacing between the elongated targets 526, 528 is greater than the spacing between the readers 510, 512. Therefore, the elongated target 528 can pass through the detection zone of the presence reader 512 before the elongated target 526 enters the detection zone of the absence reader 510. The sequence event 8.5 indicates that the absence reader 510 detects the elongated target 526 but does not detect the elongated target 528, while neither reader 510, 512 detects the elongated target 528. As the tool 404 is further installed in the assembly 410, the elongated target 526 can extend into the detection zone of the presence reader 512 while a portion of the elongated target 526 remains in the detection zone of the absence reader 510. Therefore, the sequence event 8.6 indicates that both readers detect the elongated target 526, while neither reader 510, 512 detect the elongated target 528. The sequence event 8.7 indicates that the absence reader 510 does not detect either of the elongated target 526, 528, while the presence reader 512 detects the elongated target 526, but does not detect the elongated target 528.

Table 1018 describes the algorithm 9, which includes sequences 9.1-9.7. Algorithm 8 involves stripe detection, an absence reader 510, a presence reader 512, an elongated target 526 at a proximal portion of the tool 404, and an elongated target 528 near the proximal portion of the tool 404, but spaced away from the proximal portion. As the tool 404 is installed into the tool recognition assembly 410, a camera at the end of the tool 404 can capture an image inside of a catheter. Viewing the captured image(s) can provide verification that the tool 404 is at least partially installed in the tool recognition assembly 410. After the stripe is detected, the readers can detect the sequence shown in the table 1016 as the tool 404 is installed in the assembly 410. The table 1018 (i.e. algorithm 9) is similar to table 1016 (i.e. algorithm 8), except that a stripe detection event has been added. The sequence event 9.1 indicates that the stripe has been detected and that readers 510, 512 do not detect either of the elongated targets 526, 528. The remaining sequences 9.2-9.7 are the same as sequences 8.2-8.7 of algorithm 8, whose description is given above.

Referring now to FIG. 10C, table 1020 describes the algorithm 10, which includes sequences 10.1-10.6. Algorithm 10 involves an absence reader 510, a presence reader 512, a target 526 at a proximal portion of the tool 404, and a target 528 near the proximal portion of the tool 404, but spaced away from the proximal portion. This algorithm captures the detected insertion signature discussed above in reference to FIGS. 5E-5J. The sequence event 10.1 indicates that readers 510, 512 do not detect either of the targets 526, 528. The sequence event 10.2 indicates that the absence reader 510 detects the target 528 but does not detect the target 526, while the presence reader 512 does not detect either of the targets 526, 528. The sequence event 10.3 indicates that readers 510, 512 again do not detect either of the targets 526, 528. In this example, the spacing between the readers 510, 512 is similar to the spacing between the targets 526, 528. Therefore, the targets 526, 528 can be positioned in the detection zones of the absence and presence readers 510, 512, respectively. Therefore, as the tool 404 is further installed in the assembly 410, the target 528 can enter the detection zone of the presence reader 512 while the target 526 enters the detection zone of the absence reader 510. The sequence event 10.4 indicates that the absence reader 510 detects the target 526, but does not detect the target 528, while the presence reader 512 detects the target 528, but does not detect the target 526. The sequence event 10.5 indicates that readers 510, 512 again do not detect either of the targets 526, 528. The sequence event 10.6 indicates that absence reader does not detect either of the targets 526, 528, while the presence reader 512 detects the target 526, but does not detect the target 528.

Table 1022 describes the algorithm 11, which includes sequences 11.1-11.6. Algorithm 11 involves stripe detection, an absence reader 510, a presence reader 512, a target 526 at a proximal portion of the tool 404, and a target 528 near the proximal portion of the tool 404, but spaced away from the proximal portion. As the tool 404 is installed into the tool recognition assembly 410, a camera at the end of the tool 404 can capture an image inside of a catheter. Viewing the captured image(s) can provide verification that the tool 404 is at least partially installed in the tool recognition assembly 410. After the stripe is detected, the readers can detect the sequence shown in the table 1022 as the tool 404 is installed in the assembly 410. The table 1022 (i.e. algorithm 11) is similar to table 1020 (i.e. algorithm 10), except that a stripe detection event has been added. The sequence event 11.1 indicates that the stripe has been detected and that readers 510, 512 do not detect either of the targets 526, 528. The remaining sequences 11.2-11.6 are the same as sequences 10.2-10.6 of algorithm 10, whose description is given above.

Note that the processes and displays presented may not inherently be related to any particular computer or other apparatus. The required structure for a variety of these systems will appear as elements in the claims. In addition, the embodiments are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
  a tool recognition assembly coupled to a teleoperated manipulator, the tool recognition assembly comprising:
    a first reader with a first detection zone; and
    a second reader with a second detection zone, wherein the second reader is spaced apart from the first reader along an insertion axis;
  a tool configured to be inserted into the tool recognition assembly along the insertion axis, the tool comprising a first target, wherein as the tool is inserted into the tool recognition assembly along the insertion axis, the first reader detects a first reading indicating a presence or absence of the first target in the first detection zone, wherein as the tool is inserted into the tool recognition assembly along the insertion axis, the second reader detects a second reading indicating a presence or absence of the first target in the second detection zone; and a control system communicatively linked to the first reader and the second reader, the control system configured to:

receive the first reading from the first reader and the second reading from the second reader, the first reading and the second reading forming at least a part of an insertion signature; and compare the insertion signature to one or more model signatures.

2. The system of claim 1, wherein the tool further comprises a second target spaced from the first target by a separation distance, wherein as the tool is inserted into the tool recognition assembly, the first reader of the tool recognition assembly detects a third reading indicating a presence or absence of the second target in the first detection zone, wherein the first reading, the second reading, and the third reading form at least part of the insertion signature.

3. The system of claim 2, wherein the separation distance ranges from 7 mm to 68 mm.

4. The system of claim 2, wherein the insertion signature is determined when the first target is in alignment with the first reader, and the second target is out of alignment with the second reader.

5. The system of claim 1, wherein the first target comprises two or more target sections, wherein the first reader comprises two or more reader sections and each one of the reader sections of the first reader includes an associated detection zone, wherein each reader section of the first reader detects a portion of the first reading indicating a presence or absence of at least one of the target sections in the detection zone of the first reader.

6. The system of claim 1, wherein the first reader comprises one or more of an inductive sensor, a capacitive sensor, a Hall effect sensor, a photogate sensor, an optical sensor, a magnetic switch, a barcode scanner, an RFID scanner, or a relative position sensor.

7. The system of claim 1, wherein the first target comprises one or more of a ferromagnetic material, a metal cylinder, a magnet, an aperture, a surface or material with varied optical absorption properties, a barcode, an RFID chip, or an optical light source.

8. The system of claim 7, wherein the first target comprises an elongate target with a length of the elongate target being in a range of 20 mm to 60 mm.

9. The system of claim 8, wherein the elongate target comprises one or more of multiple tube sections bonded together, a spring wrapped around the tool, or a metal tube, with a helical groove cut in an exterior surface of the metal tube, positioned on the tool.

10. The system of claim 1, wherein the comparison of the insertion signature to the one or more model signatures identifies a match between the insertion signature and the one or more model signatures, the match indicating a characteristic of the tool.

11. The system of claim 10, wherein the characteristic of the tool includes an absence or presence of the tool in the tool recognition assembly, a position of the tool in the tool recognition assembly, whether the tool is fully installed in the tool recognition assembly, a classification of the tool, whether the tool is a counterfeit tool, whether the tool is a competitor's tool, or combinations thereof.

12. The system of claim 11, wherein the classification of the tool comprises a type of the tool and a unique identifier of the tool.

13. The system of claim 11, wherein the tool recognition assembly includes a control mode changeable based on the characteristic.

14. The system of claim 1, wherein the first detection zone is a distance along an insertion trajectory path of the tool being inserted into the tool recognition assembly, and wherein the distance of the first detection zone ranges from 7 mm to 68 mm.

15. The system of claim 1, wherein the tool includes a camera at a distal end of the tool that captures a series of images along an insertion trajectory path of the tool as the tool is inserted into the tool recognition assembly, and the series of images are provided to initiate verification of a progress of the insertion of the tool.

16. The system of claim 15, wherein the camera is configured to detect a marking on a surface along the insertion trajectory path of the tool as the tool is inserted into the tool recognition assembly and the captured series of images include an image of the marking.

17. The system of claim 1, wherein the comparison of the insertion signature to the one or more model signatures identifies a match between the insertion signature and the one or more model signatures, the match indicating an axial position of the tool in the tool recognition assembly.

18. A tool shaped for insertion along an insertion axis into a tool recognition assembly coupled to a teleoperated manipulator, the tool including:

an elongated body; and a first target positioned along the elongated body, wherein as the tool is inserted into the tool recognition assembly along the insertion axis, the first target passes a first target reader in the tool recognition assembly and a second target reader in the tool recognition assembly, wherein the second target reader is spaced apart from the first target reader along an insertion axis, wherein as the tool is inserted into the tool recognition assembly along the insertion axis, the first target reader in the tool recognition assembly detects:

a first target reading indicating a presence of the first target when the first target is proximate the first target reader; and a second target reading indicating an absence of the first target when the first target is out of range of the first target reader, wherein as the tool is inserted into the tool recognition assembly along the insertion axis, the second target reader in the tool recognition assembly detects:

a third target reading indicating a presence of the first target when the first target is proximate the second target reader; and a fourth target reading indicating an absence of the first target when the first target is out of range of the second target reader, and wherein the first reading, second reading, third reading, and fourth reading form at least a part of an insertion signature.

19. The tool of claim 18, wherein the first target comprises one or more of a ferromagnetic material, a metal cylinder, a magnet, an aperture, a surface or material with varied optical absorption properties, a barcode, an RFID chip, or an optical light source.

20. The tool of claim 19, wherein the elongate target comprises one or more of multiple tube sections bonded together, a spring wrapped around the tool, or a metal tube, with a helical groove cut in an exterior surface of the metal tube, positioned on the tool.

* * * * *